(12) United States Patent
Sato et al.

(10) Patent No.: US 6,284,462 B1
(45) Date of Patent: Sep. 4, 2001

(54) PROBES AND METHODS FOR POLYNUCLEOTIDE DETECTION

(75) Inventors: Yoshihiro Sato, Aichi; Akihiko Tsuji; Takayuki Suga, both of Hamakita, all of (JP)

(73) Assignee: Laboratory of Molecular Biophotonics, Hamakita (JP)

( * ) Notice: Subject to any disclaimer, the term of this patent is extended or adjusted under 35 U.S.C. 154(b) by 0 days.

(21) Appl. No.: 09/091,332

(22) PCT Filed: Sep. 26, 1997

(86) PCT No.: PCT/JP97/03438

§ 371 Date: Jun. 16, 1998

§ 102(e) Date: Jun. 16, 1998

(87) PCT Pub. No.: WO98/13524

PCT Pub. Date: Apr. 2, 1998

(30) Foreign Application Priority Data

Sep. 27, 1996 (JP) .................................................. 8-256833

(51) Int. Cl.⁷ ...................................................... C12Q 1/68

(52) U.S. Cl. ............................ 435/6; 536/22.1; 536/25.3

(58) Field of Search ................................ 435/6; 536/22.1, 536/25.3

(56) References Cited

U.S. PATENT DOCUMENTS

| | | | |
|---|---|---|---|
| 4,822,733 | * 4/1989 | Morrison | 435/6 |
| 4,868,103 | 9/1989 | Stavrianopoulos et al. | 435/5 |
| 4,996,143 | 2/1991 | Heller et al. | 435/6 |
| 5,274,113 | 12/1993 | Kang et al. | 548/405 |
| 5,326,692 | 7/1994 | Brinkley et al. | 435/6 |
| 5,532,129 | 7/1996 | Heller | 435/6 |
| 5,827,653 | * 10/1998 | Sammes et al. | 435/6 |

FOREIGN PATENT DOCUMENTS

| | | |
|---|---|---|
| 0 070 685 | 1/1983 | (EP) . |
| 0 229 943 | 7/1987 | (EP) . |
| 0 601 889 | 6/1994 | (EP) . |
| 0 668 498 | 8/1995 | (EP) . |
| 6-201256 | 10/1985 | (JP) . |
| 7-063400 | 3/1995 | (JP) . |
| 7-229835 | 8/1995 | (JP) . |
| 7-233187 | 9/1995 | (JP) . |
| WO 92/14845 | 9/1992 | (WO) . |
| WO 93/09128 | 5/1993 | (WO) . |
| WO 93/09185 | 5/1993 | (WO) . |
| WO 93/23492 | 11/1993 | (WO) . |
| WO 96/19731 | 6/1996 | (WO) . |
| WO 96/25518 | 8/1996 | (WO) . |

OTHER PUBLICATIONS

Cardullo et al., Detection of Nucleic Acid Hybridization by Nonradiative Fluorescence Resonance Energy Transfer, *Proc. Natl. Acad. Sci. USA*, vol. 85, pp. 8790–8794 (Dec. 1988).

Morrison, Time–Resolved Detection of Energy Transfer: Theory and Application to Immunoassays, *Analytical Biochemistry*, vol. 174, pp. 101–120 (1988).

Soper et al., On–Line Fluorescence Lifetime Determinations in Capillary Electrophoresis, *Anal. Chem.*, vol. 67, pp. 4358–4365 (1995).

* cited by examiner

*Primary Examiner*—Ardin H. Marschel
(74) *Attorney, Agent, or Firm*—Leydig, Voit & Mayer, Ltd.

(57) ABSTRACT

Detection probes and a method of detection for the detection of a specimen having a specified sequence in a sample are disclosed that utilize two fluorophore-labeled (donor and acceptor) probes which are designed to display changes in a fluorescence decay curve by their hybridization to the specific sequence of a specimen, thus allowing for the detection with great accuracy and high sensitivity, particularly under the conditions where the probes may be abundant relative to the specimen in the sample.

9 Claims, 37 Drawing Sheets

Fig.6A
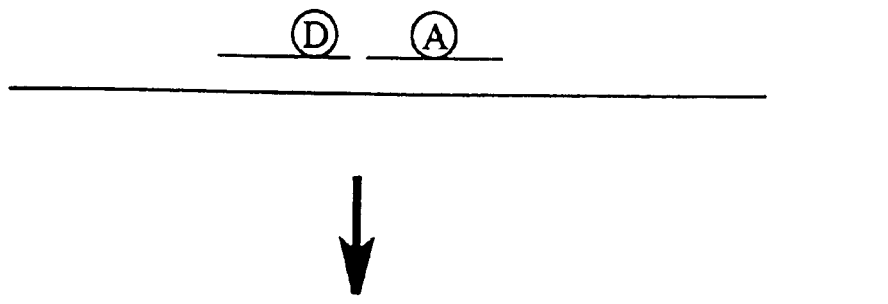
Fig.6B
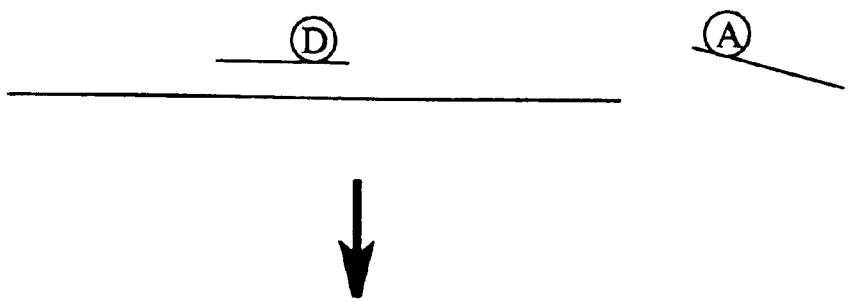
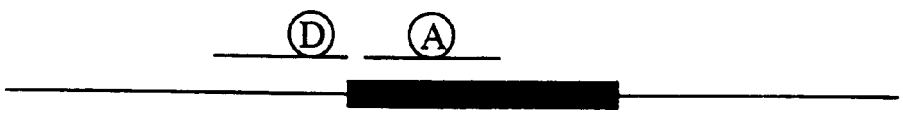

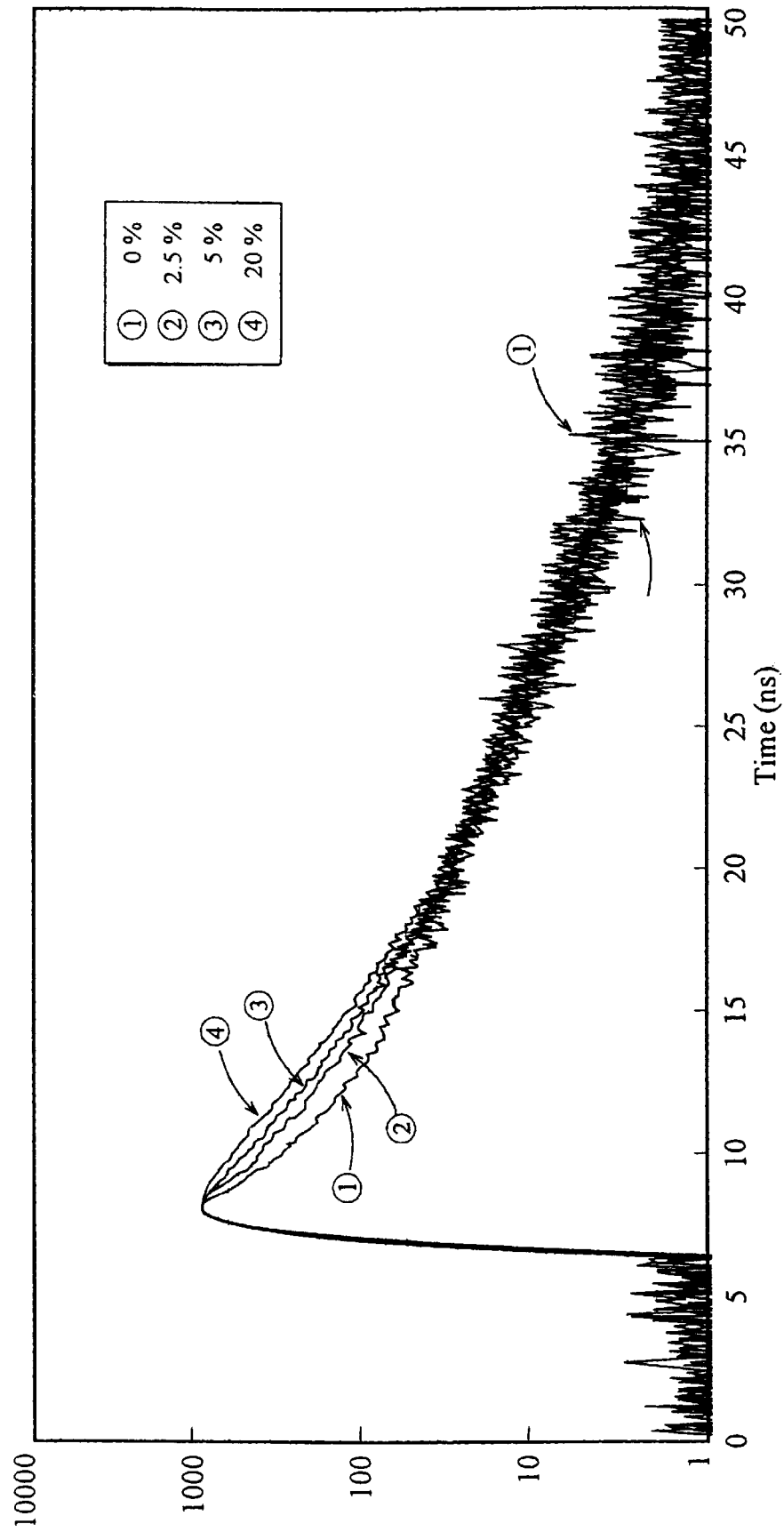

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:1:

GCTATGACCA TGNTTAC                                                  17

(2) INFORMATION FOR SEQ ID NO:2:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:2:

GCTATGACCA NGATTAC                                                  17

(2) INFORMATION FOR SEQ ID NO:3:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

GCTATGACNA TGATTAC                                                  17

(2) INFORMATION FOR SEQ ID NO:4:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:4:

GCTATGANCA TGATTAC                                                    17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:5:

GCTATGNCCA TGATTAC                                                    17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:6:

GCTANGACCA TGATTAC                                                    17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

GCNATGACCA TGATTAC                                                    17

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:8:

ANCGCGCAAT TAACCC                                                     16

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:9:

AGNGCGCAAT TAACCC      16

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:10:

AGCGNGCAAT TAACCC      16

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:11:

NAGCGCGCAA TTAACCC      17

(2) INFORMATION FOR SEQ ID NO:12:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:12:

NCCATGATTA C      11

(2) INFORMATION FOR SEQ ID NO:13:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:13:

NGACCATGAT TAC                                                                13

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:14:

NTGACCATGA TTAC                                                               14

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:15:

NTATGACCAT GATTAC                                                             16

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:16:

NGCTATGACC ATGATTAC                                                           18

(2) INFORMATION FOR SEQ ID NO:17:

(i) SEQUENCE CHARACTERISTICS:
        (A) LENGTH: 18 base pairs

```
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:17:

GCTATGACCA TGATTACN                                              18

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:18:

NAGCGCGCAA TTAACCC                                               17

(2) INFORMATION FOR SEQ ID NO:19:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:19:

ANCGCGCAAT TAACCC                                                16

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:20:

AGNGCGCAAT TAACCC                                                16

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear
```

(ii) MOLECULE TYPE: DNA (iii) HYPOTHETICAL: NO (iv) ANTI-SENSE: NO (xi) SEQUENCE DESCRIPTION: SEQ ID NO:21:

AGCGNGCAAT TAACCC                                                           16

(2) INFORMATION FOR SEQ ID NO:22:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:22:

NAGCGCGCAA TTAACCC                                                          17

(2) INFORMATION FOR SEQ ID NO:23:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:23:

NCCATGATTA C                                                                11

(2) INFORMATION FOR SEQ ID NO:24:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:24:

NGACCATGAT TAC                                                              13

(2) INFORMATION FOR SEQ ID NO:25:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:25:

NTGACCATGA TTAC                                                       14

(2) INFORMATION FOR SEQ ID NO:26:

(i) SEQUENCE CHARACTERISTICS:
			(A) LENGTH: 16 base pairs
			(B) TYPE: nucleic acid
			(C) STRANDEDNESS: single
			(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:26:

NTATGACCAT GATTAC                                                     16

(2) INFORMATION FOR SEQ ID NO:27:

(i) SEQUENCE CHARACTERISTICS:
			(A) LENGTH: 18 base pairs
			(B) TYPE: nucleic acid
			(C) STRANDEDNESS: single
			(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:27:

GCTATGACCA TGATTACN                                                   18

(2) INFORMATION FOR SEQ ID NO:28:

(i) SEQUENCE CHARACTERISTICS:
			(A) LENGTH: 17 base pairs
			(B) TYPE: nucleic acid
			(C) STRANDEDNESS: single
			(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:28:

NAGCGCGCAA TTAACCC                                                    17

(2) INFORMATION FOR SEQ ID NO:29:

(i) SEQUENCE CHARACTERISTICS:
			(A) LENGTH: 17 base pairs
			(B) TYPE: nucleic acid
			(C) STRANDEDNESS: single
			(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:29:

NAGCGCGCAA TTAACCC                                                    17

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:30:

GCTATGACNA TGATTAC                                                    17

(2) INFORMATION FOR SEQ ID NO:31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:31:

GCTANGACCA TGATTAC                                                    17

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:32:

NGCTATGACC ATGATTAC                                                   18

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:33:

```
GCTATGACCA TGNTTAC                                                    17
```

(2) INFORMATION FOR SEQ ID NO:34:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:34:

```
GCTATGACCA NGATTAC                                                    17
```

(2) INFORMATION FOR SEQ ID NO:35:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:35:

```
GCTATGACNA TGATTAC                                                    17
```

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:36:

```
GCTATGANCA TGATTAC                                                    17
```

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:37:

```
GCTATGNCCA TGATTAC                                                    17
```

```
(2) INFORMATION FOR SEQ ID NO:38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:38:

GCTANGACCA TGATTAC                                                  17

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:39:

GCNATGACCA TGATTAC                                                  17

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:40:

NAGCGCGCAA TTAACCC                                                  17

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:41:

GCTATGACCA TGATTACN                                                 18

(2) INFORMATION FOR SEQ ID NO:42:

(i) SEQUENCE CHARACTERISTICS:
```

```
            (A) LENGTH: 33 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:42:

GGGTTAATTG CGCGCTGTAA TCATGGTCAT AGC                                    33

(2) INFORMATION FOR SEQ ID NO:43:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:43:

GGGTTAATTG CGCGCTTGGT AATCATGGTC ATAGC                                  35

(2) INFORMATION FOR SEQ ID NO:44:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:44:

GGGTTAATTG CGCGCTTGGC GTAATCATGG TCATAGC                                37

(2) INFORMATION FOR SEQ ID NO:45:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:45:

GGGTTAATTG CGCGCTTGGC AAGTAATCAT GGTCATAGC 39

(2) INFORMATION FOR SEQ ID NO:46:

(i) SEQUENCE CHARACTERISTICS:
            (A) LENGTH: 41 base pairs
            (B) TYPE: nucleic acid
            (C) STRANDEDNESS: single
```

(D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:46:

GGGTTAATTG CGCGCTTGGC AAAAGTAATC ATGGTCATAG C                           41

(2) INFORMATION FOR SEQ ID NO:47:

(i) SEQUENCE CHARACTERISTICS:
         (A) LENGTH: 43 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:47:

GGGTTAATTG CGCGCTTGGC AAAAAAGTAA TCATGGTCAT AGC                         43

(2) INFORMATION FOR SEQ ID NO:48:

(i) SEQUENCE CHARACTERISTICS:
         (A) LENGTH: 45 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:48:

GGGTTAATTG CGCGCTTGGC AAAAAAAAGT AATCATGGTC ATAGC                       45

(2) INFORMATION FOR SEQ ID NO:49:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:49:

GGGTTAATTG CGCGCTTGGC AAAAAAAAAA AGTAATCATG GTCATAGC                    48

(2) INFORMATION FOR SEQ ID NO:50:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: DNA

```
        (iii) HYPOTHETICAL: NO (iv) ANTI-SENSE: NO (xi) SEQUENCE DESCRIPTION: SEQ ID NO:50:

GGGTTAATTG CGCGCTTGGC AAAAAAAAAA AAAAAAGTAA TCATGGTCAT AGC          53

(2) INFORMATION FOR SEQ ID NO:51:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:51:

NAGCGCGCAA TTAACCC                                                  17

(2) INFORMATION FOR SEQ ID NO:52:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:52:

NTCTAGTTGG TCTGTC                                                   16

(2) INFORMATION FOR SEQ ID NO:53:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: OTHER NUCLEIC ACID
                Phosphorothioate type oligonucleotide (S-oligo)

(iii) HYPOTHETICAL: NO (iv) ANTI-SENSE: NO (xi) SEQUENCE DESCRIPTION: SEQ ID NO:53:

NTCTAGTTGG TCTGTC                                                   16

(2) INFORMATION FOR SEQ ID NO:54:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (iii) HYPOTHETICAL: NO
```

(iv) ANTI-SENSE: NO (xi) SEQUENCE DESCRIPTION: SEQ ID NO:54:

GCTANGACCA TGATTAC                                                       17

(2) INFORMATION FOR SEQ ID NO:55:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:55:

GCANACTTCN TCATCT                                                        16

(2) INFORMATION FOR SEQ ID NO:56:

(i) SEQUENCE CHARACTERISTICS:
              (A) LENGTH: 16 base pairs
              (B) TYPE: nucleic acid
              (C) STRANDEDNESS: single
              (D) TOPOLOGY: linear (ii) MOLECULE TYPE: OTHER NUCLEIC ACID
              Phosphorothioate type oligonucleotide (S-oligo)

(iii) HYPOTHETICAL: NO (iv) ANTI-SENSE: NO (xi) SEQUENCE DESCRIPTION: SEQ ID NO:56:

GCAGANCTTC TCATCT                                                        16

(2) INFORMATION FOR SEQ ID NO:57:

(i) SEQUENCE CHARACTERISTICS:
              (A) LENGTH: 33 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:57:

GGGTTAATTG CGCGCTGTAA TCATGGTCAT AGC                                     33

(2) INFORMATION FOR SEQ ID NO:58:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:58:

GACAGACCAA CUAGAAGAUG AGAAGUCUGC    30

PROBES AND METHODS FOR POLYNUCLEOTIDE DETECTION

This application is a 371 filing of PCT/JP97/03438, filed Sep. 26, 1997.

TECHNICAL FIELD

This invention relates to techniques for detection probes and method of detection for detecting a specimen that has specified polynucleotide base (DNA, RNA or the like ), by mixing detection probes, which are labeled with fluorescent dyes and can be bound to the specimen, into a specimen sample containing a specimen and measuring the fluorescence emitted by the specimen sample.

BACKGROUND ART

For methods for detecting and quantifying DNAs or RNAs having specified base sequences present in samples, methods utilizing "detection probes" that specifically hybridize to DNAs or RNAs, which are the subject of detection, are widely in use. Oligonucleotide nucleic acids having base sequences complementary to parts of the base sequences for DNAs or RNAs (target nucleic acids), which are the subject of detection, are frequently used as detection probes.

In these methods, after hybrids between detection probes and target nucleic acids have been formed, any changes resulting from the formation of the hybrids are detected, thereby confirming that the target nucleic acids to be the subject of detection are contained in samples and quantifying their contents. For example, a detection probe is labeled with a fluorescent dye. This fluorescent labeled detection probe(fluorescent labeled oligonucleotide nucleic acid) is added to a sample. If a target nucleic acid is present in the sample, the fluorescent labeled detection probe binds to the target nucleic acid to form a hybrid. Then, a manipulation is performed to separate the fluorescent labeled detection probe that does not bind from the fluorescent labeled detection probe that has been hybridized to the target nucleic acid in the sample, thereby removing the fluorescent labeled detection probe that does not bind in the sample. Here, if the fluorescence intensity of the sample is measured, it will enable the amount of the target nucleic acid in the sample to be quantified.

The above-described method needs a manipulation for removing the detection probe that does not bind to the target nucleic acid after the detection probe has been added to the sample. Because such a manipulation for separation is complicated in practice, a variety of assays that do not require manipulations for separating non-bound probes from bound probes after addition of probes have been attempted (homogeneous assays).

One of the homogeneous assays is a method that utilizes resonance energy transfer occurring between two kinds of fluorescent molecules. Generally, when two kinds of fluorescent molecules are within a distance of about 70–80 angstroms, interaction between the fluorescent molecules occurs(resonance energy transfer) and thus their fluorescence spectrum or fluorescence decay curve changes. In a fluorescence spectrum, the fluorescence intensity resulting from a donor (in general between the two kinds of fluorescent molecules, the molecule whose absorption spectrum is on the shorter wavelength side) decreases, whereas the fluorescence intensity resulting from an acceptor (between the two kinds of fluorescent molecules, the molecule whose absorption is on the longer wavelength side) increases. Also, with respect to changes in the fluorescence decay curve after pulse-excitation, decay for the donor accelerates, whereas decay for the acceptor delays.

Some attempts are made to utilize this resonance energy transfer between fluorescent molecules in the homogeneous assays for nucleic acids. Specifically, two kinds of fluorescent labeled detection probes(those individually labeled with different kinds of fluorescent dye molecules) are provided and these hybridize to a target nucleic acid adjacently with each other. The energy transfer occurs to cause changes in the fluorescence spectrum, because the two kinds of fluorescent dyes are within a close distance in a hybrid. Namely, the fluorescence spectrum changes as a result of the formation of the hybrid comprising the two kinds of fluorescent labeled detection probes and the target nucleic acid, which will enable the detection of the target nucleic acid by measuring the change in the fluorescence spectrum (Cardullo, R. A., et al. (1988) Proc. Natl. Acad. Sci. USA. 85, 8790–8794, EP0070685). U.S. Pat. No. 4,996,143 discloses oligonucleotide probes labeled with fluorescence dyes suited for methods of detecting target nucleic acids based on measurement of changes in fluorescence spectra.

Accordingly, the method to measure any change in a fluorescence spectrum caused by the energy transfer is useful for the homogeneous assays of nucleic acids. However, if the amount of detection probes in a sample (the number of their molecules) exceeds that of a target nucleic acid (the number of its molecules), practically it becomes very difficult to use the above-described method for detecting a target nucleic acid based on changes in a fluorescence spectrum. Namely, the fluorescence spectrum to be measured is the sum of a fluorescence spectrum resulting from a small number of fluorescent dye molecules that has undergone the energy transfer and a fluorescence spectrum resulting from a large number of fluorescent dye molecules that has not undergone the energy transfer. Thus, the fluorescence spectrum resulting from the small number of fluorescent dye molecules that has undergone the energy transfer is buried in the fluorescence spectrum resulting from the large number of fluorescent dye molecules that has not undergone the energy transfer, which makes it practically impossible to detect any changes in the fluorescence spectrum caused by the energy transfer.

It quite often happens in the actual measurement of biological samples that the amounts of detection probes exceed those of nucleic acids (target nucleic acids), which are the subject of detection. One such example is that the amount of a target nucleic acid in a sample is unknown. Also, the concentrations of detection probes in samples can not be lowered below certain levels, because sensitivity in measurement depends on the fluorescence intensities of the samples. Thus, when the amounts of the target nucleic acids are very small (low concentrations), the amounts of the detection probes exceed those of the target nucleic acids.

Accordingly, there is a need for the method that will allow the highly accurate detection of a nucleic acid, which is the subject of detection, even under the conditions where detection probes are present in excess relative to a nucleic acid, which is the subject of detection.

In general, among methods for detecting and measuring energy transfer between fluorescent molecules, there are a method to measure any changes in a fluorescence spectrum and a method to measure any changes in the decay curve of fluorescence intensities after pulse excitation (time-resolution method). Where fluorescent molecules that have undergone the energy transfer and the same kind of fluorescent molecules that have not undergone the energy transfer coexist, it often happens that the method to measure a fluorescence decay curve (time-resolved measurement ) is more advantageous than the method to measure changes in a fluorescence spectrum Morrison, L. E. (1998) Anal.Biochem. 174 101–120; Japanese Laid-Open Patent Application Hei 7-229835). The fluorescence decay of an acceptor delays due to the energy transfer. Morrison disclosed that when the delay in decay is sufficiently large, it is possible to selectively measure the fluorescence resulting from the acceptor excited by the energy transfer by measuring fluorescence intensities in a time zone after the fluorescence decay resulting from the acceptor directly excited is substantially complete. In Japanese Laid-Open Patent Application Hei 7-229835, there is provided a method for calibrating errors in detection that are caused by mixing of fluorescence resulting from a donor into the fluorescence wavelength region of an acceptor, said method measuring fluorescence decay in the fluorescence wavelength of the donor in addition to fluorescence decay in the fluorescence wavelength region of the acceptor.

Furthermore, in Japanese Laid-Open Patent Application Hei 7-229835 it is stated that if the method of Hei 7-229835 (a method to detect energy transfer between fluorescent molecules through time-resolved measurement) is applied to a homogeneous assay of nucleic acids, the detection of a target nucleic acid is feasible even under the conditions where detection probes are present in excess relative to a target nucleic acid. However, there is no mention of the requirements that the detection probes to be used in said method should satisfy.

DISCLOSURE OF INVENTION

This invention relates to the fluorescent labeled detection probes wherein the fluorescence decay of a fluorescent dye as an acceptor is sufficiently delayed when two kinds of detection probes labeled with fluorescent dyes are hybridized to the same specimen (target nucleic acid) adjacently with each other to form a hybrid and energy transfer occurs between the two kinds of fluorescent dye molecules.

This invention also provides a method for detecting a target nucleic acid with high sensitivity by the use of said probes. This has enabled the detection of the target nucleic acid with high sensitivity and great accuracy under the conditions where the detection probes are present in excess relative to the target nucleic acid.

In order to be able to detect a target nucleic acid with high sensitivity under the conditions where detection probes are present in excess relative to the target nucleic acid by utilizing the energy transfer, it was thought that the fluorescence decay of an acceptor which forms a hybrid with a detection probe labeled with a donor fluorescent dye and a target nucleic acid and is excited by the energy transfer needs to be delayed to a large extent as compared with the fluorescence decay of an acceptor excited directly.

It was discovered that in the hybrid formed from the two kinds of fluorescent labeled detection probes and the target nucleic acid, the magnitude of the delay in the fluorescence decay of the acceptor excited by the energy transfer largely depended on the following factors: (1) the base number between the two nucleotides, one of which is conjugated with the donor fluorescent dye molecule on the one detection probe and the other of which is conjugated with acceptor flourescent dye molecule on the other detection probe (which defines the mean distance between the two fluorescent dye molecules); (2) the structure of spacing (double-stranded or single-stranded) between the two nucleotides, one of which is conjugated with the donor fluorescent dye molecule on the one detection probe and the other of which is conjugated with acceptor flourescent dye molecule on the other detection probe; (3) the positions of the nucleotides, which the fluorescent dye molecules were conjugated with, on the detection probes; and (4) the kinds of the fluorescent dye molecules. Based on these findings for detection probes, a combination of suitable fluorescent dyes was chosen, the base number was selected so that the distance between the two kinds of fluorescent dye molecules could be appropriate at formation of a hybrid, and the structure between the two nucleotides to which the fluorescent dye molecules bound in a hybrid was appropriately set. This successfully led to the discoveries of a method and detection probes that will enable the detection of a target nucleic acid with high sensitivity in a sample where the detection probes are present in excess relative to the target nucleic acid.

The requirements for detection probes used to detect energy transfer through measurement of changes in a fluorescence decay curve (according to this invention) greatly differs from those for detection probes used to detect the energy transfer through measurement of changes in a fluorescence spectrum (as disclosed in U.S. Pat. No. 4,996,143).

The amounts of changes in a fluorescence spectrum (decreasing quantity of fluorescence resulting from of a donor and increasing quantity of fluorescence resulting from an acceptor) become greater as energy transfer efficiency increases. The energy transfer efficiency is in inverse proportion to the sixth power of the distance between a donor and an acceptor; therefore, to accurately detect the energy transfer based on the changes in the fluorescence spectrum, the distance between the donor and the acceptor is desirably made as close as possible in an actual sample. U.S. Pat. No. 4,996,143 describes that the distance (base number) between a donor dye and an acceptor dye which substantially makes the detection of the energy transfer possible is "two to seven bases" and that the smaller the base number is, the better the detection. By contrast, it was realized that a median degree of the energy transfer efficiency (on the order of 50%) is most desirable when the energy transfer is detected by the measurement of delays in the fluorescence decay curve of an acceptor. As the energy transfer efficiency becomes higher, the quantity of fluorescence from the acceptor increases, whereas the delay in the fluorescence decay of the acceptor grows smaller. The increase in the quantity of fluorescence facilitates the detection of a change in the decay curve, but the smaller delay in decay renders the detection of the change difficult. In view of these two contradicting factors, either of too high energy transfer efficiency and too low efficiency is unsuitable for the detection of a specimen. In other words, for the purpose of detection of a specimen the distance (base number) between the donor dye and the acceptor dye at the time of hybrid formation is most desirably that which brings a median degree of the energy transfer efficiency (as will be described later, see FIG. 2). For example, when a combination of Bodipy 493/503 (donor) and Cy5 (acceptor.) was used as fluorescent dyes, this distance proved to be "from 10 to 12 bases" in terms of the base number in a hybrid: in the case where the spacing between the two nucleotides to which the dyes bind in the hybrid adopts a double-stranded structure, as will be described later.

Also, in few instances the distance between a donor dye and an acceptor dye is fixed in an actual sample, and it frequently fluctuates with time. Such fluctuations in the distance between the donor dye and the acceptor dye are caused by movement of the dye molecules or the like and their magnitude or speed greatly differs depending on the structure of a hybrid. Because the amount of a change in a fluorescence spectrum caused by the formation of the hybrid is determined by the mean distance (mean energy transfer efficiency) between a donor and an acceptor in the hybrid, thus far there has been little necessity for giving consideration to the magnitude of fluctuations in the distance between the dyes in the hybrid formed when the properties of detection probes were investigated. By contrast, a fluorescence decay curve generally depends on fluctuations of the distance between two dyes and their distribution. In reality, the fluorescence decay curve of fluorescent dye molecules on detection probes having formed a hybrid was found to heavily depend on the boundary of movement of the dye molecules defined by the structure of the hybrid. Consequently, it has become clear that to design detection probes such that in the hybrid the spacing between the two nucleotides to which the fluorescent dyes bind adopts a double-stranded structure throughout and to locate the labeling position of one of the fluorescent dyes at a termini of the oligonucleotide are most desirable for the purpose of detection of a specimen.

This invention relates to the finding of detection probes that are suited for the detection of a specimen by time-resolved measurement of the energy transfer (i.e., a method to measure changes in a fluorescence decay curve) with a view to enabling the detection with great accuracy, of a specimen under the conditions where the detection probes are in large excess in the specimen.

Specifically, this invention provides:
a pair of detection probes for detecting a specimen having a specified polynucleotide base sequence, said pair of detection probes comprising:
    a donor probe to which a first fluorescent dye molecule binds, having a base sequence capable of hybridizing with a part of the polynucleotide base sequence; and
    an acceptor probe to which a second fluorescent dye molecule binds, having a base sequence capable of hybridizing with a part of the polynucleotide base sequence,
    wherein a fluorescence decay curve resulting from the donor probe and the acceptor probe significantly changes when a hybrid among the donor probe, the acceptor probe, and the specimen is formed.

Also, the invention provides the detection probes as described above, wherein spacing between a nucleotide to which the first fluorescent molecule of the donor probe binds and a nucleotide to which the second fluorescent molecule of the acceptor probe binds is a double-stranded structure in the hybrid.

Also, the invention provides the detection probes as described above, wherein the donor probe and the acceptor probe are hybridized to the specimen sequentially and adjacently in the hybrid.

Also, the invention provides the detection probes as described above, wherein either the first fluorescent dye molecule or the second fluorescent dye molecule is a terminal part at a side on which the pair of detection probes sequentially hybridizing on the specimen are adjacent with each other.

Also, the invention provides the detection probes as described above, wherein the donor probe and the acceptor probe are hybridized to the specimen and a part of spacing between a nucleotide to which the first fluorescent dye molecule binds and a nucleotide to which the second fluorescent dye molecule binds adopts a double-stranded structure in the hybrid formed from the pair of detection probes and the specimen.

Also, the invention provides the detection probes as described above, wherein a base number between a nucleotide to which the first fluorescent dye molecule binds and a nucleotide to which the second fluorescent dye molecule binds is from 4 to 20 in the hybrid.

Also, the invention provides the detection probes as described above, wherein a base number between a nucleotide to which the first fluorescent dye molecule binds and a nucleotide to which the second fluorescent dye molecule binds is from 8 to 16 in the hybrid.

Also, the invention provides the detection probes as described above, wherein the first fluorescent dye molecule has either a fluorophore of a 4,4-difluoro-4-boro-3a,4a-diaza-s-indacene type or a fluorophore of a fluorescein type, and the second fluorescent dye molecule has either a fluorophore of an Indocyanine type or a fluorophore of a Rhodamine type.

Also, the invention provides the detection probes as described above, wherein the first fluorescent dye molecule has a fluorophore of a 4,4-difluoro-4-boro-3a,4a-diaza-s-indacene type and the second fluorescent dye molecule has a fluorophore of an Indocyanine type.

Further, this invention provides a method for detecting a specimen having a specified polynucleotide base sequence, said method comprising:
    (1) the first step of forming a hybrid from the specimen and a pair of detection probes, said pair of detection probe comprising:
        a donor probe to which a first fluorescent dye molecule binds, having a base sequence capable of hybridizing with a part of the polynucleotide base sequence; and
        an acceptor probe to which a second fluorescent dye molecule binds, having a base sequence capable of hybridizing with a part of the polynucleotide base sequence;
    (2) the second step of measuring a decay curve of fluorescence intensities for the hybrid in a wavelength region of fluorescence resulting from the second fluorescent dye;
    (3) the third step of measuring a decay curve of fluorescence intensities for the pair of detection probes in a wavelength region of fluorescence resulting from the second fluorescent dye; and
    (4) the fourth step of detecting the presence of the polynucleotide base sequence based on a comparison between the fluorescence decay curve obtained in the second step and the fluorescence decay curve obtained in the third step.

Also, the invention provides the method for detecting a specimen having a specified polynucleotide base sequence as described above, wherein spacing between a nucleotide to which the first fluorescent dye molecule of the donor probe binds and a nucleotide to which the second fluorescent dye molecule of the acceptor probe binds is a double-stranded structure in the hybrid.

Also, the invention provides the method for detecting a specimen having a specified polynucleotide base sequence as described above, wherein the donor probe and the acceptor probe hybridize to the specimen sequentially and adjacently in the hybrid.

Also, the invention provides the method for detecting a specimen having a specified polynucleotide base sequence as described above, wherein either the first fluorescent dye molecule or the second fluorescent dye molecule is a terminal part at a side on which the pair of detection probes sequentially hybridizing on the specimen are adjacent with each other.

Also, the invention provides the method for detecting a specimen having a specified polynucleotide base sequence as described above, wherein the donor probe and the acceptor probe hybridize to the specimen and a part of spacing between a nucleotide to which the first fluorescent dye molecule binds and a nucleotide to which the second fluorescent dye molecule binds adopts a double-stranded structure in the hybrid formed from the pair of detection probes and the specimen.

Also, the invention provides the method for detecting a specimen having a specified polynucleotide base sequence as described above, wherein a base number between a nucleotide to which the first fluorescent dye molecule binds and a nucleotide to which the second fluorescent dye molecule binds is from 4 to 20 in the hybrid.

Also, the invention provides the method for detecting a specimen having a specified polynucleotide base sequence as described above, wherein a base number between a nucleotide to which the first fluorescent dye molecule binds and a nucleotide to which the second fluorescent dye molecule binds is from 8 to 16 in the hybrid.

Also, the invention provides the method for detecting a specimen having a specified polynucleotide base sequence as described above, wherein the first fluorescent dye molecule has either a fluorophore of a 4,4-difluoro-4-boro-3a,4a-diaza-s-indacene type or a fluorophore of a fluorescein type and the second fluorescent dye molecule has either a fluorophore of an Indocyanine type or a fluorophore of a Rhodamine type.

Also, the invention provides the method for detecting a specimen having a specified polynucleotide base sequence as described above, wherein the first fluorescent dye molecule has a fluorophore of a 4,4-difluoro-4-boro-3a,4a-diaza-s-indacene type and the second fluorescent dye molecule has a fluorophore of an Indocyanine type.

BRIEF DESCRIPTION OF DRAWINGS

FIG. 6A is a schematic diagram illustrating one of the examples where detection probes and method of detection by the use of the probes according to the invention are applied, indicating that they can be used to detect any change by which a different DNA fragment is incorporated into a specified site of DNA during alternations of the primary structure of a nucleic acid.

FIG. 6B is a schematic diagram illustrating one of the examples where detection probes and method of detection by the use of the probes according to the invention are applied, indicating that they can be used to detect any change by which a different DNA fragment is incorporated into a specified site of DNA during alternations of the primary structure of a nucleic acid.

FIG. 38 shows the fluorescence decay curves in the fluorescence wavelength region of an acceptor when a pair of detection probes (S-oligo labeled with fluorescent dye molecules) was mixed with a target RNA to be the specimen in such varying proportions as to render the probes excessive. The detection probes used are as follows: the donor fluorescent dye is Bodipy 493/503 and the acceptor fluorescent dye is Cy5; at the time of hybrid formation the spacing between the nucleotide to which the donor fluorescent dye bind and the nucleotide to which the acceptor fluorescent dye bind is double-stranded; and the base number for the spacing is 10 (n=10). The proportions of the target RNA to the probes are: (1) 0%, (2) 2.5%, (3) 5%, and (4) 20% (target RNA/probe, molar ratio).

BEST MODE FOR CARRYING OUT THE INVENTION

Specimens

Figure 1A:
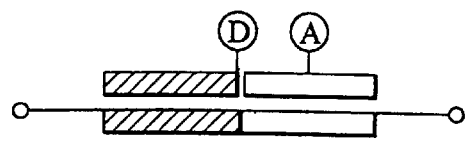
FIG. 1A illustrates one of several embodiments of detection probes according to this invention where in a hybrid, the spacing between the two nucleotides to which fluorescent dye molecules bind adopts a double-stranded structure and one of the fluorescent dye molecules is labeled (or bound) at a terminal part facing the adjacent part of the other probe. In the figure the positions of the donor and acceptor dyes are mutually interchangeable.
Figure 1B:
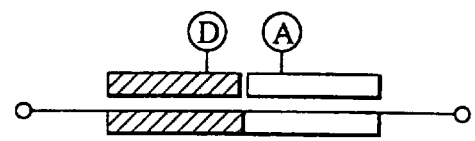
FIG. 1B illustrates one of several embodiments of detection probes according to the invention where in a hybrid, the spacing between two nucleotides to which fluorescent dye molecules bind adopts a double-stranded structure and both of the fluorescent dye molecules are labeled (or bound) at middle parts of the respective probes. In the figure the positions of the donor and acceptor dyes are mutually interchangeable.
Figure 1C:
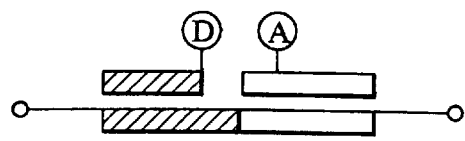
FIG. 1C illustrates one of several embodiments of detection probes according to the invention where in a hybrid, the spacing between two nucleotides to which fluorescent dye molecules bind is partially a double-stranded structure, one of the fluorescent dye molecules is labeled at a terminal part facing the adjacent part of the other probe and the other fluorescent dye molecule is labeled at a middle part of said probe. In the figure the positions of the donor and acceptor dyes are mutually interchangeable.
Figure 1D:
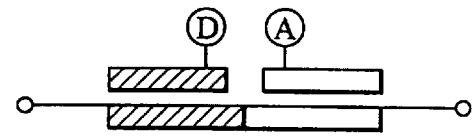
FIG. 1D illustrates one of several embodiments of detection probes according to the invention where in a hybrid, the spacing between two nucleotides to which fluorescent dye molecules bind is partially a double-stranded structure and both of the fluorescent dye molecules are labeled at middle parts of the respective probes. In the figure the positions of the donor and acceptor dyes are mutually interchangeable.
Figure 1E:
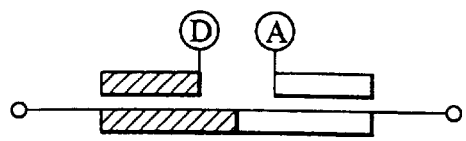
FIG. 1E illustrates one of several embodiments of detection probes according to the invention where in a hybrid, the spacing between two nucleotides to which fluorescent dye molecules bind is a single-stranded structure and both of the fluorescent dye molecules are labeled at terminal parts of the respective probes facing the adjacent parts of the other probes. In the figure the positions of the donor and acceptor dyes are mutually interchangeable.
Figure 1F:
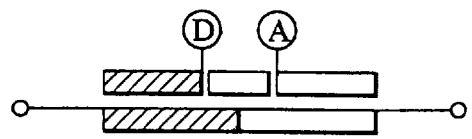
FIG. 1F illustrates one of several embodiments of detection probes according to the invention where in a hybrid, a third probe (not labeled with fluorescence) is introduced into the hybrid so that the spacing between the two nucleotides to which fluorescent dye molecules bind may adopt a double-stranded structure. In the figure the positions of the donor and acceptor dyes are mutually interchangeable.
Figure 2:
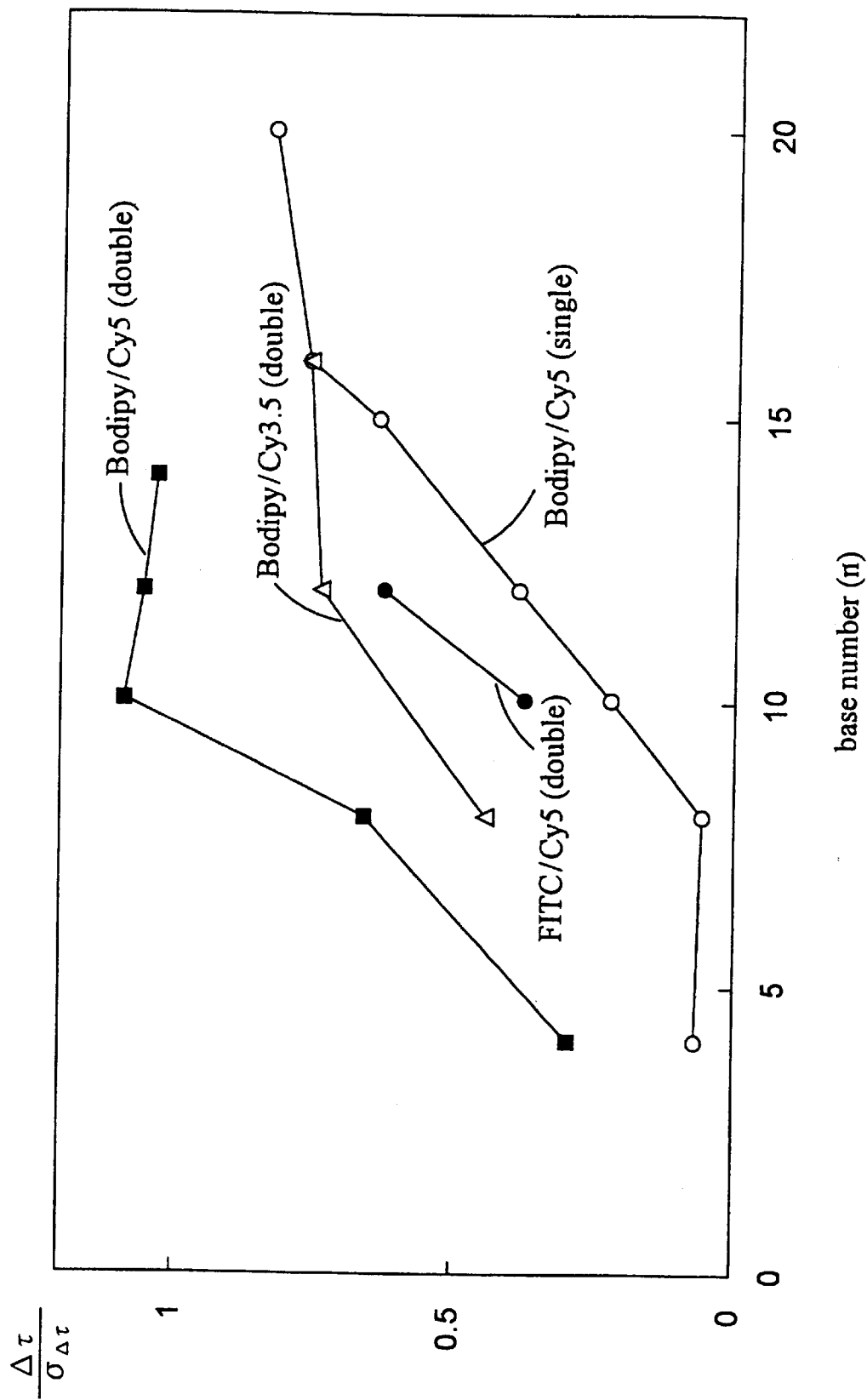
FIG. 2 is a graph illustrating a comparison of accuracy in detecting a specimen (target nucleic acid) by various detection probes according to the invention. In the detection probes the following factors are varied: (1) the kinds of combination of fluorescent dye molecules; (2) whether the spacing between the two nucleotides to which the fluorescent dye molecules bind in a hybrid is made single-stranded or double-stranded; (3) the base number between the two nucleotides to which the fluorescent dye molecules bind in the hybrid (abscissa in the figure). Employing these detection probes, changes in fluorescence decay curves in the fluorescence wavelength region of the acceptors caused by the formation of hybrids with the specimen were measured. The ordinate in the figure ($\Delta\tau/\sigma_{\Delta\tau}$) is a parameter comparatively representing S/N to distinguish fluorescence decay curves in the presence of the specimen from those in the absence of the specimen.

Specimens to be detected by the detection probes and method of detection according to this invention are not particularly limited with respect to their kinds, structures, length, etc. and include ordinary nucleic acids and nucleic acid analogs. For example, DNA, RNA, synthetic oligonucleotides, synthetic polynucleotides, and the like are named. The specimen also includes that which possesses in its part a structure having a specified base sequence to which the detection probes according to the invention bind substantially in a specific manner. Here, the specimen does not need to possess a nucleic acid structure throughout. Therefore, in employing the method of detection according to the invention, it is not required that all the base sequences of nucleic acid or nucleic acid analog of the specimen be known, and only the base sequence of its specified portion that allows the specific binding by the detection probes according to the invention be known. Methods for base sequence determination known in the art may be used to find out the base sequence of the above-mentioned specified portion in the specimen.

Detection Probes

For the detection probes according to this invention, two fluorescent labeled oligonucleotides that are labeled with different types of fluorescent dye molecules are to be used as a pair.

Nucleic acid portions comprising the backbone of the detection probes are not limited to DNA or RNA and may be various nucleic acid analogs that are commonly used. For example, among others those in which phosphoric ester portions are converted to phosphorothioates (S-oligo) and those in which they are converted to methylphosphonates (M-oligo) are named. Those in which amide, sulfoamide, ethyleneglycol, and thioformal substitute phosphodiester bonds are also named. Those in which sugars are modified may also be used. For example, they include the ones in which 2'-position of a ribose is modified by 2'-O-alkyl, 2'-O-allyl, 2'-halogen, and 2'-amino. Polyamidonucleic acids (PNA) may also be used.

There is no particular limitation to the base number of each probe. It suffices if the following conditions are satisfied: the formation of a stable hybrid with a target nucLeic acid that is a specimen; and low probability of forming hybrids through erroneous recognition of nucleic acids other than the specimen. For this purpose, usually more than 10 bases are enough and more than 15 bases are preferable. The total base number of the two probes is also not particularly limited. It suffices if the two probes are both able to hybridize with the specified base sequence site of a target nucleic acid of the specimen. Usually it is more than 20 bases and preferably more than 30 bases.

The base sequence of the probe according to this invention may be the one that is complementary to the base sequence of the specified site in the specimen at which the detection probes bind to (or hybridize with) the specimen. Here, as long as the detection probes substantially hybridize with the specified site of the specimen as described above, parts of the base sequences of the detection probes do not need to have complementation to the base sequence of the specified site of the specimen as described above.

The probes according to the invention are those which show large delays in the fluorescence decay of an acceptor fluorescent dye at the time of forming a hybrid with a target nucleic acid to be the specimen. To this end, in the probes according to the invention the following factors are appropriately set: the combination of fluorescent dyes; the base number between the nucleotides to which the fluorescent dye molecules bind in the hybrid; whether the spacing between the nucleotides to which the fluorescent dye molecules bind in the hybrid is single-stranded or double-stranded; and the positions of the fluorescent dye molecules in the hybrid.

Generally, where each of donor and acceptor dyes is singly present, decay of the fluorescence intensities of each dye when the dye is pulse-excited is represented by a single exponential function decaying with the time constant (fluorescence lifetime) pertaining to each dye molecule (eqs (1) and (2)).

The fluorescence decay curve of a donor when the donor is singly present (or when no energy transfer between the donor and an acceptor is occurring):

$$I_d(t)=\exp(-t/\tau_d), \tau_d\text{:fluorescence lifetime of donor} \quad (\text{eq 1})$$

The fluorescence decay curve of an acceptor when the acceptor is singly present (or when no energy transfer between a donor and the acceptor is occurring):

$$I_a(t)=\exp(-t/\tau_a), \tau_a\text{:fluorescence lifetime of acceptor} \quad (\text{eq 2})$$

If resonance energy transfer occurs between a donor and an acceptor, fluorescence decay of the donor accelerates and that of the acceptor delays. When the distance between a donor molecule and an acceptor molecule is supposed to be fixed, the fluorescence decay curve of the donor is represented by eq (3). Here, fluorescence lifetime $\tau_{da}$ is defined by efficiency E of the energy transfer. Namely, the higher the energy transfer efficiency becomes, the more fluorescence decay of the donor accelerates.

The fluorescence decay curve of a donor undergoing the energy transfer:

$$I'_d(t)=\exp(-t/\tau_{da}) \quad (\text{eq 3})$$

$$\tau_{da}=\tau_d(1-E)$$

On the other hand, the fluorescence decay curve of an acceptor is represented by eq (4). This decay curve is not a single exponential function.

The fluorescence decay curve of an acceptor excited by the energy transfer:

$$I'_a(t)=\int_0^t \exp\left(-\frac{(t-\tau)}{\tau_{da}}\right)\cdot\exp(-\tau/\tau_a)d\tau \quad (\text{eq 4})$$

As described above, eqs (3) and (4) represent the fluorescence decay curves when the distance between the donor molecule and the acceptor molecule is supposed to be fixed. If the distance between the donor and the acceptor is not fixed and fluctuates, the fluorescence lifetime of the donor during its energy transfer in eqs (3) and (4) is not a constant, but incorporates a function expressing distribution of the distance between the donor and the acceptor due to the fluctuations.

By measuring energy transfer between two fluorescent dye molecules according to a time-resolution method, a target nucleic acid is to be detected under the conditions where detection probes are present in excess relative to the target nucleic acid: for this purpose, it is necessary to enlarge the difference between the fluorescence decay curve represented by eq (4) and the fluorescence decay curve represented by eq (2). The fluorescence decay curve of eq (4) is defined by fluorescence lifetime of the donor, fluorescence lifetime of the acceptor, the energy transfer efficiency and fluctuations in the distance between the donor and the acceptor, while the fluorescence decay curve of eq (2) is defined by lifetime of the acceptor.

Accordingly, the combination of fluorescent dyes, the mean distance between two fluorescent dye molecules in a hybrid (which principally defines the energy transfer efficiency), and the magnitude of its fluctuations may be set in a mutually appropriate manner.

In addition, the combination of the fluorescent dyes desirably satisfy the following conditions:

and the structures and length of linkers between the fluorescent dye molecules and the oligonucleotides.

Table 1, on the basis of Examples, summarizes the cases in which delays in the fluorescence decay curves in the fluorescence wavelength region of acceptors were observed for hybrids between a variety of fluorescent labeled probes and a target DNA. The variety of fluorescent labeled probes were prepared and each one pair of the probes was mixed with the target DNA to form a hybrid. The hybrid was separated with a high performance liquid column chromatogram and its fluorescence spectrum and fluorescence decay curve were measured. With respect to the pair of probes, its fluorescence spectrum and fluorescence decay curve were measured in a sample containing no target DNA, and changes in the fluorescence spectra as well as in the fluorescence decay curves (delays) resulting from the formation of the hybrid were observed. See Examples for details.

TABLE 1

| Combination of fluorescent dyes donor/acceptor | Oligonucleotide Structure between the donor fluorescent dye and the acceptor fluorescent dye in the hybrid | base number (n) between the donor fluorescent dye and the acceptor fluorescent dye in the hybrid | changes in fluorescence spectrum | delays in fluorescence decay in fluorescence wavelength region of acceptor |
|---|---|---|---|---|
| BODIPY/Cy5 | single-stranded | 4, 8, 10, 12, 15, 20 | + | +++ |
|  | double-stranded | 4, 8, 10, 12, 14 | + | ++++ |
| BODIPY/Cy3.5 | double-stranded | 8, 12, 16 | + | ++ |
| FITC/Cy5 | single-stranded | 12, 15, 20 | + | + |
|  | double-stranded | 10, 12 | + | ++ |
| FITC/Cy3 | single-stranded | 12, 15, 20 | + | − |
|  | double-stranded | 10, 13, 15 | + | + |
|  | single-stranded | 4, 8, 12, 15, 20 | + | − |
|  | double-stranded | 15 | + | + |

1. The fluorescence lifetime of a donor is longer than that of an acceptor and its difference is large.

2. The probability of an acceptor's being excited at the excitation wavelength of a donor is low (i.e., the molecular absorption coefficient of the donor at its absorption maximum>>the molecular absorption coefficient of the acceptor at the wavelength of the donor's absorption maximum).

3. The overlap between the fluorescence spectrum of a donor and the fluorescence spectrum of an acceptor is small (i.e., mixing of the fluorescence of the donor into the fluorescence wavelength region of the acceptor is small).

The combination of fluorescent dyes that satisfy the above-mentioned conditions is, for example, the one in which a Bodipy (4,4-difluoro-4-boro-3a,4a-diaza-s-indacene) type dye or fluorescein type dye is used as the donor dye and this is combined an Indocyanine type dye or Rhodamine type dye as the acceptor dye.

The mean distance between two fluorescent dye molecules in a hybrid is determined by the base number between the nucleotides to which the two fluorescent dye molecules bind in the hybrid. It is also supposed that the magnitude of fluctuations in the distance between the fluorescent dye molecules is determined by the following factors among others: whether the spacing between the nucleotides to which the two fluorescent dye molecules bind is a single-stranded structure or double-stranded structure (see FIG. 1); the positions of the fluorescent dye molecules in the hybrid;

"Bodipy" is a trademark of Molecular Probes Inc. (Eugene, Oreg., USA). Also, unless otherwise stated, "Bodipy" in Examples is "Bodipy 493/503." Cy3, Cy3.5, and Cy5 are trademarks of Amersham Inc.

For all the kinds of detection probes used, changes in fluorescence spectra resulting from the formation of hybrids were observed. This indicates that energy transfer occurs through the hybrid formation. In reference to the magnitude of delays in fluorescence decay curves in the wavelength region of acceptors, large differences depending on the kinds of detection probes were noted. In the item "delays in fluorescence decay in the fluorescence wavelength of acceptor" in Table 1, "++++" means that an extremely large delay is caused in the fluorescence decay, "+++" means that a large delay is caused in the fluorescence decay, "++" means that a delay is caused in the fluorescence decay, and "+" means that a delay is noted in the fluorescence decay. "−" means that no delay is noted in the fluorescence decay.

Bodipy/Cy5 is most preferable for the combination of fluorescent dyes, and Bodipy/Cy3.5 and FITC/Cy5 follow in this order. Combinations of FITC/Cy3 and FITC/Rhodamine are usable when the spacing between fluorescent dye molecules in the hybrid is made double-stranded. Bodipy is superior to FITC as a donor dye: it is thought to be mainly ascribable to the fact that the difference between fluorescence lifetime of the donor and fluorescence lifetime of the acceptor (Cy5, about one ns; Rhodamine, about three ns) grows larger because the fluorescence lifetime of Bodipy (about seven ns) is longer than that of FITC (about four ns). When the combination that would not allow good separation of the fluorescence spectrum of the donor from that of the acceptor was used, a delay in the fluorescence decay was caused in the case where the spacing between the fluorescent dyes in the hybrid was made double-stranded, whereas no delay in the fluorescence decay was noted in the case where the spacing was made single-stranded.

As is evident from Table 1, it is understood that where the spacing between the fluorescent dyes in the hybrid is made double-stranded, a larger delay is caused in the fluorescence decay compared with the single-stranded spacing. It is thought that when the spacing between the nucleotides to which the two fluorescent dyes bind is a single-stranded structure in the hybrid, the relative spatial positions of the donor and acceptor dyes fluctuate greatly because the freedom of molecular motion for the portion being single-stranded is large. Namely, the distance between the two dyes fluctuates with time. On the other hand, in the case of a double-stranded structure because the freedom of molecular motion for that portion is far more restricted than a single-stranded structure, the fluctuations and distribution of the distance between the donor dye and the acceptor dye are small. The results in Examples indicate that where fluctuations in the distance between the donor dye and the acceptor dye are small; that is to say, the structure between the two fluorescent dyes is made double-stranded, a large delay is caused in the fluorescence decay.

As is shown in the foregoing and Examples, a variety of the pair of detection probes labeled with fluorescence that cause large delays in the fluorescence decay resulting from the formation of hybrids with a target nucleic acid do exist. When these probes were used, accuracy in the detection of changes in the fluorescence decay curves resulting from the hybrid formation was quantitatively compared: to this end an analysis as described below was conducted.

With the formation of a hybrid (due to energy transfer), the fluorescence of an acceptor increases but its increments vary from one probe to another (because they depend on the energy transfer efficiency). Thus, the accuracy to identify changes in the fluorescence decay curve resulting from the formation of the hybrid is determined by the magnitude of the changes in the decay curve and variations in the quantity of fluorescence.

S/N (signal-to-noise ratio) distinguishing the fluorescence decay curve of probes that had formed a hybrid from that of probes that had not formed a hybrid was used as an index to evaluate each pair of probes.

The S/N distinguishing the two fluorescence decay curves was computed according to the following procedure (S. A. Soper, B. L. Legender, and D. C. Williams (1995) Analy. Chem. 67, 4358–4365 was consulted).

First, with respect to each of the fluorescence decay curve of probes forming a hybrid and the fluorescence decay curve of probes not forming a hybrid (i.e., a sample containing no target nucleic acid), the rate of decay was computed according to the following equation using a time zone of from three ns to seven ns after irradiation with pulse-excitation light:

$$\tau = -\Delta t/(\ln(D_1/D_0))$$

$D_0$: quantity of fluorescence in a time zone of 3–5 ns
$D_1$: quantity of fluorescence in a time zone of 5–7 ns
$\Delta t = 2$ ns Also, the magnitude of scatters ($\sigma$) of data was computed according to the following equation:

$$\sigma = \tau \times (-\ln(D_1/D_0))/(1/D_0 + 1/D_1)^{1/2}$$

$\sigma$ is the standard deviation of data distribution when the measurement was performed many times under the same conditions and takes smaller values as the quantity of fluorescence increases: with increasing fluorescence quantities the scattering of data becomes smaller.

S/N (signal-to-noise ratio) distinguishing the fluorescence decay curve of probes forming a hybrid from that of probes not forming a hybrid is expressed by $\Delta\tau/\sigma_{\Delta\tau}$, which is obtained by dividing the sum of scatters of the data ($\sigma_{\Delta\tau}$) by the differential fluorescence lifetime ($\Delta\tau$).

Figure 3:
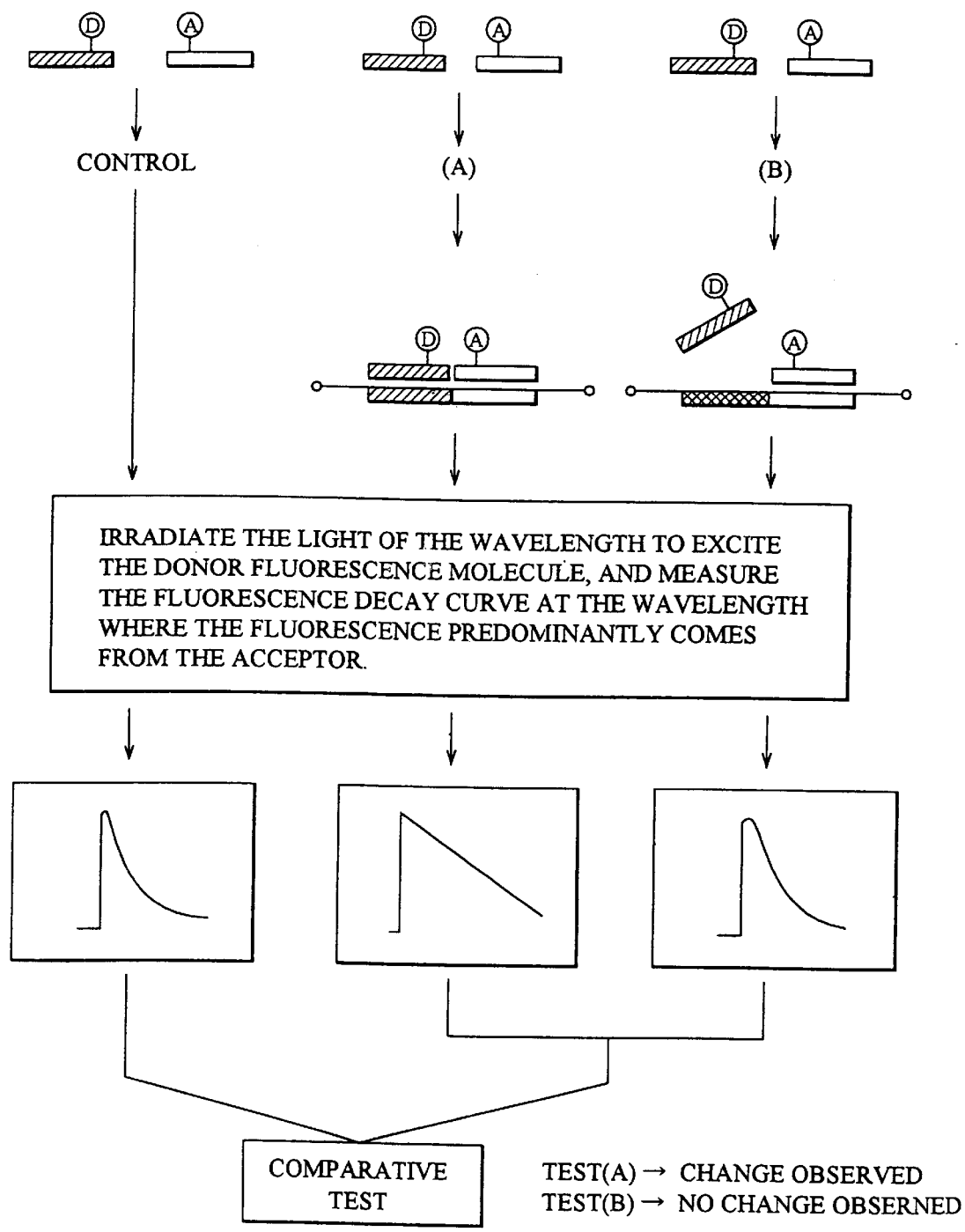
FIG. 3 is a schematic diagram illustrating detection of the presence of a specimen by using detection probes and method of detection according to the invention.

Here, $\Delta\tau = \tau(\text{hybrid}) - \tau(\text{probe})$, $\sigma_{\Delta\tau} = (\sigma(\text{hybrid})^2 + \sigma(\text{probe})^2)^{1/2}$ Table 2 and FIG. 3 show the results: $\Delta\tau/\sigma_{\Delta\tau}$ values in Table 2 and FIG. 3 are in relative units.

TABLE 2

BODIPY/CY5 (double-stranded)

| | n = 4 | n = 8 | n = 10 | n = 12 | n = 14 | |
|---|---|---|---|---|---|---|
| $\Delta\tau/\sigma_{\Delta\tau}$ | 0.292 | 0.657 | 1.081 | 1.051 | 1.026 | |

BODIPY/CY3.5 (double-stranded)

| | n = 8 | n = 12 | n = 16 |
|---|---|---|---|
| $\Delta\tau/\sigma_{\Delta\tau}$ | 0.449 | 0.733 | 0.760 |

FITC/CY5 (double-stranded)

| | n = 10 | n = 16 |
|---|---|---|
| $\Delta\tau/\sigma_{\Delta\tau}$ | 0.372 | 0.629 |

BODIPY/CY5 (single-stranded)

| | n = 4 | n = 8 | n = 10 | n = 12 | n = 15 | n = 20 |
|---|---|---|---|---|---|---|
| $\Delta\tau/\sigma_{\Delta\tau}$ | 0.066 | 0.052 | 0.221 | 0.382 | 0.638 | 0.832 |

BODIPY/CY5 (n = 10, single-stranded/double-stranded)

| | 6/4 | 4/6 | 2/8 | 0/10 |
|---|---|---|---|---|
| $\Delta\tau/\sigma_{\Delta\tau}$ | 0.333 | 0.463 | 0.837 | 0.933 |

BODIPY/CY5 (double-stranded, n = 10) labeling position of BODIPY dye (base number from the gap position of a hybrid)

| | 0 | 1 | 2 | 4 |
|---|---|---|---|---|
| $\Delta\tau/\sigma_{\Delta\tau}$ | 0.032 | 0.698 | 0.589 | 0.377 |

For combinations of the fluorescent dyes-Bodipy/Cy5, Bodipy/Cy3.5, and FITC/CY5, the base number between the two nucleotides to which the dyes bind in the hybrid was varied: Table 2 and FIG. 3 show S/N identifying the changes in the fluorescence decay curves then. To see effects on the S/N for identification caused by the difference in the structures between the two nucleotides to which the fluorescent dyes bound (single-stranded or double-stranded), the base numbers were fixed to 10 in the combinations of Bodipy/Cy5 dyes and their spacing was made into a mixed structure of single-stranded and double-stranded, where the ratio of single-stranded to double-stranded was varied: variations in the S/N then are also shown in the Table. To see effects of the labeling positions of the fluorescent dyes in the hybrid, the base numbers were fixed to 10 in the combinations of Bodipy/Cy5 dyes and the labeling positions of Bodipy of the Bodipy-labeled probes (donor probes) were shifted to their middle parts from the 5'-ends (the positions of the gap=0): variations in the S/N then are also shown in the Table.

The above results clearly show the following:

(1) When in the combinations of Bodipy/Cy5 fluorescent dyes, the spacing between the nucleotides to which the two fluorescent dyes bind adopts a double-stranded structure in the hybrids, the base number between the two fluorescent dyes is most preferably from 10 to 12.

(2) When in the combinations of Bodipy/Cy5 fluorescent dyes, the spacing between the nucleotides to which the two fluorescent dyes bind adopts a single-stranded structure in the hybrids, the S/N for identification. improves more as the base number between the two fluorescent dyes increases (in 4<n<20). The S/N for identification at n=20 is smaller compared with the case of a double-stranded structure.

(3) When in the combinations of Bodipy/Cy3.5 fluorescent dyes, the spacing between the nucleotides to which the two fluorescent dyes bind adopts a double-stranded structure in the hybrids, the dependence of S/N on the base number between the two fluorescent dyes shows a trend similar to the combinations of Bodipy/Cy5. However, the S/N values are smaller than those for Bodipy/Cy5.

(4) When in the combinations of FITC/Cy5 fluorescent dyes, the spacing between the nucleotides to which the two fluorescent dyes bind adopts a double-stranded structure in the hybrids, the S/N values are smaller than those for Bodipy/Cy5.

(5) When in the combinations of Bodipy/Cy5 fluorescent dyes (the base number between the nucleotides to which the fluorescent dyes bind, n=10), the structures between the nucleotides to which the two fluorescent dyes bind are made into mixed structures of single-stranded and double-stranded, the case where the structure is all double-stranded gives the best S/N for identification.

(6) When in the combinations of Bodipy/Cy5 fluorescent dyes (the base number between the nucleotides to which the fluorescent dyes bind, n=10), the labeling position of Bodipy of the Bodipy-labeled probes (donor probes) is best at the 5'-end. As the labeling position shifts toward the middle part of the probe, the S/N lowers.

Here, the result in (6) may be interpreted as follows. In the hybrid comprising two probes and a target nucleic acid, a gap on the chain at the probe side is generated between the nucleotides at which the two probes are adjacent to each other. Thus, the corresponding phosphodiester bond on the side of the target nucleic acid has increasing freedom of movement. Accordingly, it is supposed that the magnitude of fluctuations in the distance between the two fluorescent dyes, which results from the movement of the hybrid in an aqueous solution, becomes smaller as the fluorescent dyes approach the gap position of the hybrid. The result in (6) suggests that if either one of the donor and acceptor probes is labeled at a terminus on the side opposing the other probe, it will increase the S/N for identification to the greatest degree.

Based on these results, it is understood that among the detection probes to be used in the present Examples, the most suitable ones are the pair in which Bodipy/Cy5 was used as a combination of the fluorescent dyes and the spacing between the nucleotides to which Bodipy and Cy5 bind forms a double-stranded structure and its base number is from 10 to 12 in the hybrid with a specimen. Here, either dye of Bodipy and Cy5 is labeled to a terminus of the corresponding detection probe.

In the detection probes according to this invention, groups binding fluorescent dye molecules to oligonucleotides are not particularly limited, but they are desirably bound through suitable linkers. In the case where the linker is too short then, there is a possibility that interaction between fluorescent dye molecules and the backbone or base part of a nucleic acid grows strong, and as a result, the desired resonance energy transfer between the two fluorescent dye molecules does not take place sufficiently. Also, in the case where the linker is too long, there is a strong possibility that the two fluorescent dye molecules freely move and fluctuations in the distance between the two fluorescent dye molecules become exceedingly large, which is thus not preferred. Preferable length of the linker for the detection probes according to the invention is from a tetramethylene chain to a decamethylene chain. For binding with fluorescent dye molecules, covalent bond formation reactions known in the art can be used. For example, they are an amide, ester, and ether bond, etc. and particularly an amide bond is preferable. The detection probes used in the present Examples employ a tetramethylene chain as a linker.

Among combinations of fluorescent dyes to be used for the detection probes according to this invention, dyes having fluorophores of the Bodipy type (4-difluoro-4-boro-3a,4a-diaza-s-indacene) are used as donor dyes and to these are combined dyes having fluorophores of the Indocyanin type as acceptors; as examples of those combinations, combinations of Bodipy 493/503 with Cy3, Cy3.5, and Cy5 are illustrated. Other kinds of Bodipy having different wavelength characteristics (Molecular Probes Inc.) and Cy5.5, Cy7 (Amersham) are also usable. Specifically, there are combinations such as "Bodipy-TMR and Cy5" and "Bodipy-TR and Cy7." Similarly to the combination of "Bodipy 493/503 and Cy5," those combinations have characteristics such that the difference in fluorescence lifetime between the donor and the acceptor is about sevenfold and the maximum wavelength in the fluorescence spectrum of the donor is separated from that of the acceptor by about 150 nm. In the combinations "Bodipy-TMR and Cy5.5" and "Bodipy-TR and Cy7," their wavelengths are generally shifted to the longer wavelength side by about 50 nm and about 100 nm, respectively as compared with "Bodipy 493/503 and Cy5." In general, biological samples frequently contain luminescent substances and this luminescence forms background light against measurements, thus lowering measured S/Ns. Because the quantity of luminescence for this background light generally decreases toward the long wavelength region, it is advantageous to use the long wavelength region when the high sensitivity measurements of biological samples is to be performed.

Method for Detecting Specimen

The detection of a specimen using detection probes according to this invention can, for example, be carried out in the following manner (see FIG. 3).

(1) The detection probes are prepared.

(2) The detection probes are added to a sample in appropriate amounts. If the sample contains the specimen, a part of the detection probes forms a hybrid with the specimen.

(3) Employing a recording device capable of fluorescence time-resolved measurements, the fluorescence decay curve in the fluorescence wavelength region of an acceptor is measured. The fluorescence in the fluorescence wavelength region of the acceptor contains fluorescence excited by the energy transfer resulting from the hybrid formation.

(4) The fluorescence decay curve of the detection probes in the fluorescence wavelength region of the acceptor is measured.

(5) The fluorescence decay curve measured in (3) and the fluorescence decay curve measured in (4) are subjected to a comparative examination. If the specimen is present in the sample, the fluorescence decay curve changes. If the specimen is not present in the sample, no significant changes in the two fluorescence decay curves are noted.

Figure 4:
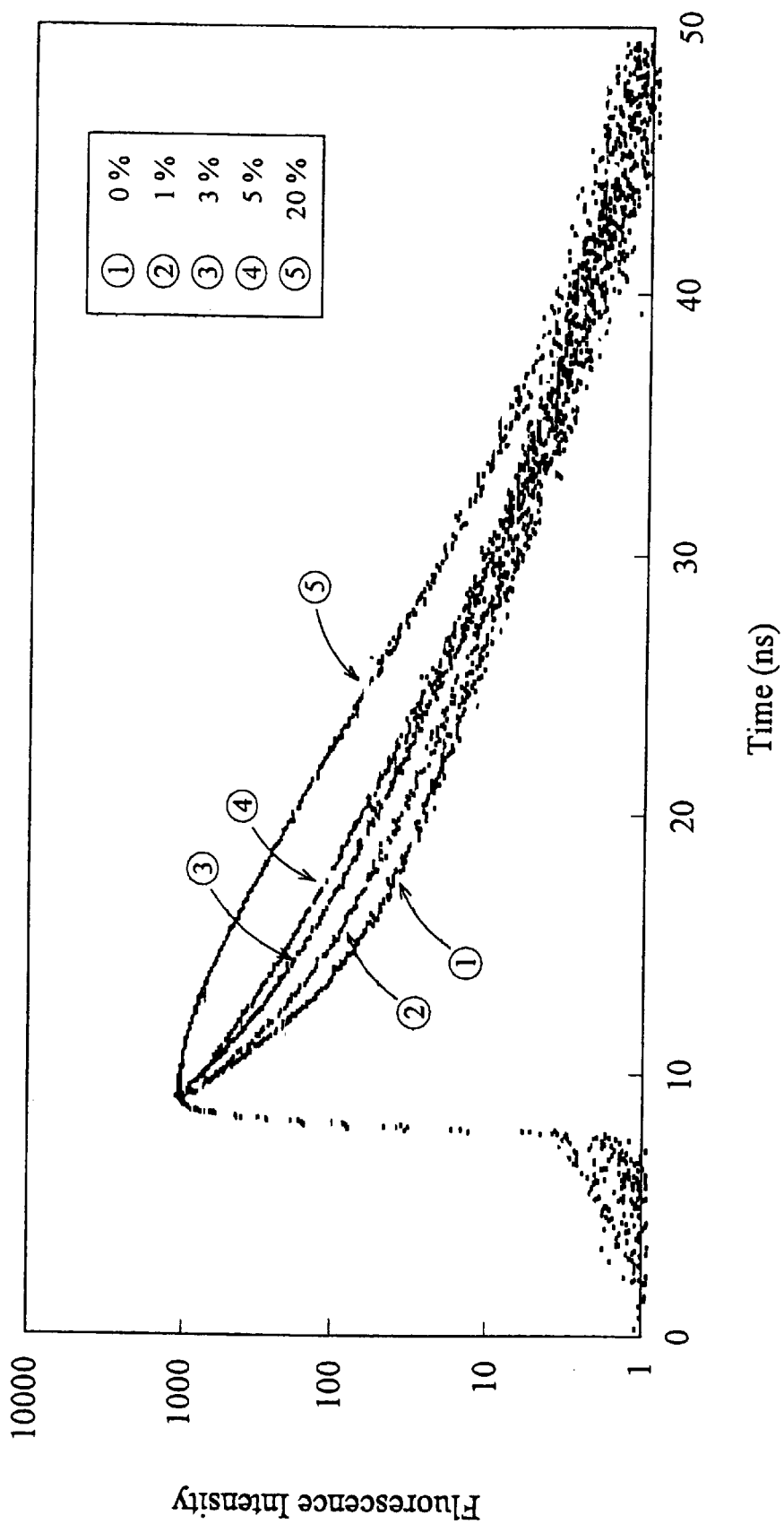
FIG. 4 shows the fluorescence decay curves in the fluorescence wavelength region of an acceptor when a pair of detection probes (oligo-DNAs labeled with fluorescence dye molecules) was mixed with target DNA to be the specimen in such varying proportions as to render the probes excessive. The detection probes used are as follows: the donor fluorescent dye is Bodipy 493/503 and the acceptor fluorescent dye is Cy5; at the time of hybrid formation the nucleotide to which the donor fluorescent dye binds and the nucleotide to which the acceptor fluorescent dye binds are spaced by 12 bases; and its spacing is double-stranded. The proportions of the target DNA to the probes are as follows: (1) 0%, (2) 1%, (3) 3%, (4) 5%, and (5) 20% (target DNA/probe, molar ratio).

Examination for Detection of Specimen Under the Conditions with Excessive Probes The detection probes and method of detection according to this invention enable the detection of the presence of a specimen with high sensitivity even under the conditions where the probes are present in large excess relative to the specimen. FIG. 4 shows the results obtained when the combination of Bodipy/Cy5 fluorescent dyes was used as detection probes, where the spacing between the two nucleotides to which the fluorescent dyes bind adopted a double-stranded structure and its base number was 12. This shows changes in the fluorescence decay curves when the concentration ratio of the detection probes to the target DNA was varied. The concentration of the detection probes was fixed and to this was added the target DNA to provide 0% (no target DNA was added), 1%, 3%, 5%, and 20% as molar ratios. From FIG. 4, it is apparent that even if the detection probes are present in excess 100-fold relative to the target nucleic acid, the fluorescence decay curve sufficiently displaying significant differences is obtained.

One example of methods to quantitatively examine the changes in fluorescence decay curves as represented by FIG.

4 is shown below (Table 3). Fluorescence lifetime τ is computed from the fluorescence decay curve using values of fluorescence intensities in a time zone of from one to nine ns after irradiation with pulse excitation light. The magnitude of scatters in those measurements (standard deviation in the distribution of data when the measurement was conducted many times under the same conditions) is also computed.

$$\tau = -\Delta t / (\ln(D_1/D_0))$$

$D_0$: quantity of fluorescence in a time zone of 1–5 ns
$D_1$: quantity of fluorescence in a time zone of 5–9 ns
$\Delta t = 4$ ns $$\sigma = \tau \times (-\ln(D_1/D_0))/(1/D_0 + 1/D_1)^{1/2}$$

Examination of the difference between the two fluorescence decay curves (here, a difference from the decay curve of a sample containing no target nucleic acid (the control)) is to be performed using $\Delta\tau/\sigma_{\Delta\tau}$ as a parameter.

Here, $\Delta\tau = \tau$ (sample containing target DNA)$-\tau$ (control)
$\sigma_{\Delta\tau} = (\sigma(\text{sample containing target DNA})^2 + \sigma(\text{control})^2)^{1/2}$ $\Delta\tau/\sigma_{\Delta\tau}$ represents S/N identifying the difference between the two fluorescence decay curves and its greater value means that examination of the presence of target the DNA with great accuracy is feasible.

TABLE 3

| probe: BODIPY/CY5 (double-stranded, n = 12) | | | | |
|---|---|---|---|---|
| specimen DNA/probe: | 1% | 3% | 5% | 20% |
| $\Delta\tau/\sigma_{\Delta\tau}$ | 7.09 | 12.10 | 17.14 | 36.02 |

Figure 5:
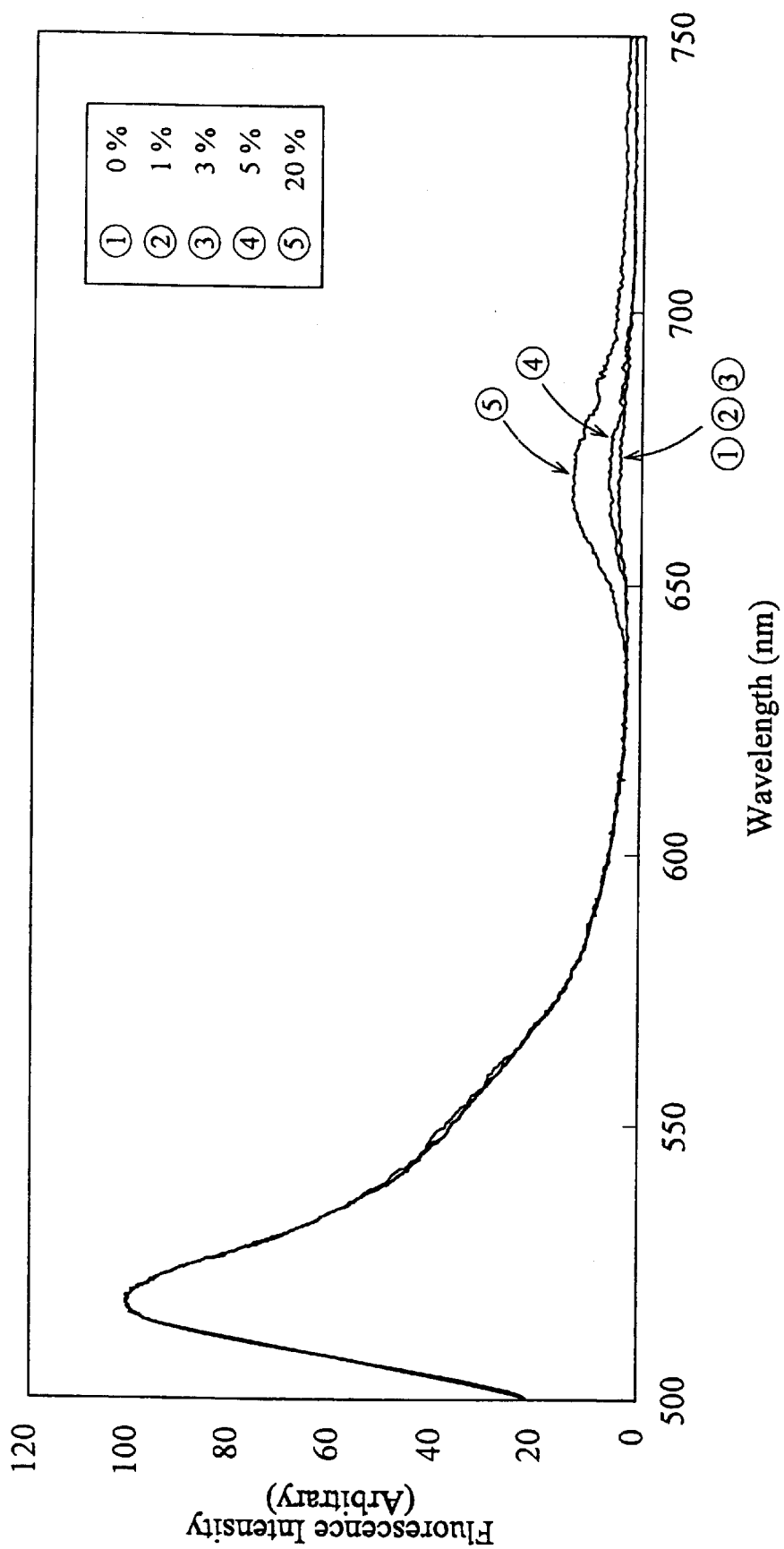
FIG. 5 shows the fluorescence spectra of the samples shown in FIG. 4: a pair of detection probes and a target DNA to be the specimen were mixed in such varying proportions as to render the probes excessive. The detection probes used are as follows: the donor fluorescent dye is Bodipy 493/503 and the acceptor fluorescent dye is Cy5; at the time of hybrid formation the nucleotide to which the donor fluorescent dye binds and the nucleotide to which the acceptor fluorescent dye binds are spaced by 12 bases; and its spacing is double-stranded. The proportions of the target DNA to the probes are: (1) 0%, (2) 1%, (3) 3%, (4) 5%, and (5) 20% (target DNA/probe, molar ratio).

Comparison with Method for Detection of Specimen Based on Fluorescence Spectral Measurements Compared with conventional methods based on the measurements of changes in fluorescence spectra, the present method based on the measurement of fluorescence decay curves has great accuracy for examination over tens of times in the detection of a specimen under the conditions with excessive detection probes. FIG. 5 shows changes in fluorescence spectra for the same sample used in FIG. 4.

The magnitude of changes in a fluorescence spectrum can be expressed in terms of either of the two ratios: the ratio of Ia/Id wherein Id is fluorescence intensity at the maximum wavelength (517 nm) of the Bodipy 493/503 fluorescence and Ia is fluorescence intensity at the maximum wavelength (667 nm) of the Cy5 fluorescence; and the ratio of fluorescence intensity in the wavelength region of the Bodipy fluorescence (e.g., 510–560 nm) to fluorescence intensity in the wavelength region of the Cy5 fluorescence (e.g., 650–700 nm). Here, S/N for identifying the difference between the two fluorescence spectra is expressed by $\Delta I/\sigma_{\Delta I}$.

$\Delta I = I_a/I_b$ (sample containing target DNA)$-I_a/I_b$ (control)
$\sigma_{\Delta I} = (\sigma(\text{sample containing target DNA})^2 + \sigma(\text{control})^2)^{1/2}$
$\sigma = (I_a/I_d) \times (1/I_d + 1/I_a)^{1/2}$

TABLE 4

| probe: BODIPY/CY5 (double-stranded, n = 12) | | | | |
|---|---|---|---|---|
| specimen DNA/probe: | 1% | 3% | 5% | 20% |
| $\Delta (I_a/I_b)/\sigma_{\Delta\tau}$, peak ratio | 0.18 | 0.51 | 0.78 | 3.05 |
| $\Delta (I_a/I_b)/\sigma_{\Delta\tau}$, integration ratio | 1.08 | 3.16 | 4.45 | 16.83 |

From a comparison of numerical values in Tables 3 and 4, it is understood that a method of detection utilizing fluorescence decay curves (time-resolution method) has great superiority over a method utilizing fluorescence spectra for a sample in which detection probes are present in excess relative to a specimen. Especially, it is understood that according as the detection probes become more excessive relative to the specimen, the superiority of the time-resolution method grows greater.

The detection probes and method of detection according to this invention are applicable even if the specimen is RNA.

Figure 36:
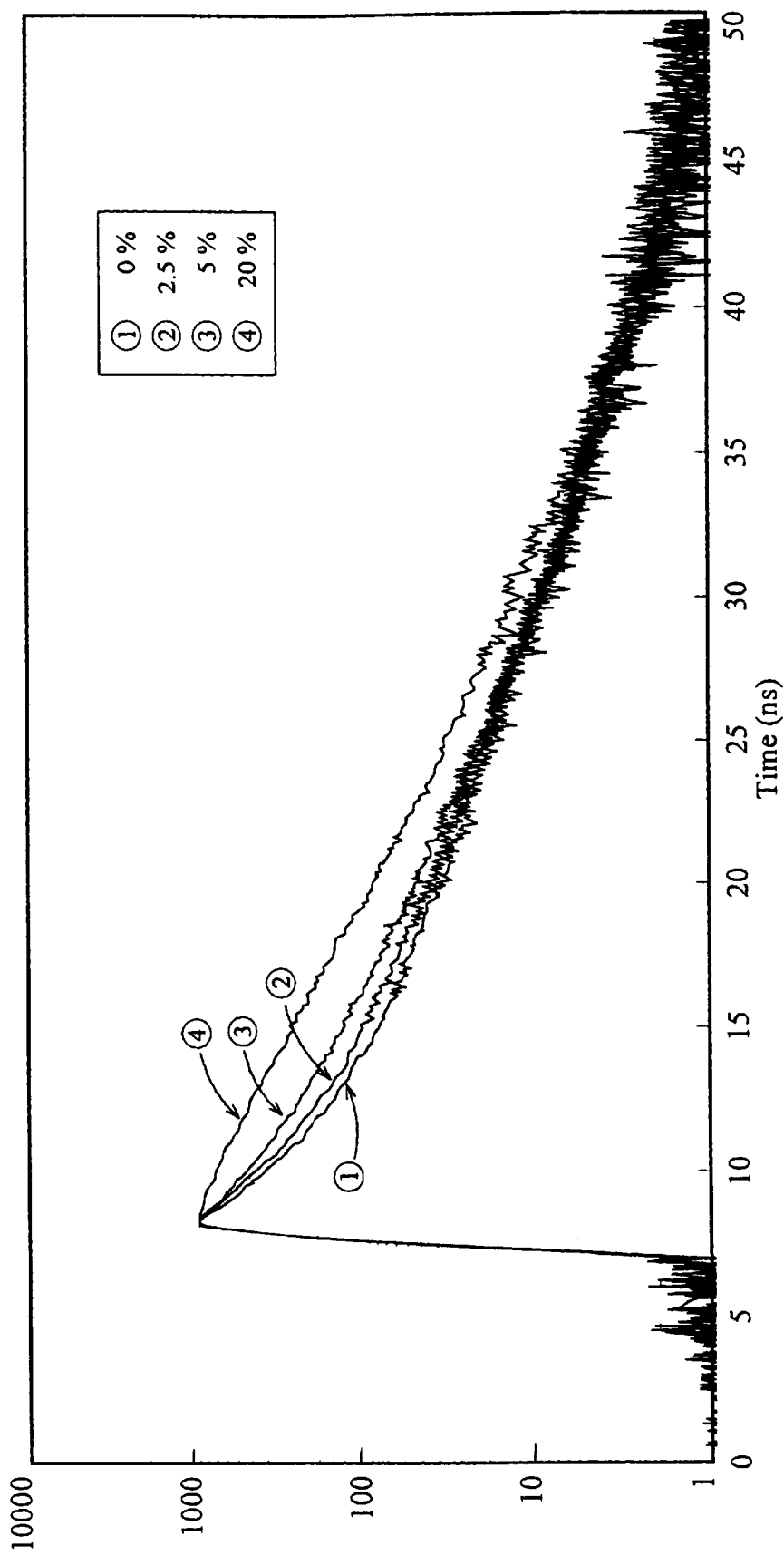
FIG. 36 shows the fluorescence decay curves in the fluorescence wavelength region of an acceptor when a pair of detection probes (oligo-DNAS labeled with fluorescent dye molecules) was mixed with a target RNA to be the specimen in such varying proportions as to render the probes excessive. The detection probes used are as follows: the donor fluorescent dye is Bodipy 493/503 and the acceptor fluorescent dye is Cy5; at the time of hybrid formation the spacing between the nucleotide to which the donor fluorescent dye bind and the nucleotide to which the acceptor fluorescent dye bind is double-stranded; and the base number for the spacing is 12 (n=12). The proportions of the target RNA to the probes are: (1) 0%, (2) 2.5%, (3) 5%, and (4) 20% (target RNA/probe, molar ratio).

FIG. 36 is an example where various detection probes and method of detection according to the invention were used to detect RNA. It is understood that similarly to the results in FIG. 4 where the specimen is DNA, the fluorescence decay curves delay in proportion to the contents of RNA in samples where the detection probes are present in excess relative to RNA, which is the specimen. See Examples for details.

The detection probes and method of detection according to this invention are also effective in the case where the oligonucleotide part of the detection probe is an oligonucleotide of the phosphorothioate type.

FIG. 38 shows an example where oligonucleotides of the phosphorothioate type (S-oligo) were used as detection probes to detect RNA. It is understood that similarly to the results in FIGS. 4 and 36, the fluorescence decay curves delay in proportion to the contents of RNA in samples where the detection probes are present in excess relative to RNA, which is the specimen. See Examples for details.

Application of Probes According to the Invention

The subject that the detection probes and the method using the same can detect is not limited to the detection of nucleic acids to be a specimen. For example, it is also possible to detect alterations of the primary structure of a nucleic acid (such as incorporation of nucleic acid, inversion and deletion) with high sensitivity and great accuracy.

For example, when the incorporation of other DNA fragment into a specified site of a DNA is to be detected, the positions at which two probes are hybridized onto the DNA are set to be on both sides of the site into which the DNA fragment will be incorporated, as is shown in FIG. 6A. If the DNA fragment is not incorporated, energy transfer occurs because the two probes are hybridized adjacently. On the other hand, if the incorporation takes place, the energy transfer efficiency decreases because the two probes are to be hybridized at distant sites, causing the fluorescence decay curve to change. Also, as shown in FIG. 6B, when a probe hybridizing with a DNA fragment to be incorporated is used as one of the probes, the two probes are hybridized adjacently and the energy transfer occurs if the incorporation takes place. The incorporation of other DNA fragment into a specified site of a DNA is utilized in manipulations for gene cloning, e.g., when a desired DNA fragment is incorporated into a vector. If the detection probes and method of detection according to this invention are employed, it does not necessitate manipulations such as separation of non-bonded probes or washing, after addition of the detection probes to the sample and makes it possible to easily detect that the incorporation has taken place.

Figure 7:
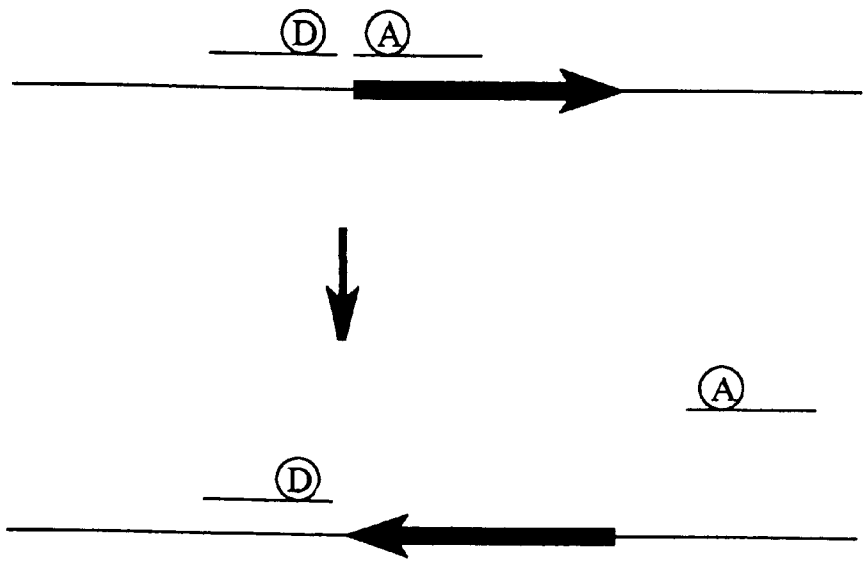
FIG. 7 is a schematic diagram illustrating one of the examples where detection probes and method of detection by the use of the probes according to the invention are applied, indicating that they can be used to detect any change (inversion) by which the direction of a specified site of DNA is inverted during alternations of the primary structure of a nucleic acid.

Also, when an exogenous gene is incorporated into a vector, the direction of incorporation often poses a problem. As shown in FIG. 7, it is designed such that one of the probes is hybridized to one end of a DNA fragment being incorporated; if the DNA is incorporated in one direction (tentative normal direction in FIG. 7, top), the energy transfer occurs, whereas if it is incorporated in the inverted direction (inverted direction in FIG. 7, bottom), the energy transfer does not occur.

Figure 8:
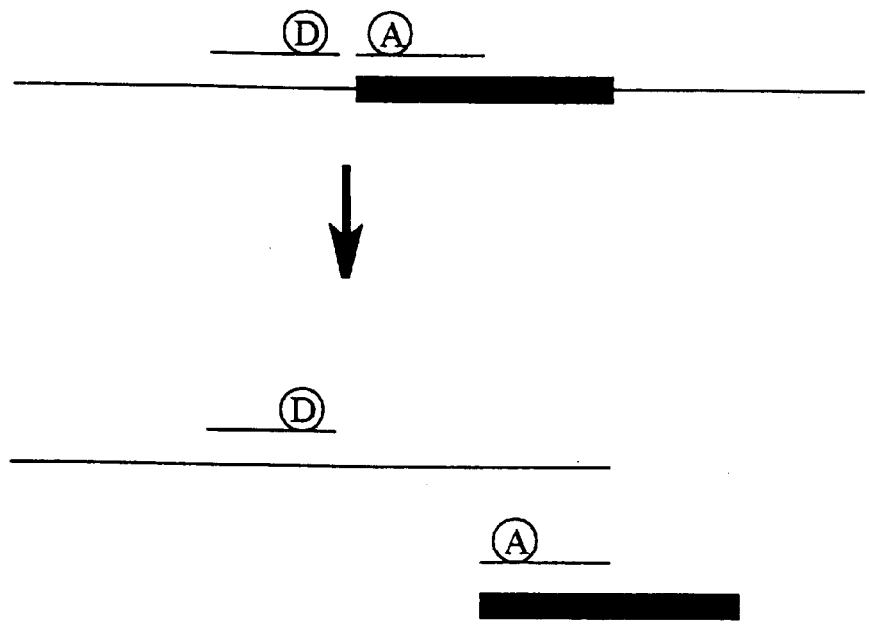
FIG. 8 is a schematic diagram illustrating one of the examples where detection probes and method of detection by the use of the probes according to the invention are applied, indicating that they can be used to detect any change by which a specified site of DNA is deleted during alternations of the primary structure of a nucleic acid.

Also, DNA fragments of certain size may sometimes be removed (i.e., deletion). In some hereditary diseases, the deletion of a DNA fragment from a specified site causes such genepathy. Further, when splicing reaction in cell nuclei produces messenger RNA, an RNA fragment at a specified site (intron) is removed. As shown in FIG. 8, if it is designed such that one of the probes is hybridized to a nucleic acid fragment to be removed, the detection of these reactions is enabled.

EXAMPLES

1. Detection Probes

A variety of oligo-DNAs labeled with various fluorescent dyes were synthesized and these hybridized to DNAs that serve as specimens to be tested. After separating and purifying the resulting hybrids, their fluorescence spectra and fluorescence decay curves were measured.
(1) Synthesis of the Probes Oligo-DNAs having base sequences as described below were synthesized with a DNA/RNA synthesizer (Perkin Elmer Model 394 or Perspective Model 18909) according to the β-cyanoethylamidite method.

```
N1: 5'-GCTATGACCATGXTTAC-3'    (SEQ ID NO:1)

N2: 5'-GCTATGACCAXGATTAC-3'    (SEQ ID NO:2)

N3: 5'-GCTATGACXATGATTAC-3'    (SEQ ID NO:3)

N4: 5'-GCTATGAXCATGATTAC-3'    (SEQ ID NO:4)

N5: 5'-GCTATGXCCATGATTAC-3'    (SEQ ID NO:5)

N6: 5'-GCTAXGACCATGATTAC-3'    (SEQ ID NO:6)

N7: 5'-GCXATGACCATGATTAC-3'    (SEQ ID NO:7)
```

In the above-mentioned probes N1–N7, "X" denotes a Uni-Link AminoModifier (Clonetech Laboratories Inc., Code No. CL5190-1).

```
N8:   5'-AXCGCGCAATTAACCC-3'    (SEQ ID NO:8)

N9:   5'-AGXGCGCAATTAACCC-3'    (SEQ ID NO:9)

N10:  5'-AGCGXGCAATTAACCC-3'    (SEQ ID NO:10)
```

In the above-mentioned probes N8–N10, "X" denotes a Uni-Link AminoModifier.

```
N11:  5'-XAGCGCGCAATTAACCC-3'   (SEQ ID NO:11)
```

In the above-mentioned probe N11, "X" denotes 6-(trifluoroacetylamino)hexyl-(2-cyanoethyl)-(N, N-diisopropyl)-phosphoroamidite (TFAc hexanolamine linker, Perkin Elmer Japan Co. Ltd., Cat No. 400808).

```
N12:  5'-XCCATGATTAC-3'         (SEQ ID NO:12)

N13:  5'-XGACCATGATTAC-3'       (SEQ ID NO:13)

N14:  5'-XTGACCATGATTAC-3'      (SEQ ID NO:14)

N15:  5'-XTATGACCATGATTACX-3'   (SEQ ID NO:15)

N16:  5'-XGCTATGACCATGATTAC-3'  (SEQ ID NO:16)

N17:  5'-GCTATGACCATGATTACX-3'  (SEQ ID NO:17)
```

In the above-mentioned probes N12–N17, "X" denotes a TFAchexanolamine linker.

The respective products thus obtained were separated with an ion-exchange high performance chromatograph and main peaks were fractionated. The conditions used for the ion-exchange high performance chromatograph were as follows: a TSK-GEL DEAE-2WS column (available form Tosoh Co. LTD., 4.6 mm φ×250 mm in full length) was used; a flow rate of 0.8 ml/min, 40° C. temperature, and a $HCOONH_4$ gradient-20% $CH_3CN$ as a mobile phase were used; and detection was carried out at an absorption wavelength of 260 nm. The $HCOONH_4$ gradient was prepared by changing the mixing ratio of two solutions: A solution-0.2 M $HCOONH_4$; and B solution-1 M $HCOONH_4$. For the proportion of the B solution, a gradient of 35%–85% /20 min was used.

After desalting the fractionated solution, the products were lyophilized.
(Labeling of Oligo-DNAs with Bodipy 494/503)

Oligo-DNAs (N8, N9, N10, and N11) were labeled with Bodipy 493/503 dye.

NHSS (N-hydroxysulfosuccinimide sodium salt) 2.5 mg was dissolved in 30 μl of sterilized water and EDAC (1-ethyl-3-(3-dimethylaminopropyl) carbodiimide) 5 mg in 50 μl of sterilized water, respectively. These were mixed with 1 mg of Bodipy 493/503 propionic acid dissolved in 50 μl of DMF and allowed to react at room temperature for 30 min. The resulting solution was mixed with a lyophilized oligo-DNA dissolved in 300 μl of 0.5 M $Na_2CO_3/NaHCO_3$ buffer (pH 9.3) and allowed to react overnight under the shielded light. After the reaction solution was gel filtrated to remove unreacted dye, the product was purified with a reverse phase high performance liquid column chromatograph. The conditions used for the reverse phase high performance liquid column chromatograph were as follows: a CAPCELL PAKC18 (available from Shiseido Co. LTD., 6 mm φ×250 mm in full length) was used; a flow rate of 1 ml/min, 40° C. temperature, and a $CH_3CN$ gradient −5 mMTEAA as a mobile phase were used; and detection was carried out at an absorption wavelength of 260 nm. The $CH_3CN$ gradient was prepared by changing the mixing ratio of two solutions: A solution-5% $CH_3CN$; and B solution-40% $CH_3CN$. For the proportion of the B solution, a gradient of 30%–80% /20 min was used. The absorption spectra of fractionated peaks were measured, thus confirming absorption at 260 nm and absorption of the fluorescent dye (493 nm). These fractions were lyophilized and stored.

```
BP0 (N11 labeled with Bodipy493/503):
5'-XAGCGCGCAATTAACCC-3'      SEQ ID NO:18)

BP1 (N8 labeled with Bodipy493/503):
5'-AXCGCCAATTAACCC-3'        (SEQ ID NO:19)

BP2 (N9 labeled with Bodipy493/503):
5'-AGXGCGCAATTAACCC -3'      (SEQ ID NO:20)

BP4 (N10 labeled with Bodipy493/503):
5'-AGCGXCAATTAACCC -3'       (SEQ ID NO:21)
```

In the above "x" denotes that which Bodipy 493/503 binds to through a linker.
(Labeling of Oligo-DNAs with FITC)

Oligo-DNAs (N11, N12, N13, N14, N15, and N17) were labeled with FITC (fluorescein isothiocyanate, Molecular Probes Inc.).

FITC 1.5 mg was dissolved in 150 μl of DMF. This was mixed with a solution dissolving a lyophilized oligo-DNA in 300 μl of 0.5 M $Na_2CO_3/NaHCO_3$ buffer (pH 9.3) and allowed to react overnight under the shielded light. After the reaction solution was gel filtrated to remove unreacted dye, the product was purified with a reverse phase high performance liquid column chromatograph. The conditions used for the reverse phase high performance liquid column chromatograph were as follows: a CAPCELL PAKC18 (available from Shiseido Co. LTD., 6 mm φ×250 mm in full length) was used; a flow rate of 1 ml/min, 40° C. temperature, and a $CH_3CN$ gradient −5 mMTEAA as a mobile phase were used; and detection was carried out at an absorption wavelength of 260 nm. The $CH_3CN$ gradient was prepared by changing the mixing ratio of two solutions: A solution-5% $CH_3CN$; and B solution-40% $CH_3CN$. For the proportion of the B solution, a gradient of 15%–65% /20 min was used. The absorption spectra of fractionated peaks were measured, thus confirming absorption at 260 nm and absorption of the fluorescent dye (495 nm). These fractions were lyophilized and stored.

```
5F (N11 labeled with FITC):
5'-XAGCGCGCAATTAACCC -3'          (SEQ ID NO:22)

5F10 (N12 labeled with FITC):
5'-XCCATGATTAC-3'                 (SEQ ID NO:23)

5F12 (N13 labeled with FITC):
5'-XGACCATGATTAC-3'               (SEQ ID NO:24)

5F13 (N14 labeled with FITC):
5'-XTGACCATGATTAC-3'              (SEQ ID NO:25)

5F15 (N15 labeled with FITC):
5'- XTATGACCATGATTAC-3'           (SEQ ID NO:26)

3F (N17 labeledd with FITC):
5'-GCTATGACCATGATTACX-3'          (SEQ ID NO:27)
```

In the above "X" denotes that which FITC binds to through a linker.

(Labeling of Oligo-DNA with XRITC)

Oligo-DNA (N11) was labeled with XRITC (rhodamine X isothiocyanate, Molecular Probes Inc.).

XRITC 1.5 mg was dissolved in 150 μl of DMF. This was mixed with a solution dissolving the lyophilized oligo-DNA in 300 μl of 0.5 M $Na_2CO_3$/$NaHCO_3$ buffer (pH 9.3) and allowed to react overnight under the shielded light. After the reaction solution was gel filtrated to remove unreacted dye, the product was purified with a reverse phase high performance liquid column chromatograph. The conditions used for the reverse phase high performance liquid column chromatograph were as follows: a CAPCELL PAKC18 (available from Shiseido Co. LTD., 6 mm φ×250 mm in full length) was used; a flow rate of 1 ml/min, 40° C. temperature, and a $CH_3CN$ gradient −5 mMTEAA as a mobile phase were used; and detection was carried out at an absorption wavelength of 260 nm. The $CH_3CN$ gradient was prepared by changing the mixing ratio of two solutions: A solution-5% $CH_3CN$; and B solution-40% $CH_3CN$. For the proportion of the B solution, a gradient of 30%–80% /20 min was used. The absorption spectra of fractionated peaks were measured, thus confirming absorption at 260 nm and absorption of the fluorescent dye (570 nm). These fractions were lyophilized and stored.

```
5R16 (N11 labeled with XRITC):
5'-XAGCGCGCAATTAACCC-3'           (SEQ ID NO:28)
```

In the above "X" denotes that which XRITC binds to through a linker.

(Labeling of Oligo-DNA with Cy3)

Oligo-DNA (N11) was labeled with Cy3 dye.

One tube of Cy3 dye (Amersham Inc, FluoroLink Cat. No. PA23001) was dissolved in 100 μl of sterilized water. This was mixed with a solution dissolving the lyophilized oligo-DNA in 200 μl of 0.5 M $Na_2CO_3$/$NaHCO_3$ buffer (pH 9.3) and allowed to react overnight under the shielded light. After the reaction solution was gel filtrated to remove unreacted dye, the product was purified with a reverse phase high performance liquid column chromatograph. The conditions used for the reverse phase high performance liquid column chromatograph were as follows: a CAPCELL PAKC18 (available from Shiseido Co. LTD., 6 mm φ0 ×250 mm in full length) was used; a flow rate of 1 ml/min, 40° C. temperature, and a $CH_3CN$ gradient −5 mMTEAA as a mobile phase were used; and detection was carried out at an absorption wavelength of 260 nm. The $CH_3CN$ gradient was prepared by changing the mixing ratio of two solutions: A solution-5% $CH_3CN$; and B solution-40% $CH_3CN$. For the proportion of the B solution, a gradient of 15%–60% /20 min was used. The absorption spectra of fractionated peaks were measured, thus confirming absorption at 260 nm and absorption of the fluorescent dye (550 nm). These fractions were lyophilized and stored.

```
5Cy3 (N11 labeled with Cy3):
5'-XAGCGCGCAATTAACCC-3'           (SEQ ID NO:29)
```

In the above "X" denotes that which Cy3 binds to through a linker.

(Labeling of Oligo-DNAs with Cy3.5)

Oligo-DNAs (N3, N6, and N16) were labeled with Cy3.5 dye.

One tube of Cy3.5 dye (Amersham Inc, FluoroLink Cat. No. PA23501) was dissolved in 100 μl of sterilized water. This was mixed with a solution dissolving a lyophilized oligo-DNA in 200 μl of 0.5 M $Na_2CO_3$/$NaHCO_3$ buffer (pH 9.3) and allowed to react overnight under the shielded light. After the reaction solution was gel filtrated to remove unreacted dye, the product was purified with a reverse phase high performance liquid column chromatograph. The conditions used for the reverse phase high performance liquid column chromatograph were as follows: a CAPCELL PAKC18 (available from Shiseido Co. LTD., 6 mm φ×250 mm in full length) was used; a flow rate of 1 ml/min, 40° C. temperature, and a $CH_3CN$ gradient −5 mMTEAA as a mobile phase were used; and detection was carried out at an absorption wavelength of 260 nm. The $CH_3CN$ gradient was prepared by changing the mixing ratio of two solutions: A solution-5% $CH_3CN$; and B solution-40% $CH_3CN$. For the proportion of the B solution, a gradient of 15%–60% /20 min was used. The absorption spectra of fractionated peaks were measured, thus confirming absorption at 260 nm and absorption of the fluorescent dye (581 nm). These fractions were lyophilized and stored.

```
Cy358 (N3 labeled with Cy3.5):
5'-GCTATGACXATGATTAC-3'           (SEQ ID NO:30)

Cy3512 (N6 labeled with Cy3.5):
5'-GCTAXGACCATGATTAC-3'           (SEQ ID NO:31)

Cy3516 (N6 labeled with Cy3.5):
5'-XGCTATGACCATGATTAC-3'          (SEQ ID NO:32)
```

In the above "X" denotes that which Cy3.5 binds to through a linker.

(Labeling of Oligo-DNAs with Cy5)

Oligo-DNAs (N1, N2, N3, N4, N5, N6, N7, N11, and N17) were labeled with Cy5 dye.

One tube of Cy5 dye (Amersham Inc, FluoroLink Cat. No. PA25001) was dissolved in 100 μl of sterilized water. This was mixed with a solution dissolving a lyophilized oligo-DNA in 200 µl of 0.5 M $Na_2CO_3/NaHCO_3$ buffer (pH 9.3) and allowed to react overnight under the shielded light. After the reaction solution was gel filtrated to remove unreacted dye, the product was purified with a reverse phase high performance liquid column chromatograph. The conditions used for the reverse phase high performance liquid column chromatograph were as follows: a CAPCELL PAKC18 (available from Shiseido Co. LTD., 6 mm φ×250 mm in full length) was used; a flow rate of 1 ml/min, 40° C. temperature, and a $CH_3CN$ gradient -5 mMTEAA as a mobile phase were used; and detection was carried out at an absorption wavelength of 260 nm. The $CH_3CN$ gradient was prepared by changing the mixing ratio of two solutions: A solution-5% $CH_3CN$; and B solution-40% $CH_3CN$. For the proportion of the B solution, a gradient of 15%–60% /20 min was used. The absorption spectra of fractionated peaks were measured, thus confirming absorption at 260 nm and absorption of the fluorescent dye (649 nm). These fractions were lyophilized and stored.

```
Cy54 (N1 labeled with Cy5):
5'-GCTATGACCATGXTTAC-3'      (SEQ ID NO:33)

Cy56 (N2 labeled with Cy5):
5'-GCTATGACCAXGATTAC-3'      (SEQ ID NO:34)

Cy58 (N3 labeled with Cy5):
5'-GCTATGACXATGATTAC-3'      (SEQ ID NO:35)

Cy59 (N4 labeled with Cy5):
5'-GCTCTGAXCATGATTAC-3'      (SEQ ID NO:36)

Cy510 (N5 labeled with Cy5):
5'-GCTTGXCCATGATTAC-3'       (SEQ ID NO:37)

Cy512 (N6 labeled with Cy5):
5'-GCTAXGACCATGATTAC-3'      (SEQ ID NO:38)

Cy514 (N7 labeled with Cy5):
5'-GCXATGACCATGATTAC-3'      (SEQ ID NO:39)

5Cy5 (N11 labeled with Cy5):
5'-XAGCGCGCAATTAACCC -3'     (SEQ ID NO:40)

3Cy5 (N17 labeled with Cy5):
5'-GCTATGACCATGATTACX-3'     (SEQ ID NO:41)
```

In the above "X" denotes that which Cy5 binds to through a linker.

(2) Synthesis of Specimen DNAs

Oligo-DNAs having base sequences as described below were synthesized with a DNA/RNA synthesizer (Perkin Elmer model 394 or Perspective Model 18909) according to the β-cyanoethylamidite method.

The respective products thus obtained were separated with an ion-exchange high performance chromatograph and main peaks were fractionated. The conditions used for the ion-exchange high performance chromatograph were as follows: a TSK-GEL DEAE-2WS column (available from Tosoh Co. LTD., 4.6 mm φ×250 mm in full length) was used; a flow rate of 0.8 ml/min, 40° C. temperature, and a gradient of $HCOOHNH_4$-20% $CH_3CN$ as a mobile phase were used; and detection was carried out at an absorption wavelength of 260 nm. The $HCOOHNH_4$ gradient was prepared by changing the mixing ratio of two solutions: A solution-0.2 M $HCOOHNH_4$; and B solution-1 M $HCOOHNH_4$. For the proportion of the B solution, a gradient of 35%–85%/20 min was used.

After desalting the fractionated solution, the products were lyophilized and stored.

(3) Formation of Hybrids between Detection Probes and Sample DNAs and Separation of the Hybrids by High Performance Liquid Chromatography A pair of detection probes consisting of a donor probe and an acceptor probe 40 pmol (each 40 pmol of the donor and acceptor probes) was mixed with 40 pmol of a specimen DNA in 10 mM Tris-HCl (pH 7.4) and 140 mM NaCl 10 µl at room temperature for 5 min and allowed to hybridize with each other. Subsequently, the hybrid was separated with an ion-exchange high performance chromatograph (ion exchange HPLC). The conditions used for the ion-exchange high performance chromatograph were as follows: a TSK-GEL DEAE-NPR column (available from Tosoh Co. LTD.) was used; a flow rate of 1 ml/min, 40° C. temperature, and a NaCl gradient-20 mMTris-HCl (pH 9.5) as a mobile phase were used; and detection was carried out at an absorption wavelength of 260 nm and with fluorescence intensity (excitation wavelength: the wavelength of the donor dye at its absorption maximum, wavelength of fluorescence detection: the wavelength of the acceptor at its fluorescence maximum). The NaCl gradient was prepared by changing the mixing ratio of two solutions: A solution-20 mM Tris-HCl (pH 9.5); and B solution-20 mM Tris-HCl (pH 9.5), 1 M NaCl. The following conditions were used:

0–2 min:B Solution proportion; a gradient of 25%–45%
2–12 min:B Solution proportion; a gradient of 45%–55%
12–13 min:B Solution proportion; a gradient of 55%–100%.

In the chromatograph a peak manifesting strong fluorescence was identified to be the peak of the hybrid: only when the energy transfer occurs, strong fluorescence is observed. The peaks having strong fluorescence were eluted at positions with longer retention times on the chromatogram than the elution positions of individual probes.

```
T0:  5'-GGGTTAATTGCGCGCTGTAATCATGGTCATAGC-3'                    (SEQ ID NO:42)

T2:  5'-GGGTTAATTGCGCGCTTGGTAATCATGGTCATAGC-3'                  (SEQ ID NO:43)

T4:  5'-GGGTTAATTGCGCGCTTGGCGTAATCATGGTCATAGC-3'                (SEQ ID NO:44)

T6:  5'-GGGTTAATTGCGCGCTTGGCAAGTAATCATGGTCATAGC-3'              (SEQ ID NO:45)

T8:  5'-GGGTTAATTGCGCGCTTGGCAAAAGTAATCATGGTCATAGC-3'            (SEQ ID NO:46)

T10: 5'-GGGTTAATTGCGCGCTTGGCAAAAAAGTAATCATGGTCATAGC-3'          (SEQ ID NO:47)

T12: 5'-GGGTTAATTGCGCGCTTGGCAAAAAAAAGTAATCATGGTCATAGC-3'        (SEQ ID NO:48)

T15: 5'-GGGTTAATTGCGCGCTTGGCAAAAAAAAAAAGTAATCATGGTCATAGC-3'     (SEQ ID NO:49)

T20: 5'-GGGTTAATTGCGCGCTTGGCAAAAAAAAAAAAAAAAGTAATCATGGTCATAGC-3' (SEQ ID NO:50)
```

The fluorescence spectra of the obtained HPLC fractions were measured (fluorescence spectrophotometer: Hitachi F-4500), confirming that the energy transfer had occurred.

(4) Measurements of Fluorescence Decay Curves of Hybrids

The fluorescence decay curves of the hybrids separated, purified with a high performance liquid column chromatograph were measured.

Picosecond fluorescence lifetime recording device C4780 (Hamamatsu Photonics Co. Ltd.)

Excitation light source:
1. Argon laser excitation titanium sapphire laser (Spectra Physics Inc.)
   Argon ion laser: Model 2080
   Mode-lock titanium sapphire laser: TSUNAMI
   Frequency doubler/pulse selector: Model 3980
2. Nitrogen-dye laser (Laser Photonics) Dye: COUMARIN 307.

(a) Fluorescence decay curves in the fluorescence wavelength region of the acceptors (650–700 nm) where the donor fluorescent dyes were Bodipy 493/503 and the acceptor dyes were Cy5 and the structures between the two nucleotides to which the fluorescent dyes bound in the hybrids were made double-stranded and the base number (n) between the fluorescent dyes in the hybrids were set at n=4, 8, 10, 12, and 14.

Bodipy 493/503 is labeled to the 5'-end position of the donor probes and Cy5 is labeled to the middle parts of the acceptor probes.

Separation, Purification of the Hybrids by High Performance Liquid Chromatography

| donor probe | acceptor probe | specimen DNA | elution time (min) on HPLC |
|---|---|---|---|
| BP0 | Cy54 | T0 | 5.89–6.40 |
| BP0 | Cy58 | T0 | 5.82–6.14 |
| BP0 | Cy510 | T0 | 5.90–6.23 |
| BP0 | Cy512 | T0 | 5.97–6.40 |
| BP0 | Cy514 | T0 | 6.03–6.49 |

Fluorescence Decay Curves of the Hybrids

Figure 9:
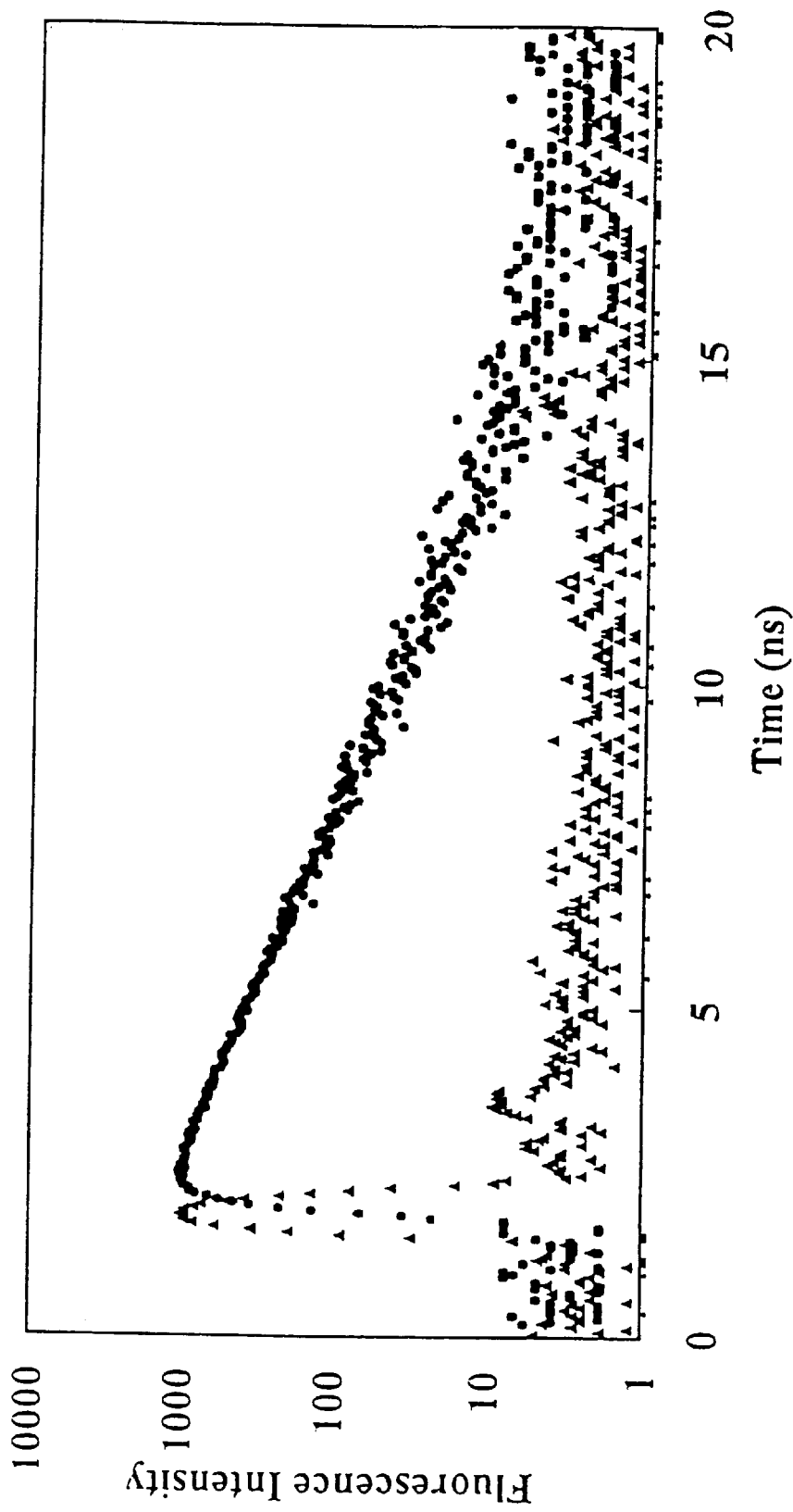
FIG. 9 shows the obtained fluorescence decay curve of a hybrid which was formed with a pair of detection probes and the target DNA when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was four bases (n=4) in the hybrid. (▲) denotes a pulse of excitation light.
Figure 10:
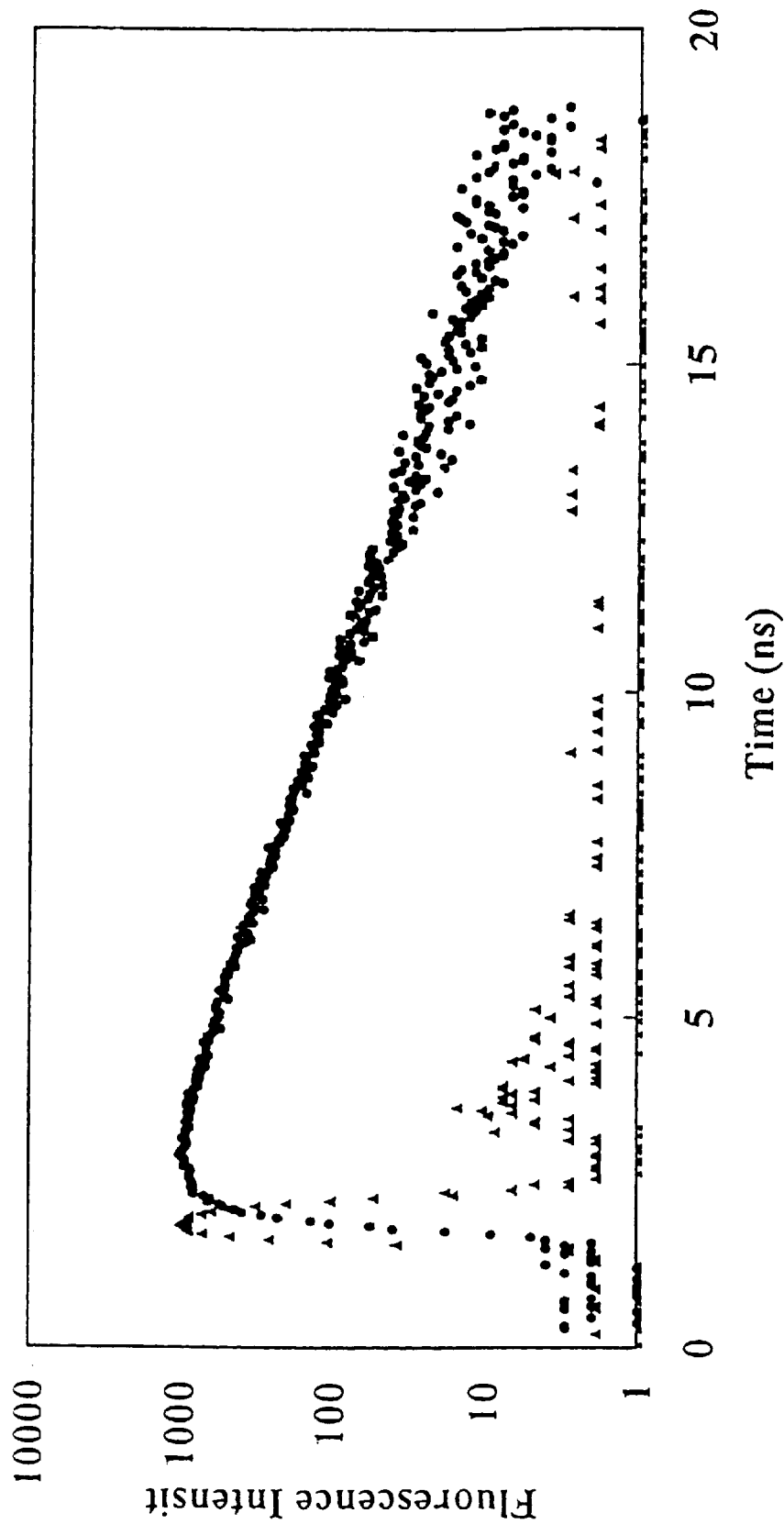
FIG. 10 shows the obtained fluorescence decay curve of a hybrid which was formed with a pair of detection probes and the target DNA when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was eight bases (n=8) in the hybrid. (▲) denotes a pulse of excitation light.
Figure 11:
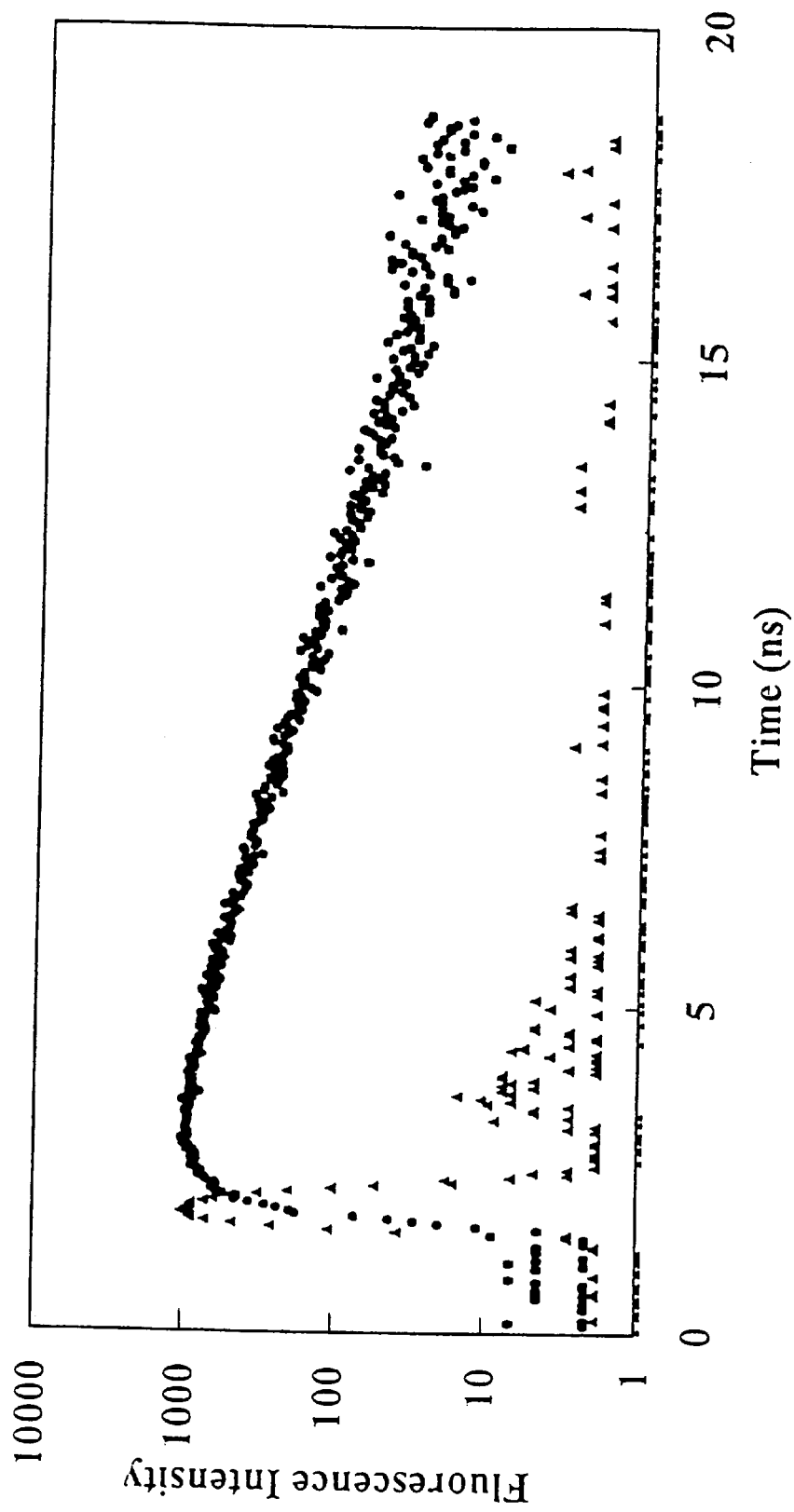
FIG. 11 shows the obtained fluorescence decay curve of a hybrid which was formed with a pair of detection probes and the target DNA when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which fluorescent dyes bound was 10 bases (n=10) in the hybrid. (▲) denotes a pulse of excitation light.
Figure 12:
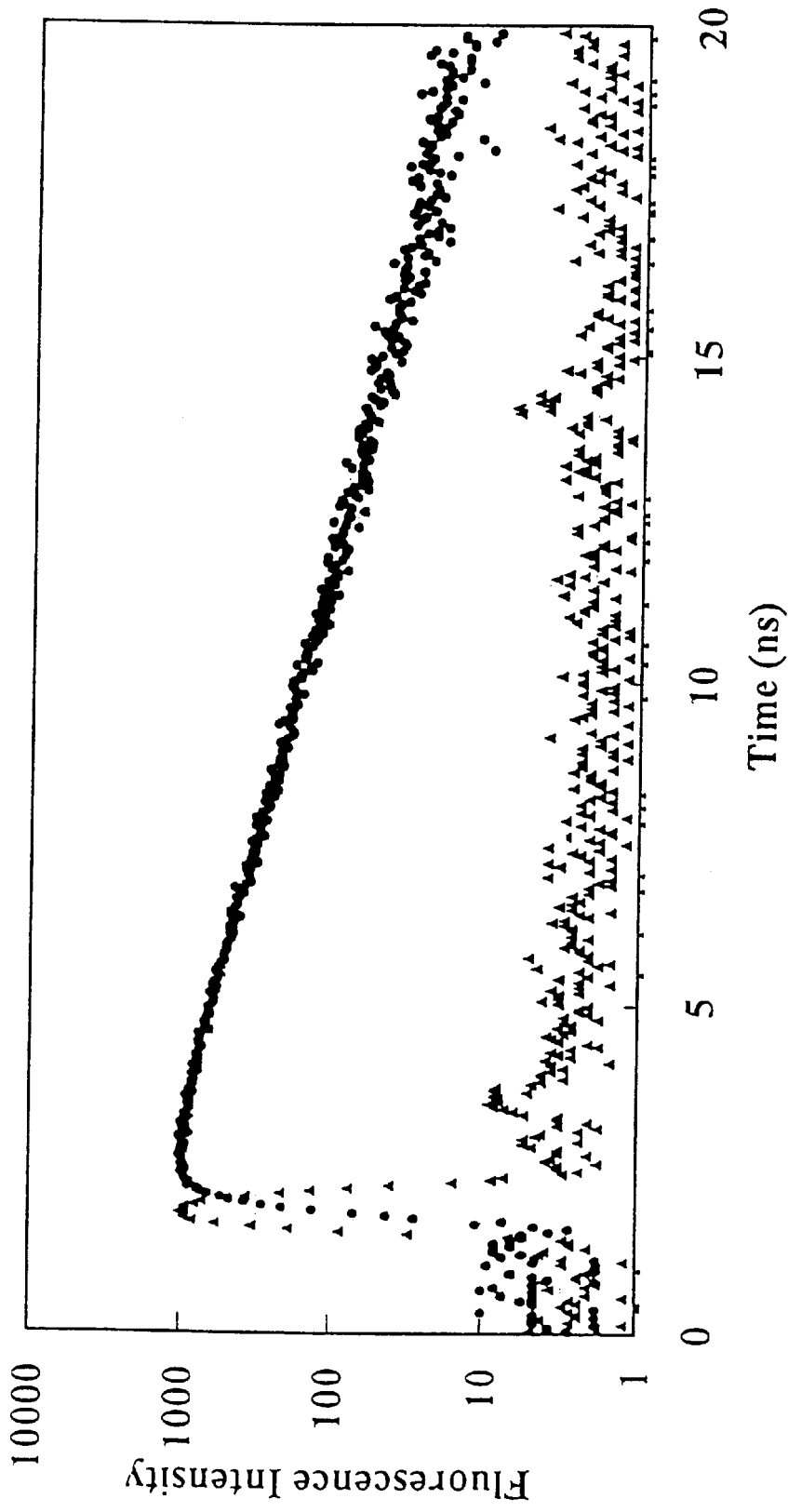
FIG. 12 shows the obtained fluorescence decay curve of a hybrid which was formed with a pair of detection probes and the target DNA when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was 12 bases (n=12) in the hybrid. (▲) denotes a pulse of excitation light.
Figure 13:
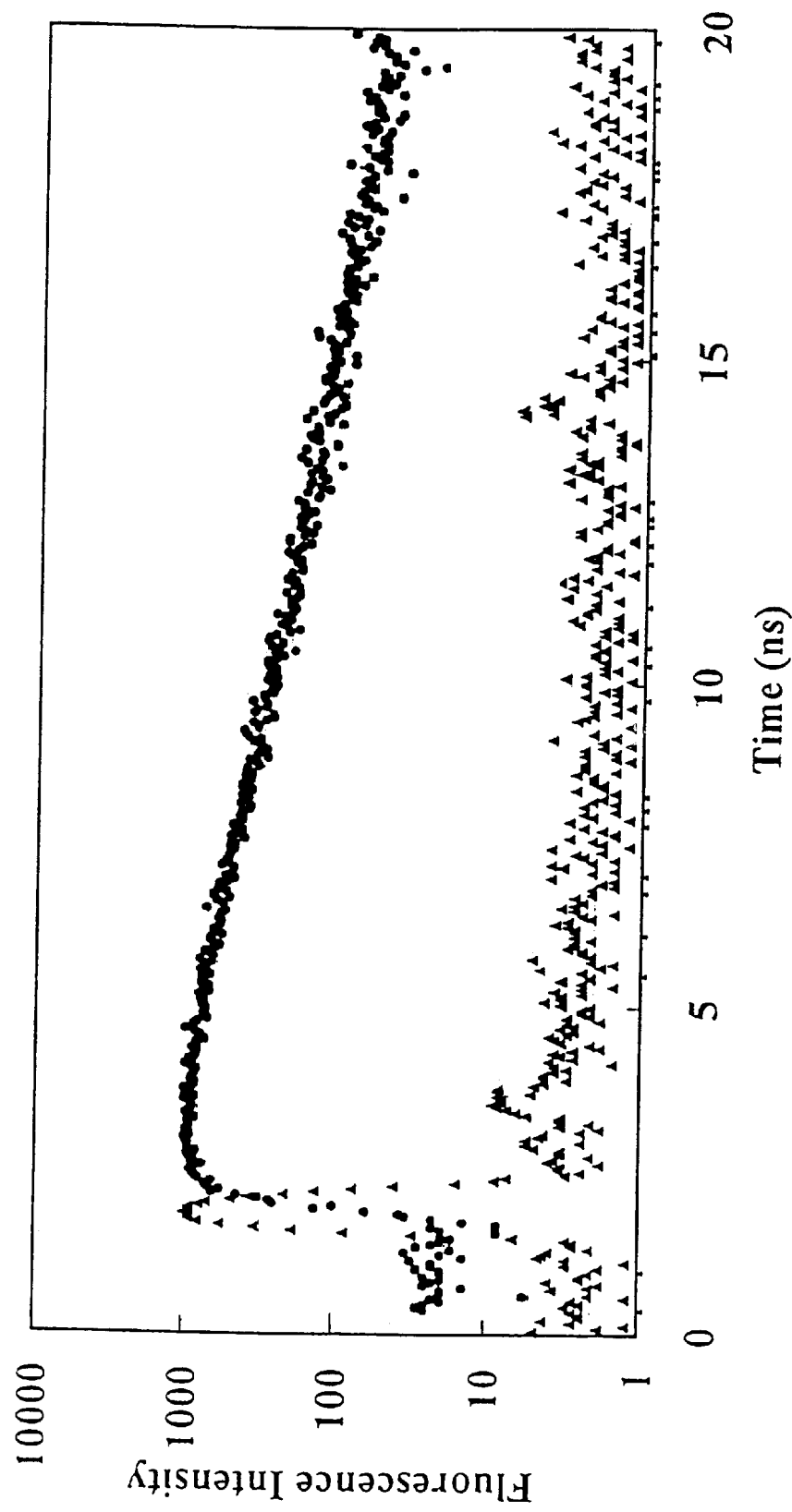
FIG. 13 shows the obtained fluorescence decay curve of a hybrid which was formed with a pair of detection probes and the target DNA when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was 14 bases (n=14) in the hybrid. (▲) denotes a pulse of excitation light.
Figure 14:
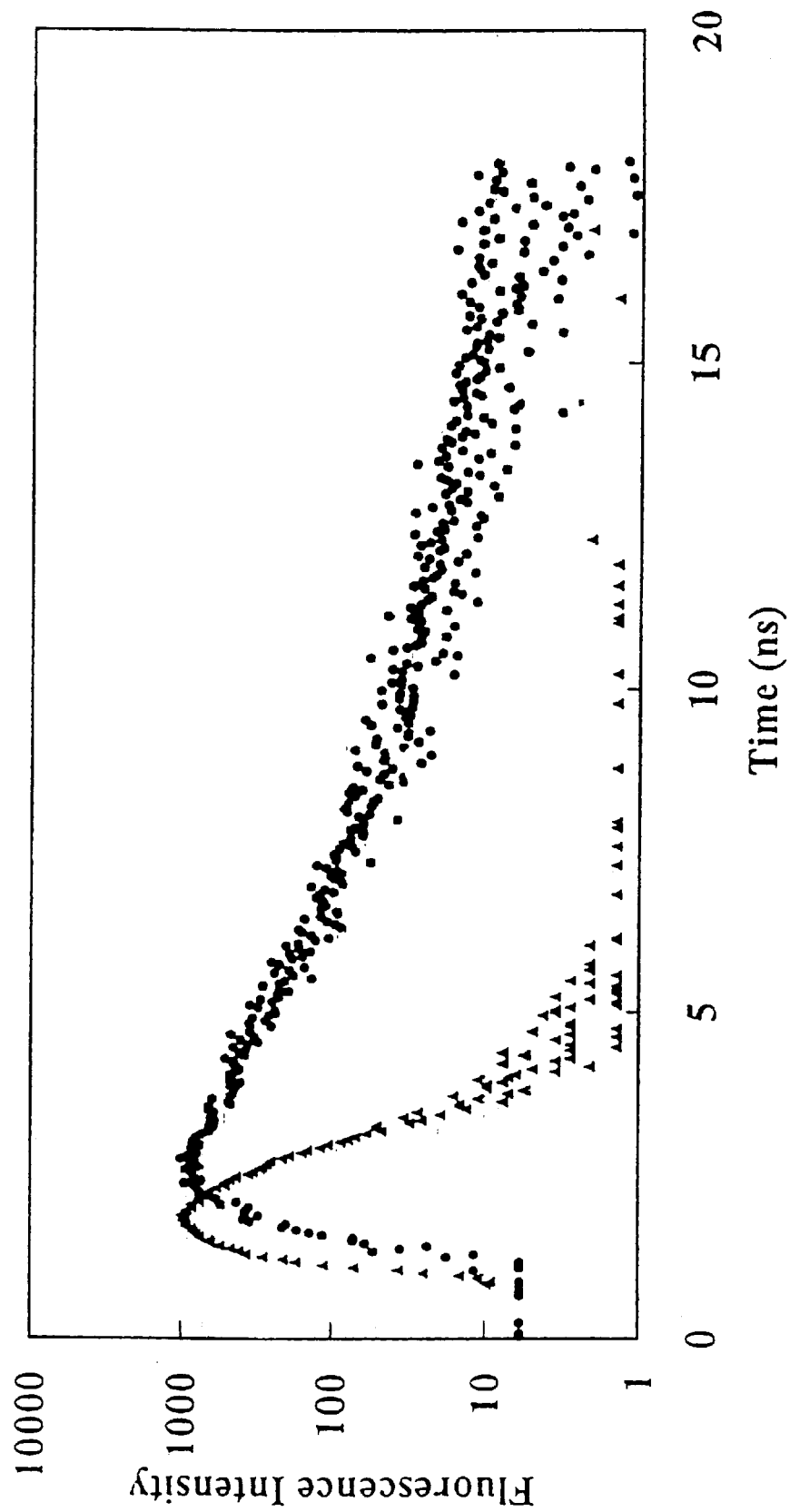
FIG. 14 shows the fluorescence decay curve of the detection probes (specimen DNA not contained), which is a control fluorescence decay curve (●) against FIGS. 9–13. (▲) denotes a pulse of excitation light.

| hybrid | base number (n) between the fluorescent dyes | fluorescence decay curve |
|---|---|---|
| BP0/Cy54/T0 | n = 4 | FIG. 9 |
| BP0/Cy58/T0 | n = 8 | FIG. 10 |
| BP0/Cy510/T0 | n = 10 | FIG. 11 |
| BP0/Cy512/T0 | n = 12 | FIG. 12 |
| BP0/Cy514/T0 | n = 14 | FIG. 13 |
| BP0/Cy510 (two kinds of probes were mixed) | | FIG. 14 |

Excitation light: titanium sapphire laser 480 nm (FIGS. 9–13) nitrogen-dye laser 490 nm (FIG. 14) Wavelength region of fluorescence measurements: 650–700 nm.

The "BP0/Cy510" is the sample where BP0 40 pmol and Cy510 40 pmol were dissolved in 200 μl of 20 mM Tris-HCl (pH 7.4) and 0.5 M NaCl.

(b) Fluorescence decay curves in the fluorescence wavelength region of the acceptors (650–700 nm) where the donor fluorescent dyes were Bodipy 493/503 and the acceptor dyes were Cy5 and the base numbers (n) between the fluorescent dyes in the hybrids were set at n=10 and the structures between the two nucleotides to which the fluorescent dyes bound in the hybrids were made into mixtures of double-strand and single-strand. Bodipy 493/503 is labeled to the 5'-end positions of the donor probes and Cy5 is labeled to the middle parts of the acceptor probes.

Separation, Purification of the Hybrids by High Performance Liquid Chromatography

| donor probe | acceptor probe | specimen DNA | elution time (min) on HPLC |
|---|---|---|---|
| BP0 | Cy510 | T0 | 6.01–6.51 |
| BP0 | Cy58 | T2 | 5.63–6.24 |
| BP0 | Cy56 | T4 | 5.55–6.24 |
| BP0 | Cy54 | T6 | 5.99–6.42 |

Fluorescence Decay Curves of the Hybrids

Figure 15:
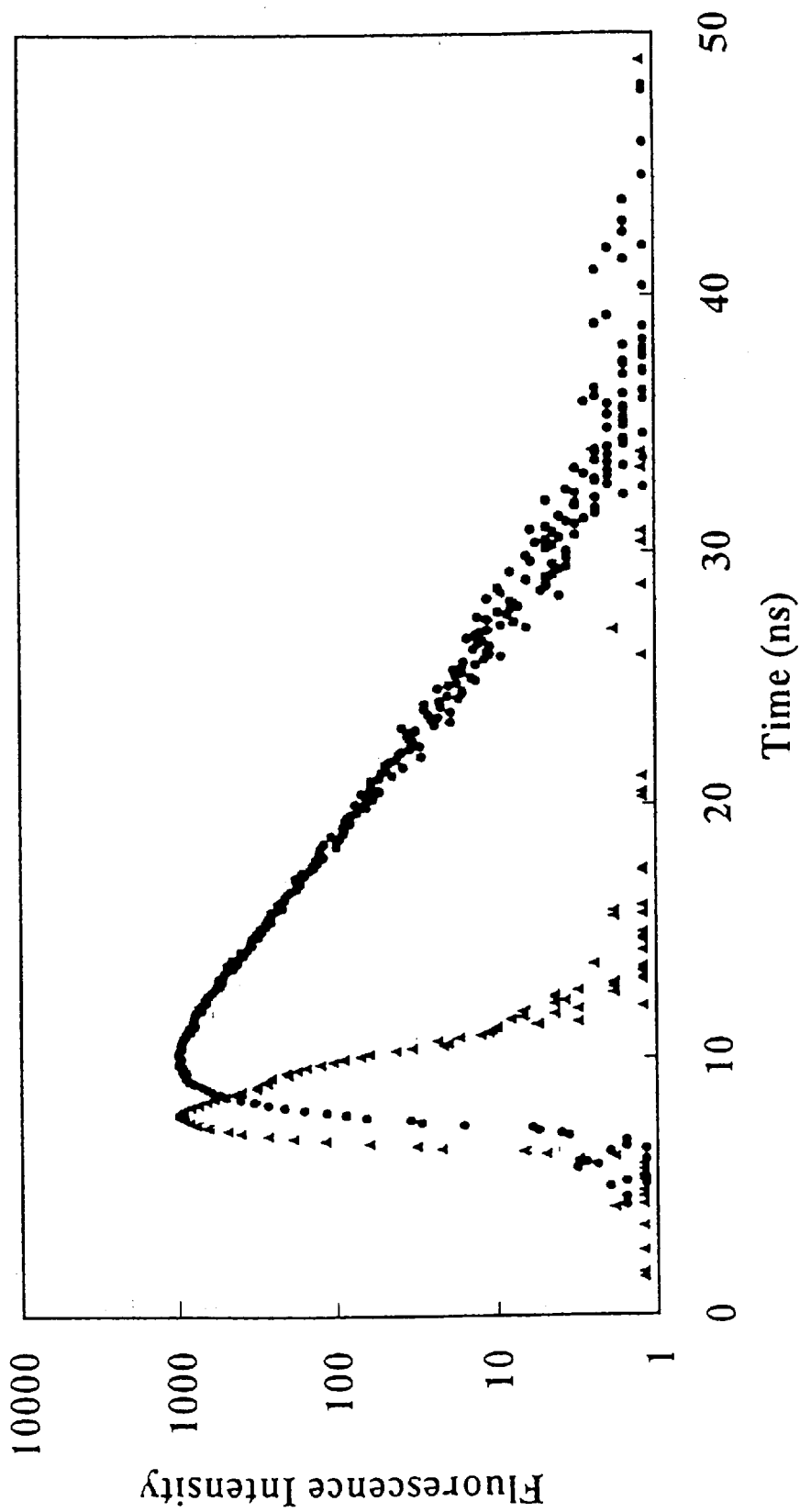
FIG. 15 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. The two nucleotides to which the fluorescent dyes bind are spaced by 10 bases (n=10) in a hybrid. (●) denotes the fluorescence decay curve when there were used the detection probes where the spacing between the two nucleotides to which the fluorescent dyes bound was double-stranded throughout in the hybrid. (▲) denotes a pulse of excitation light.
Figure 16:
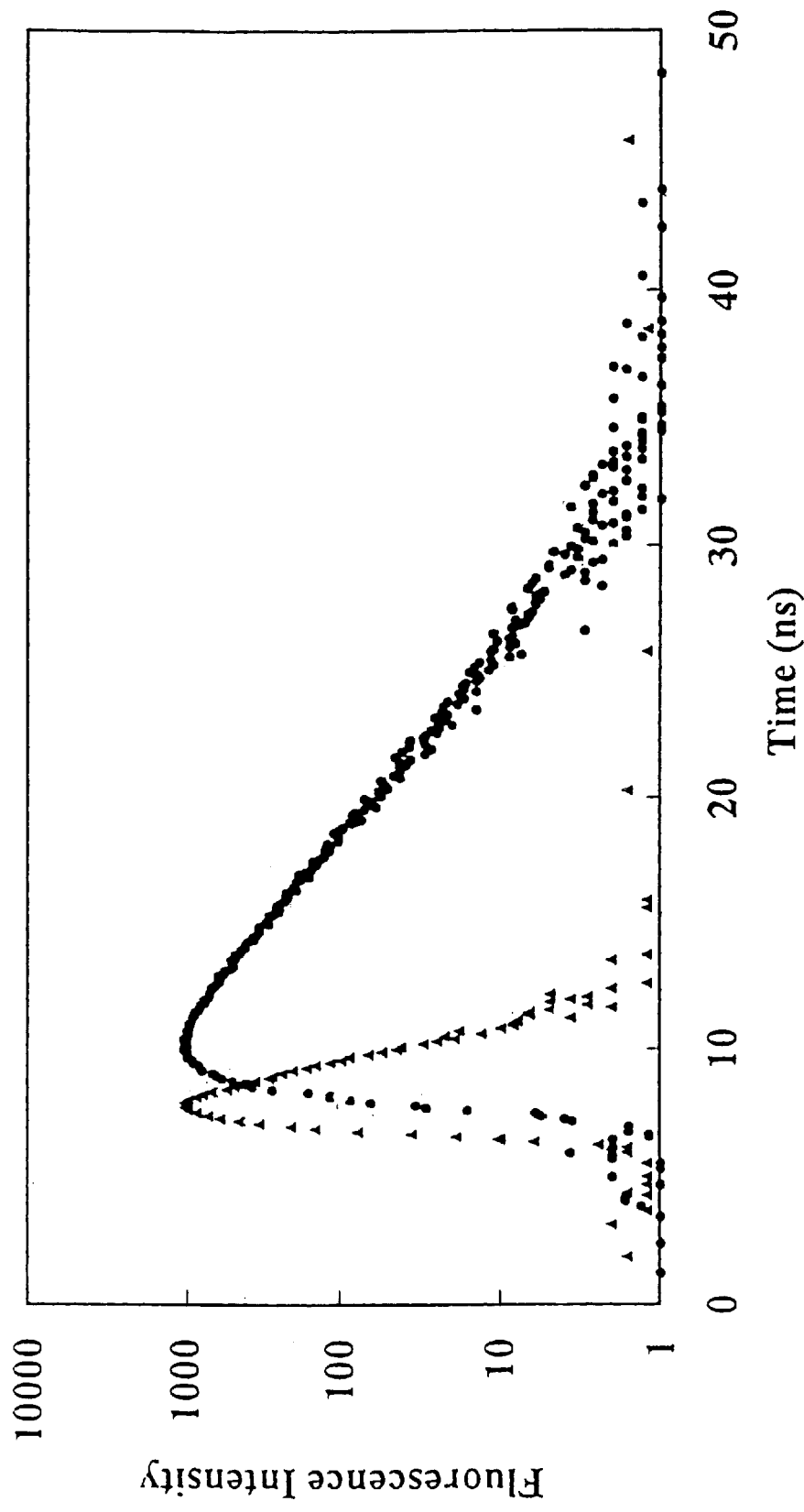
FIG. 16 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. The two nucleotides to which the fluorescent dyes bound are spaced by 10 bases (n=10) in a hybrid. (●) denotes the fluorescence decay curve when there were used the detection probes where the spacing between the two nucleotides to which the fluorescent dyes bound consisted of a single-stranded portion with two bases and a double-stranded portion with eight bases in the hybrid. (▲) denotes a pulse of excitation light.
Figure 17:
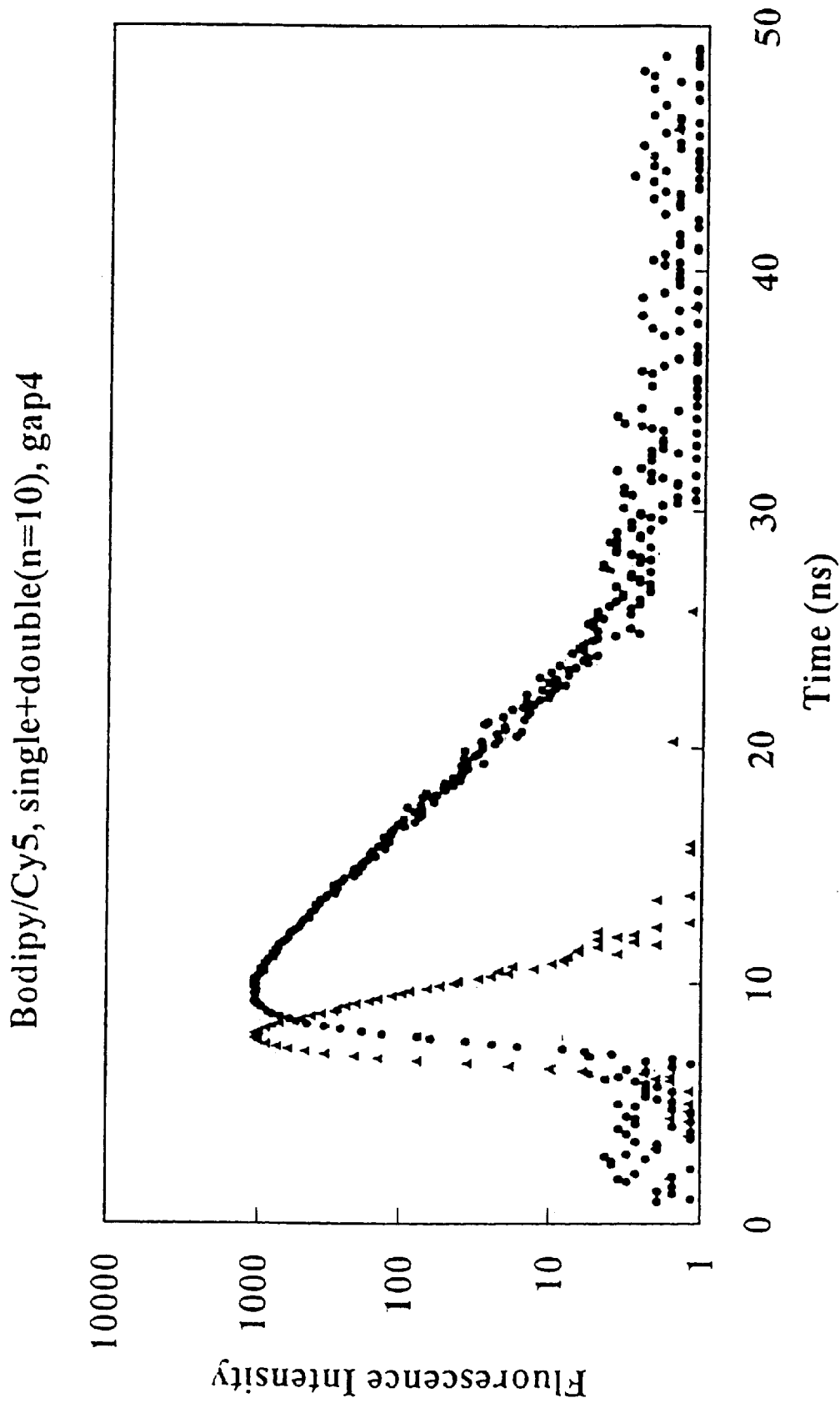
FIG. 17 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. The two nucleotides to which the fluorescent dyes bind are spaced by 10 bases (n=10) in a hybrid. (●) denotes the fluorescence decay curve when there were used the detection probes where the spacing between the two nucleotides to which the fluorescent dyes bound consisted of a single-stranded portion with four bases and a double-stranded portion with six bases in the hybrid. (▲) denotes a pulse of excitation light.
Figure 18:
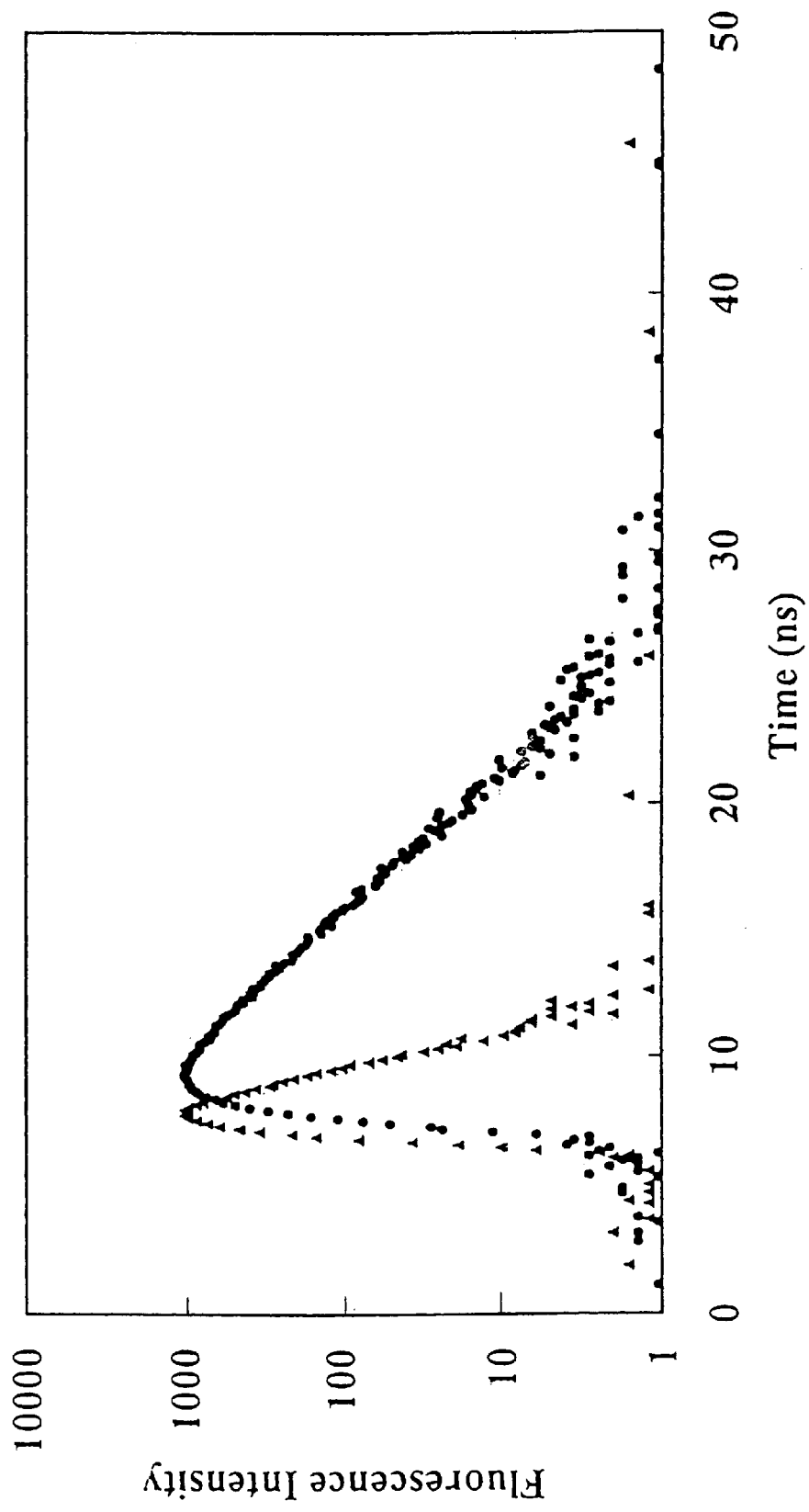
FIG. 18 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. The two nucleotides to which the fluorescence dyes bind are spaced by 10 bases (n=10) in a hybrid. (●) denotes the fluorescence decay curve when there were used the detection probes where the spacing between the two nucleotides to which the fluorescent dyes bound consisted of a single-stranded portion with six bases and a double-stranded portion with four bases in the hybrid. (▲) denotes a pulse of excitation light.
Figure 19:
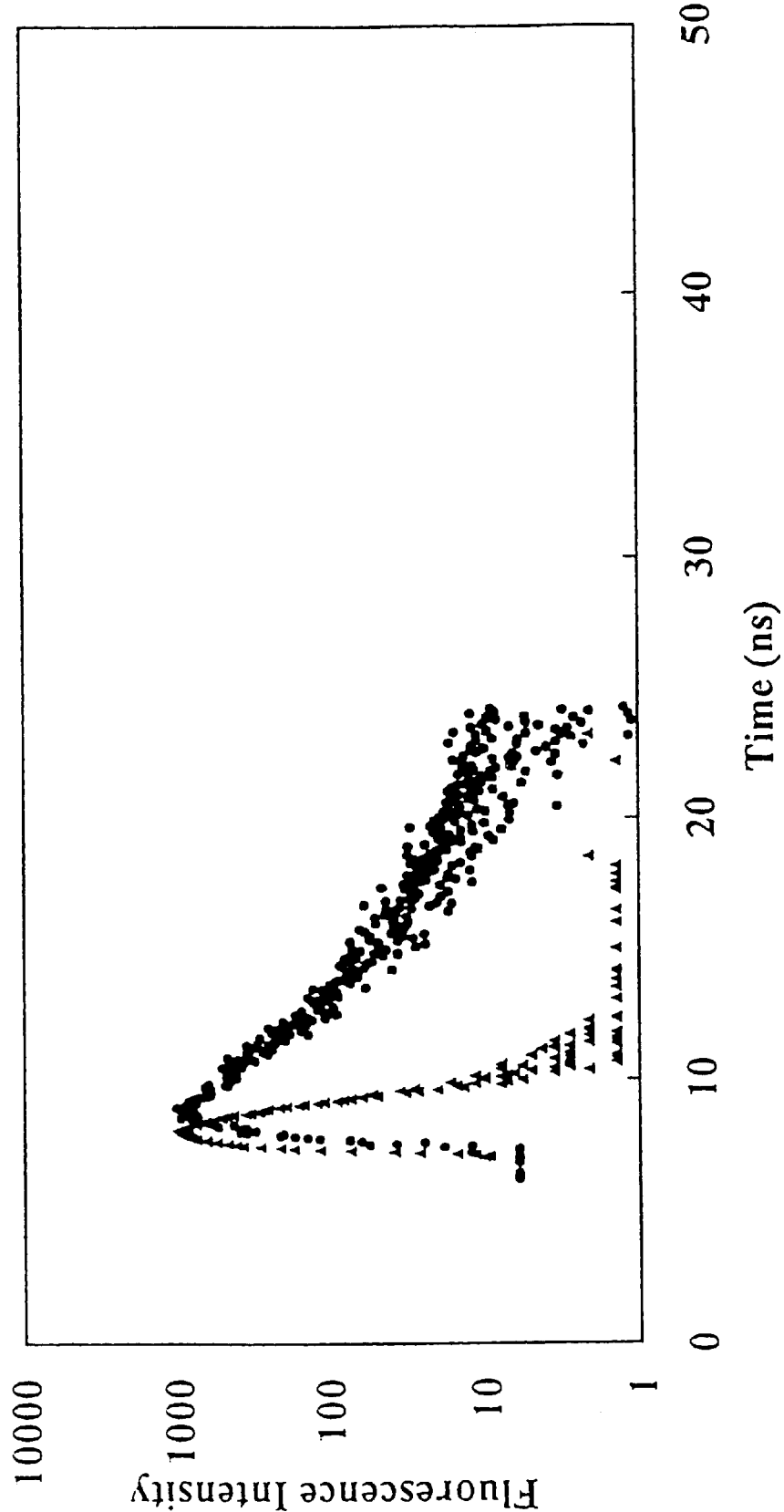
FIG. 19 shows the fluorescence decay curve of the detection probes (specimen DNA not contained), which is a control fluorescence decay curve (●) against FIGS. 15–18. (▲) denotes a pulse of excitation light.

| hybrid | the number of bases (gap) adopting a single-stranded structure | fluorescence decay curve |
|---|---|---|
| BP0/Cy510/T0 | 0 | FIG. 15 |
| BP0/Cy58/T2 | 2 | FIG. 16 |
| BP0/Cy56/T4 | 4 | FIG. 17 |
| BP0/Cy54/T6 | 6 | FIG. 18 |
| BP0/Cy510 (two kinds of probes were mixed) | | FIG. 19 |

Excitation light: titanium sapphire laser 480 nm (FIG. 19) nitrogen-dye laser 490 nm (FIGS. 15–18) Wavelength region of fluorescence measurements: 650–700 nm.

The "BP0/Cy5" is the sample where BP0 40 pmol and Cy510 40 pmol were dissolved in 200 μl of 20 mM Tris-HCl (pH 9.5) and 0.5 M NaCl.

(c) Fluorescence decay curves in the fluorescence wavelength region of the acceptors (650–700 nm) where the donor fluorescent dyes were Bodipy 493/503 and the acceptor dyes were Cy5 and the base numbers (n) between the fluorescent dyes in the hybrids were set at n=10, the structures between the two nucleotides to which the fluorescent dyes bound in the hybrids were made double-strand, and the labeling positions of one fluorescent dye in the hybrids were separated from the position of "gap" (the site at which the two probes were adjacent to each other) by 0 (the terminal site of a probe), one, two, and four bases, respectively. Bodipy 493/503 is labeled to the 5'-end position of BP0 or the middle parts of BP1, BP2 and BP4 within the donor probes and Cy5 is labeled to the middle parts of the acceptor probes.

Separation, Purification of the Hybrids by High Performance Liquid Chromatography

| donor probe | acceptor probe | specimen DNA | elution time (min) on HPLC |
|---|---|---|---|
| BP0 | Cy510 | T0 | 6.01–6.51 |
| BP1 | Cy59 | T0 | 5.52–6.12 |
| BP2 | Cy58 | T0 | 5.45–5.99 |
| BP4 | Cy56 | T6 | 5.46–5.91 |

Fluorescence Decay Curves of the Hybrids

Figure 20:
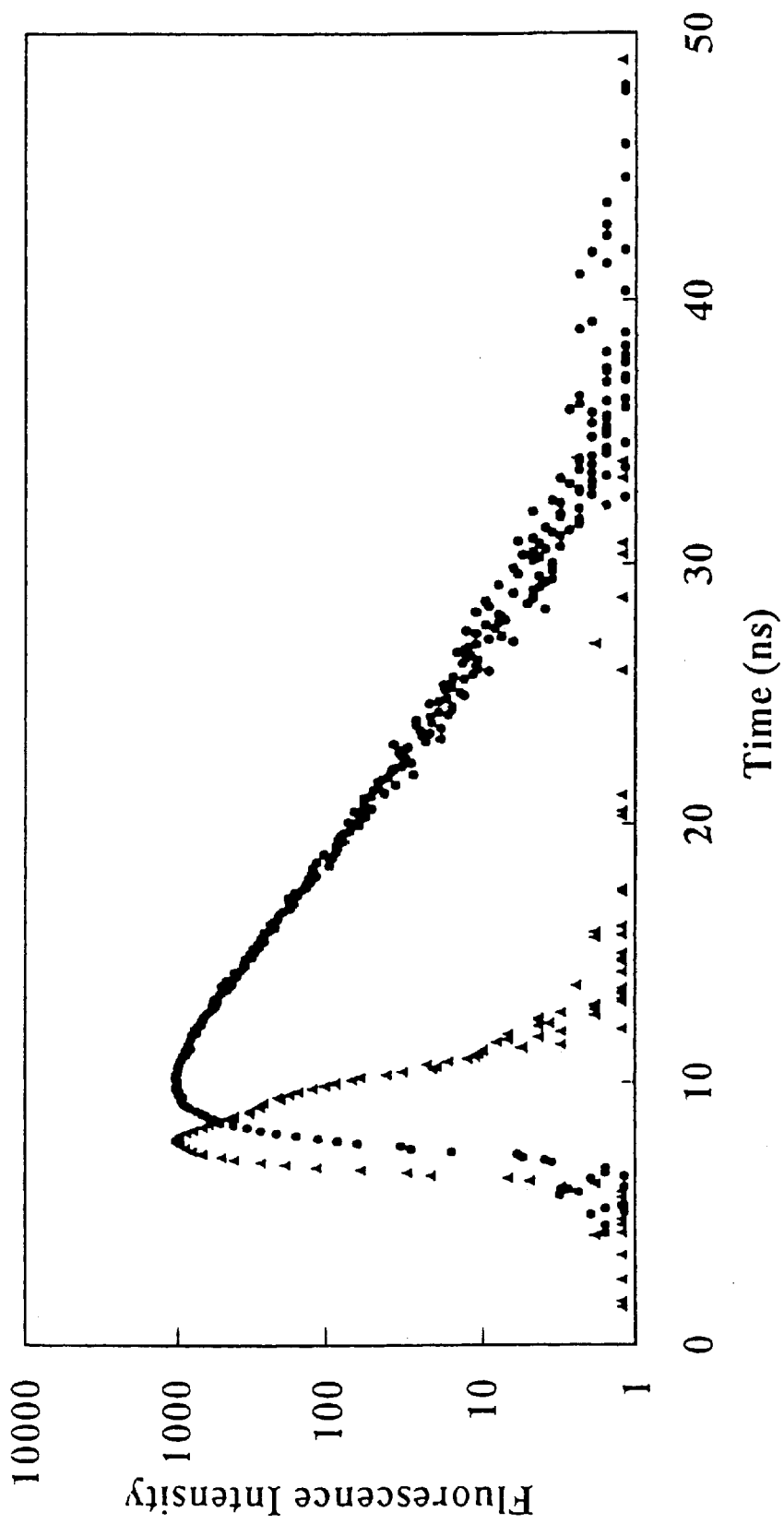
FIG. 20 shows the obtained fluorescence decay curve of a hybrid which was formed with a pair of detection probes and the target DNA (●) when the following pair was used as detection probes. Bodipy 493/503 was used as a donor fluorescent dye, and Cy5 as an acceptor fluorescent dye. The two nucleotides to which the fluorescent dyes bind are spaced by 10 bases (n=10) in a hybrid and its spacing forms a double-strand. (●) denotes the fluorescence decay curve when there were used the detection probes where the labeling position of Bodipy 493/503 was at the 5'-end of the donor probe (i.e., Bodipy 493/503 was bound to the nucleotide at which the two probes adjoined in the hybrid). The labeling position of Cy5 in the acceptor probe is at its position where n equals to 10 (intermediate labeling). (▲) denotes a pulse of excitation light.
Figure 21:
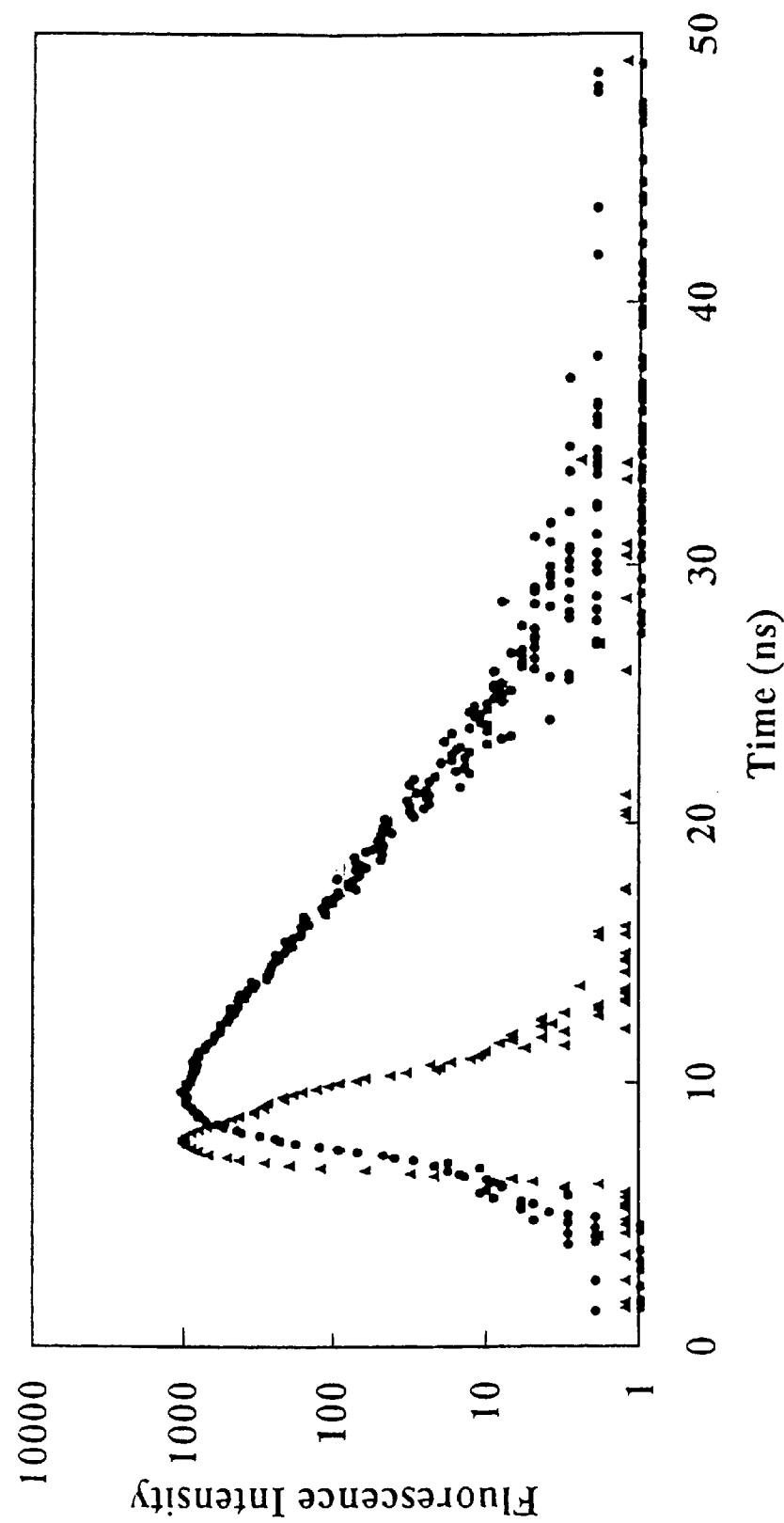
FIG. 21 shows the obtained fluorescence decay curve of a hybrid which was formed with a pair of detection probes and the target DNA (●) when the following pair was used as detection probes. Bodipy 493/503 was used as a donor fluorescent dye, and Cy5 as an acceptor fluorescent dye. The two nucleotides to which the fluorescent dyes bind are spaced by 10 bases (n=10) in a hybrid and its spacing forms a double-strand. (●) denotes the fluorescence decay curve when there were used the detection probes where the labeling position of Bodipy 493/503 in the donor probe was set at a position shifted one base inside from the position of a gap of the two probes (i.e., the position facing the acceptor probe: the 5'-end of the donor probe) in the hybrid. The labeling position of Cy5 in the acceptor probe is at its position where n equals to 10 (intermediate labeling). (▲) denotes a pulse of excitation light.
Figure 22:
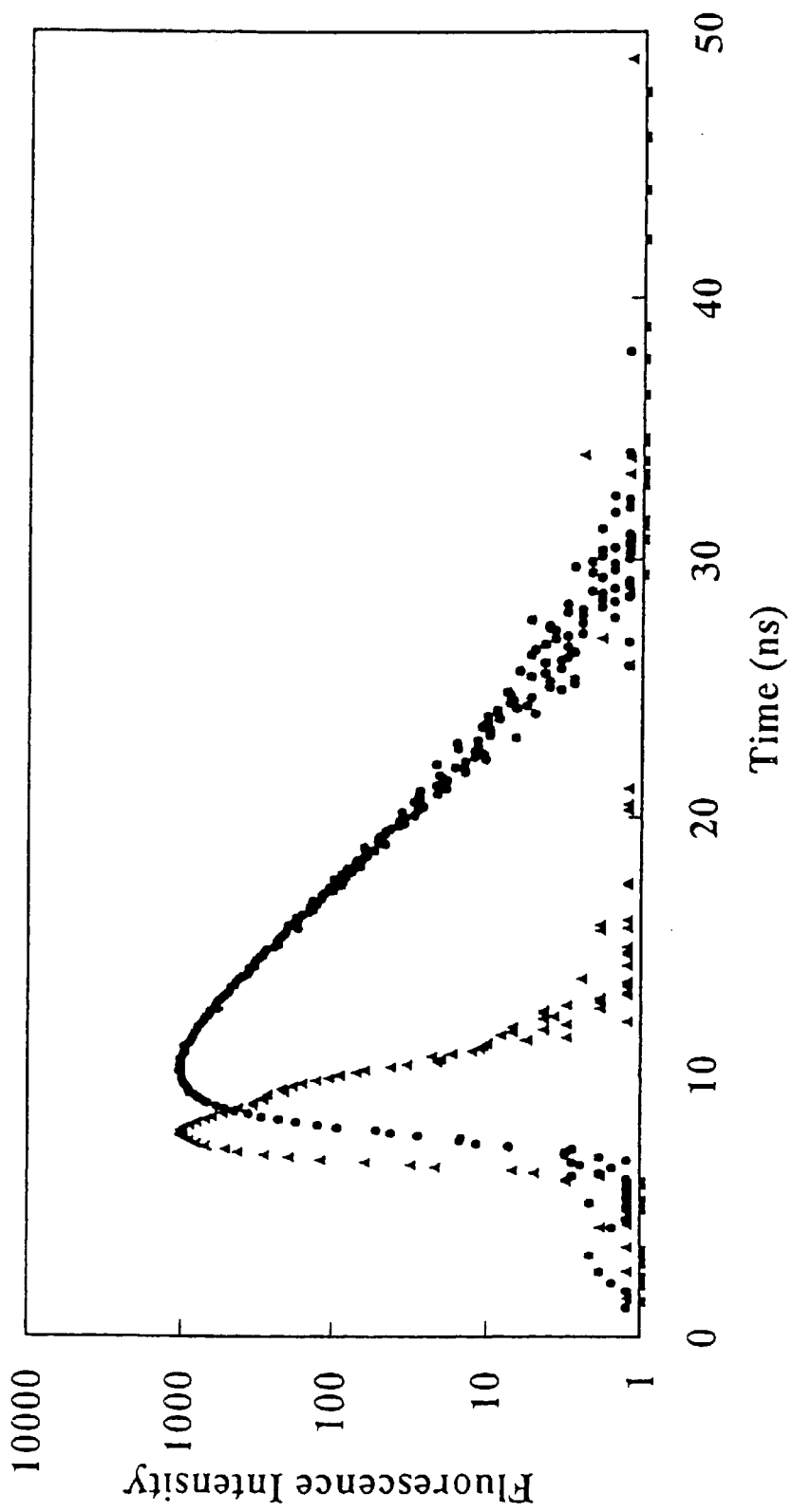
FIG. 22 shows the obtained fluorescence decay curve of a hybrid which was formed with a pair of detection probes and the target DNA (●) when the following pair was used as detection probes. Bodipy 493/503 was used as a donor fluorescent dye, and Cy5 as an acceptor fluorescent dye. The two nucleotides to which the fluorescent dyes bind are spaced by 10 bases (n=10) in a hybrid and its spacing forms a double-strand. (●) denotes the fluorescence decay curve when there were used the detection probes where the labeling position of Bodipy 493/503 in the donor probe was set at a position shifted two bases inside from the position of a gap of the two probes (i.e., the position facing the acceptor probe: the 5'-end of the donor probe) in the hybrid. The labeling position of Cy5 in the acceptor probe is at its position where n equals to 10 (intermediate labeling). (▲) denotes a pulse of excitation light.
Figure 23:
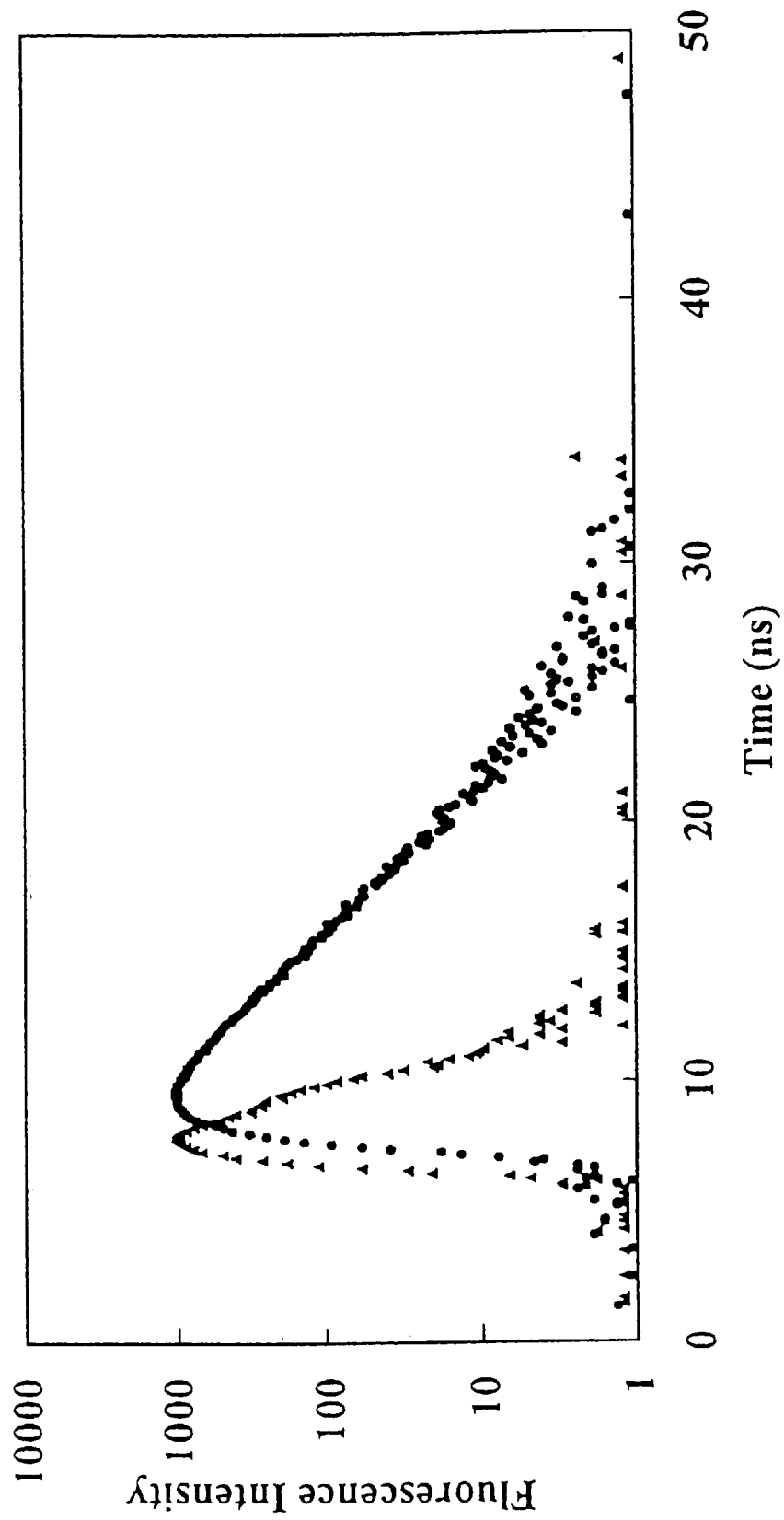
FIG. 23 shows the obtained fluorescence decay curve of a hybrid which was formed with a pair of detection probes and the target DNA (●) when the following pair was used as detection probes. Bodipy 493/503 was used as a donor fluorescent dye, and Cy5 as an acceptor fluorescent dye. The two nucleotides to which the fluorescent dyes bind are spaced by 10 bases (n=10) in a hybrid and its spacing forms a double-strand. (●) denotes the fluorescence decay curve when there were used the detection probes where the labeling position of Bodipy 493/503 in the donor probe was set at a position shifted four bases inside from the position of a gap of the two probes (i.e., the position facing the acceptor probe: the 5'-end of the donor probe) in the hybrid. The labeling position of Cy5 in the acceptor probe is at its position where n equals to 10 (intermediate labeling). (▲) denotes a pulse of excitation light.
Figure 24:
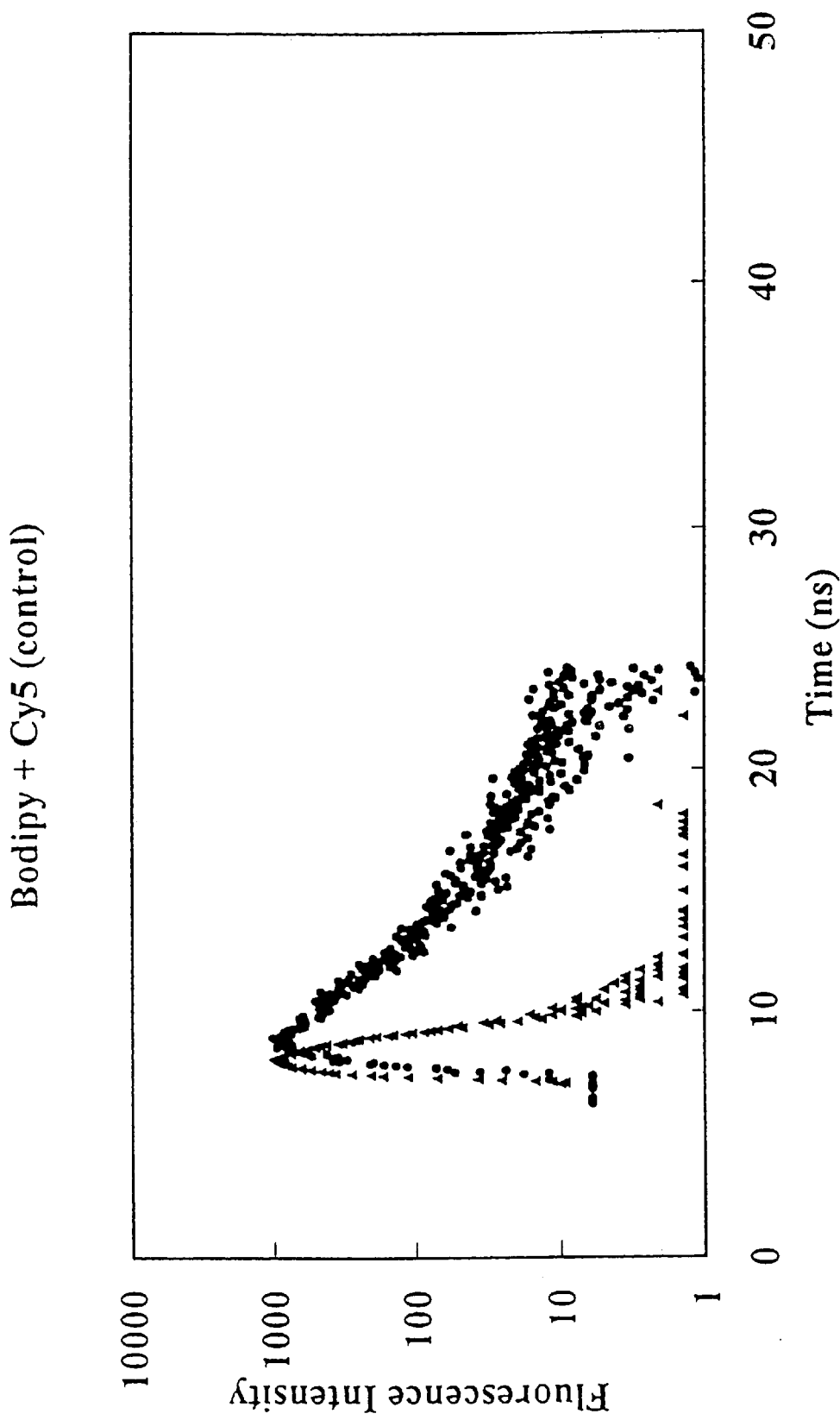
FIG. 24 shows the fluorescence decay curve of the detection probes (specimen DNA not contained), which is a control fluorescence decay curve (●) against FIGS. 20–23. (▲) denotes a pulse of excitation light.

| hybrid | the number of bases from the gap | fluorescence decay curve |
|---|---|---|
| BP0/Cy510/T0 | 0 | FIG. 20 |
| BP1/Cy59/T0 | 1 | FIG. 21 |
| BP2/Cy58/T0 | 2 | FIG. 22 |
| BP4/Cy56/T0 | 4 | FIG. 23 |
| BP0/Cy510 (two kinds of probes were mixed) | | FIG. 24 |

Excitation light: titanium sapphire laser 480 nm (FIG. 24) nitrogen-dye laser 490 nm (FIGS. 20–23) Wavelength region of fluorescence measurements: 650–700 nm.

The "BP0/Cy510" is the sample where BP0 40 pmol and Cy510 40 pmol were dissolved in 200 μl of 20 mM Tris-HCl (pH 9.5) and 0.5 M NaCl.

(d) Fluorescence decay curves in the fluorescence wavelength region of the acceptors (600–650 nm) where the donor fluorescent dyes were Bodipy 493/503 and the acceptor dyes were Cy3.5 and the structures between the two nucleotides to which the fluorescent dyes bound in the hybrids were made double-stranded and the base numbers (n) between the fluorescent dyes in the hybrids were set at n=8, 12, and 16.

Separation, Purification of the Hybrids by High Performance Liquid Chromatography (HPLC)

| donor probe | acceptor probe | specimen DNA | elution time (min) on HPLC |
|---|---|---|---|
| BP0 | Cy358 | T0 | 5.56–5.93 |
| BP0 | Cy3512 | T0 | 5.74–6.35 |
| BP0 | Cy3516 | T0 | 5.65–5.85 |

Fluorescence Decay Curves of the Hybrids

Figure 25:
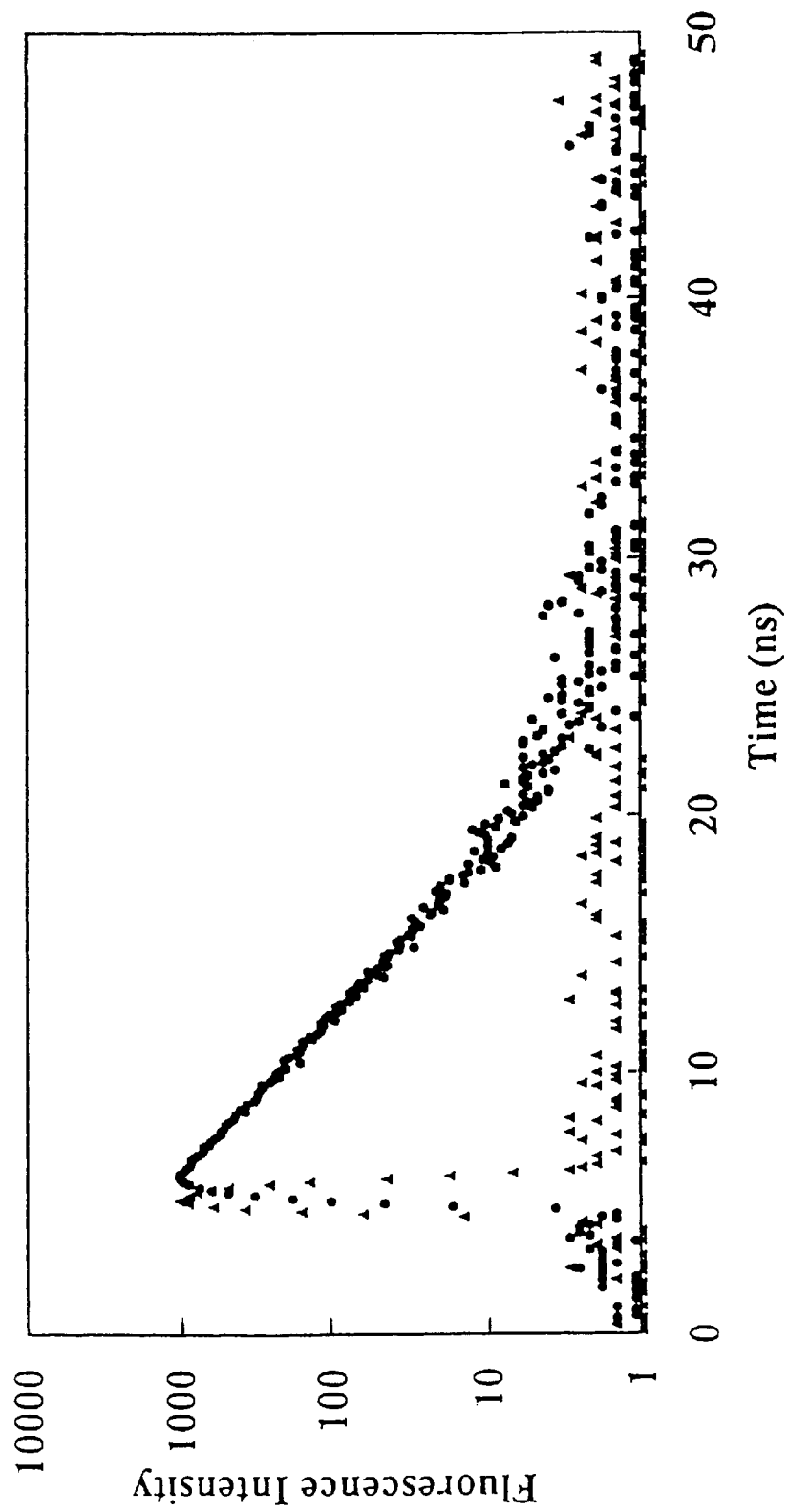
FIG. 25 shows the obtained fluorescence decay curve of a hybrid which was formed with a pair of detection probes and the target DNA (●) when the following pair was used as detection probes. Namely, Bodipy 493/503 was used as a donor fluorescent dye, Cy3.5 as an acceptor fluorescent dye, Bodipy 493/503 was labeled at the 5'-end of the donor probe, and Cy3.5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was eight bases in the hybrid. (▲) denotes a pulse of excitation light.
Figure 26:
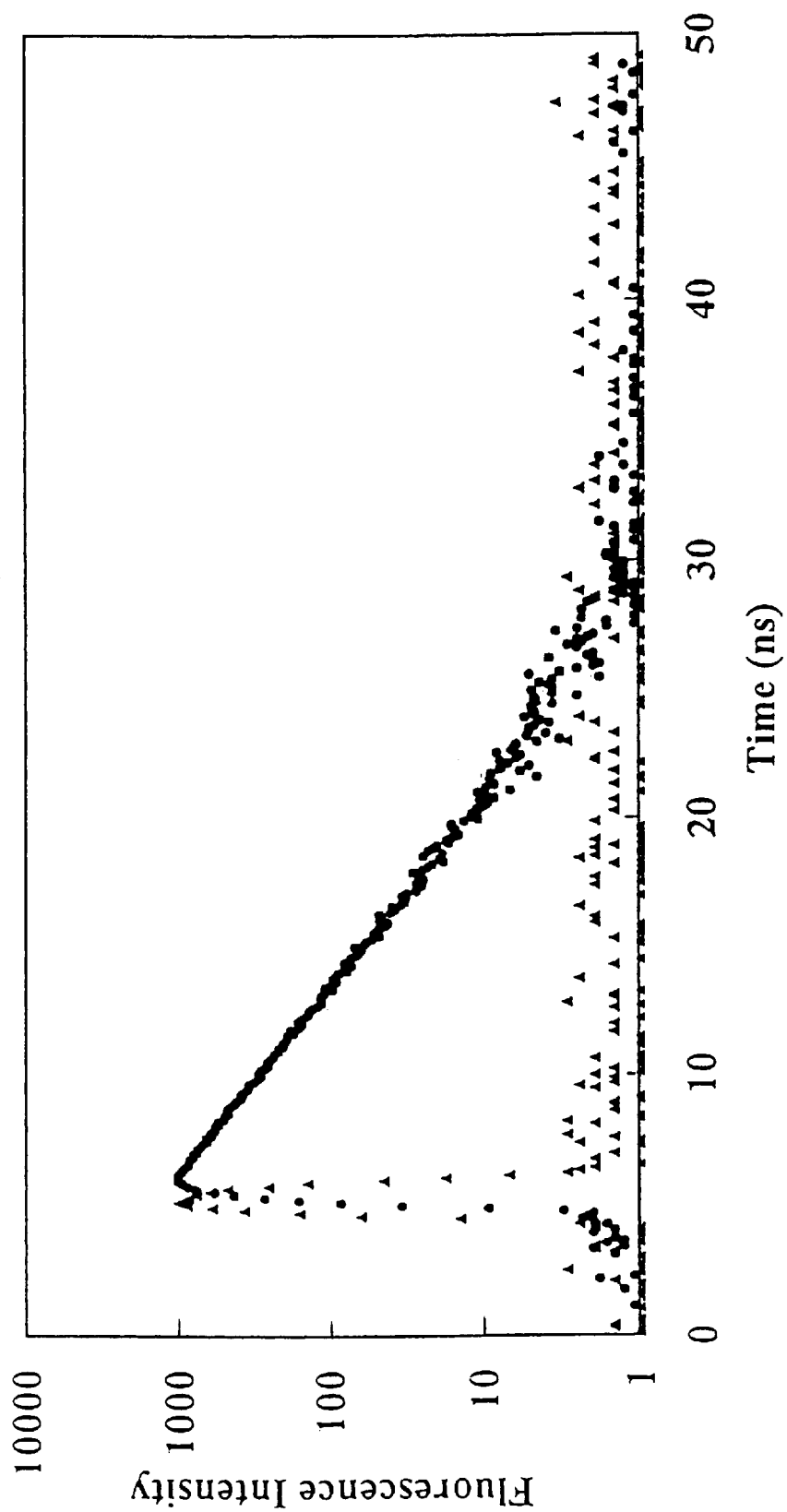
FIG. 26 shows the obtained fluorescence decay curve of a hybrid which was formed with a pair of detection probes and the target DNA (●) when the following pair was used as detection probes. Namely, Bodipy 493/503 was used as a donor fluorescent dye, Cy3.5 as an acceptor fluorescent dye, Bodipy 493/503 was labeled at the 5'-end of the donor probe, and Cy3.5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was 12 bases (n=12) in the hybrid. (▲) denotes a pulse of excitation light.
Figure 27:
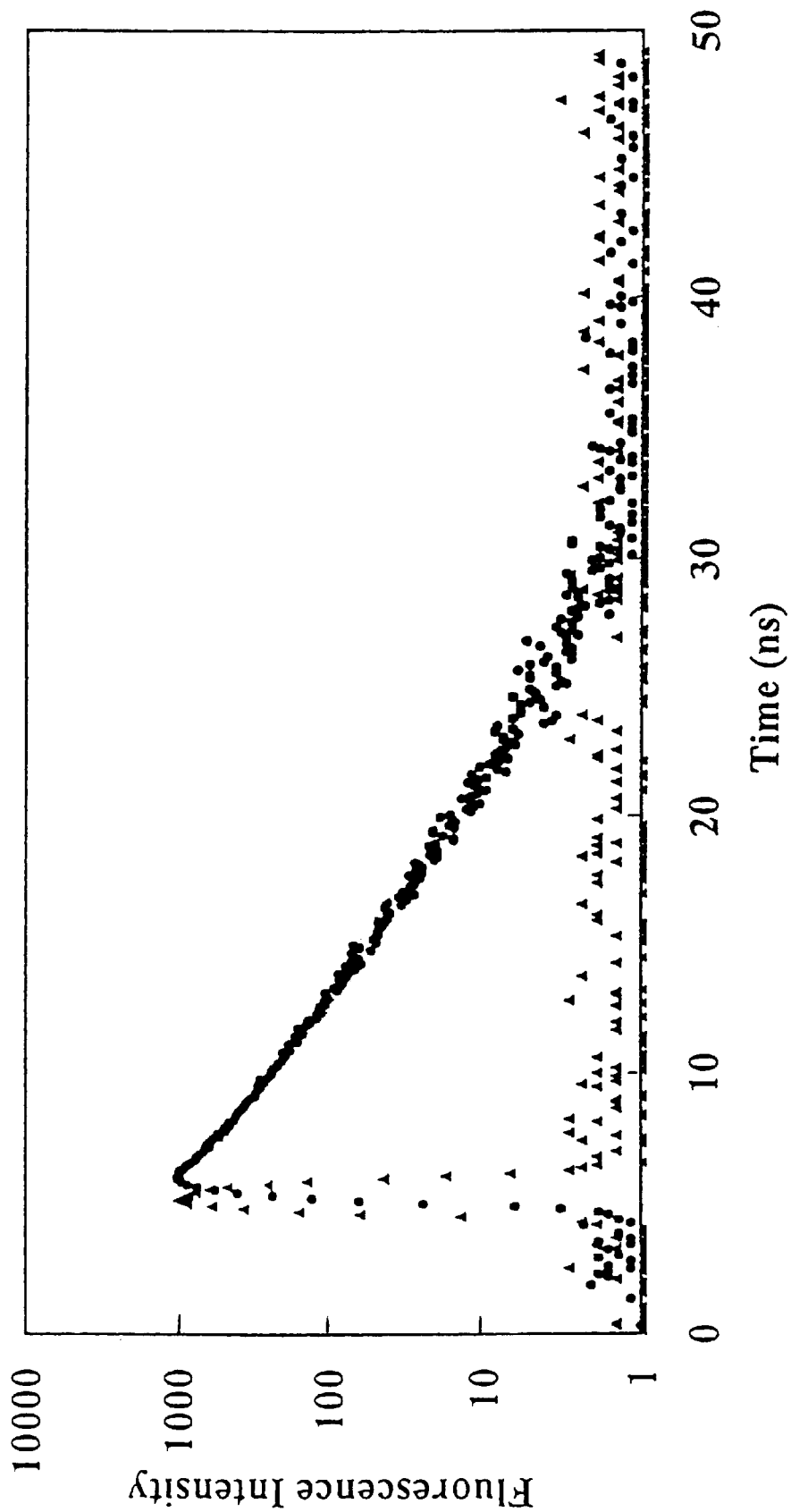
FIG. 27 shows the obtained fluorescence decay curve of a hybrid which was formed with a pair of detection probes and the target DNA (●) when the following pair was used as detection probes. Namely, Bodipy 493/503 was used as a donor fluorescent dye, Cy3.5 as an acceptor fluorescent dye, Bodipy 493/503 was labeled at the 5'-end of the donor probe, and Cy3.5 was labeled to a nucleotide in the middle part of the acceptor probe. Also, the spacing between the two nucleotides to which the fluorescent dyes bind in a hybrid forms a double-strand. (●) denotes the fluorescence decay curve when there were used the detection probes where the base number between the two nucleotides to which the fluorescent dyes bound was 16 bases (n=16) in the hybrid. (▲) denotes a pulse of excitation light.
Figure 28:
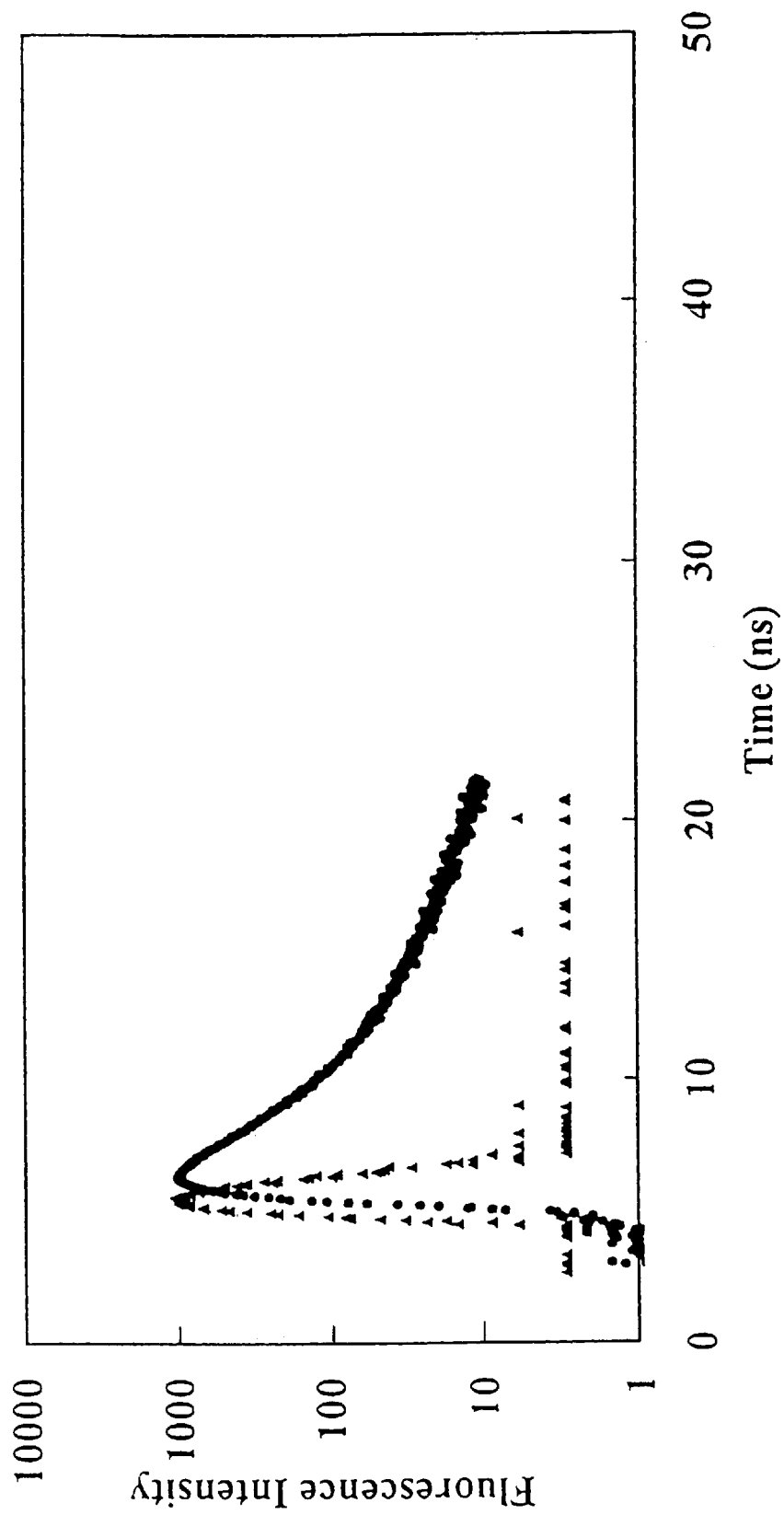
FIG. 28 shows the fluorescence decay curve of the detection probes (specimen DNA not contained), which is a control fluorescence decay curve (●) against FIGS. 25–27. (▲) denotes a pulse of excitation light.

| hybrid | base number (n) between the fluorescent dyes | fluorescence decay curve |
|---|---|---|
| BP0/Cy358/T0 | n = 4 | FIG. 25 |
| BP0/Cy3512/T0 | n = 12 | FIG. 26 |
| BP0/Cy3516/T0 | n = 16 | FIG. 27 |
| BP0/Cy3512/T0 (two kinds of probes were mixed) | | FIG. 28 |

Excitation light: titanium sapphire laser 480 nm Wavelength region of fluorescence measurements: 650–700 nm.

The "BP0/Cy3512" is the sample where BP0 40 pmol and Cy3512 40 pmol were dissolved in 200 μl of 20 mM Tris-HCl (pH 9.5) and 0.5 M NaCl.

(e) Fluorescence decay curves in the fluorescence wavelength region of the acceptors (650–700 nm) where the donor fluorescent dyes were FITC and the acceptor dyes were Cy5 and the structures between the two nucleotides to which the fluorescent dyes bound in the hybrids were made double-stranded and the base numbers (n) between the fluorescent dyes in the hybrids were set at n=10 and 12.

Separation, Purification of the Hybrids by High Performance Liquid Chromatography (HPLC)

| donor probe | acceptor probe | specimen DNA | elution time (min) on HPLC |
|---|---|---|---|
| 5F10 | 5Cy5 | T0 | 8.12–8.89 |
| 5F12 | 5Cy5 | T0 | 6.27–6.73 |

Fluorescence Decay Curves of the Hybrids

Fluorescence decay curves of the hybrids, 5F10/5Cy5/T0 and 5F12/5Cy5/T0, were measured. The fluorescence decay curve of a sample was also measured as control: the sample where 5F 10 40 pmol and 5Cy5 40 pmol were dissolved in 200 μl of 20 mM Tris-HCl (pH 9.5) and 0.5 M NaCl. Delays in the fluorescence decay curves caused by the formation of the hybrids were noted but not distinct (not shown in the figures). Excitation light: nitrogen-dye laser 480 nm Wavelength region of fluorescence measurements: 650–700 nm.

(f) Fluorescence decay curves in the fluorescence wavelength region of the acceptors (650–700 nm) where the donor fluorescent dyes were FITC and the acceptor dyes were Cy5 and the structures between the two nucleotides to which the fluorescent dyes bound in the hybrids were made single-stranded and the base numbers (n) between the fluorescent dyes in the hybrids were set at n=12, 15, and 20.

Separation, Purification of the Hybrids by High Performance Liquid Chromatography (HPLC)

| donor probe | acceptor probe | specimen DNA | elution time (min) on HPLC |
|---|---|---|---|
| 5F | 3Cy5 | T12 | 8.96–9.52 |
| 5F | 3Cy5 | T15 | 8.76–9.49 |
| 5F | 3Cy5 | T20 | 8.87–9.26 |

Fluorescence Decay Curves of the Hybrids

Fluorescence decay curves of the hybrids-5F/3Cy5/T12, 5F/3Cy5/T15, and 5F/3Cy5/T20- were measured. The fluorescence decay curve of a sample was also measured as control: the sample where 5F 40 pmol and 3Cy5 40 pmol were dissolved in 200 μl of 20 mM Tris-HCl (pH 9.5) and 0.5 M NaCl. Delays in the fluorescence decay curves caused by the formation of the hybrids were not particularly noted (not shown in the figures). Excitation light: titanium sapphire laser 480 nm Wavelength region of fluorescence measurements: 650–700 nm.

(g) Fluorescence decay curves in the fluorescence wavelength region of the acceptors (580–630 nm) where the donor fluorescent dyes were FITC and the acceptor dyes were Cy3 and the structures between the two nucleotides to which the fluorescent dyes bound the hybrids were made double-stranded and the base numbers (n) between the fluorescent dyes in the hybrids were set at n=12, 15, and 20.

| Separation, Purification of the Hybrids by High Performance Liquid Chromatography (HPLC) | | | |
|---|---|---|---|
| donor probe | acceptor probe | specimen DNA | elution time (min) on HPLC |
| 3F | 5Cy3 | T12 | 7.45–8.29 |
| 3F | 5Cy3 | T15 | 7.22–8.47 |
| 3F | 5Cy3 | T20 | 7.18–8.07 |

Fluorescence Decay Curves of the Hybrids

Fluorescence decay curves of the hybrids-3F/5Cy3/T12, 3F/5Cy3/T15, and 3F/5Cy3/T20- were measured. The fluorescence decay curve of a sample was also measured as control: the sample where 3F 40 pmol and 5Cy3 40 pmol were dissolved in 200 μl of 20 mM Tris-HCl (pH 9.5) and 0.5 M NaCl. Delays in the fluorescence decay curves caused by the formation of the hybrids were not particularly noted (not shown in the figures). Excitation light: titanium sapphire laser 480 nm Wavelength region of fluorescence measurements: 580–630 nm.

(h) Fluorescence decay curves in the fluorescence wavelength region of the acceptors (580–630 nm) where the donor fluorescent dyes were FITC and the acceptor dyes were Cy3 and the structures between the two nucleotides to which the fluorescent dyes bound in the hybrids were made double-stranded and the base numbers (n) between the fluorescent dyes in the hybrids were set at n=10, 13, and 15.

| Separation, Purification of the Hybrids by High Performance Liquid Chromatography (HPLC) | | | |
|---|---|---|---|
| donor probe | acceptor probe | specimen DNA | elution time (min) on HPLC |
| 5F10 | 5Cy3 | T0 | 7.54–7.75 |
| 5F13 | 5Cy3 | T0 | 7.23–7.45 |
| 5F15 | 5Cy3 | T0 | 7.24–7.76 |

Fluorescence Decay Curves of the Hybrids

Fluorescence decay curves of the hybrids-5F10/5Cy3/T0, 5F/5Cy3/T0, and 5F15/5Cy3/T0- were measured. The fluorescence decay curve of a sample was also measured as control: the sample where 5F10 40 pmol and 5Cy3 40 pmol were dissolved in 200 μl of 20 mM Tris-HCl (pH 9.5) and 0.5 M NaCl. Delays in the fluorescence decay curves caused by the formation of the hybrids were not particularly noted (not shown in the figures). Excitation light: titanium sapphire laser 480 nm wavelength region of fluorescence measurements: 580–630 nm.

(i) Fluorescence decay curve in the fluorescence wavelength region of the acceptor (600–650 nm) where the donor fluorescent dye was FITC and the acceptor dye was XRITC and the structure between the two nucleotides to which the fluorescent dyes bound in the hybrid was made double-stranded and the base number (n) between the fluorescent dyes in the hybrid was set at n=15.

| Separation, Purification of the Hybrid by High Performance Liquid Chromatography (HPLC) | | | |
|---|---|---|---|
| donor probe | acceptor probe | specimen DNA | elution time (min) on HPLC |
| 5F15 | 5R16 | T0 | 6.75–7.53 |

Fluorescence Decay Curve of the Hybrid

The fluorescence decay curve of the hybrid, 5F15/5R16/T0 was measured. The fluorescence decay curve of a sample was also measured as control: the sample where 5F15 40 pmol and 5R16 40 pmol were dissolved in 200 μl of 20 mM Tris-HCl (pH 9.5) and 0.5 M NaCl. A delay in the fluorescence decay curve caused by the formation of the hybrid was not particularly noted (not shown in the figures). Excitation light: titanium sapphire laser 480 nm Wavelength region of fluorescence measurement: 600–650 nm.

(j) Fluorescence decay curves in the fluorescence wavelength region of the acceptors (600–650 nm) where the donor fluorescent dyes were FITC and the acceptor dyes were XRITC. and the structures between the two nucleotides to which the fluorescent dyes bound in the hybrids were made single-stranded and the base numbers (n) between the fluorescent dyes in the hybrids were set at n=4, 8, 12, 15, and 20.

These samples were not separated with a high performance liquid column chromatogram and their fluorescence decay curves were measured on samples in which the probes and specimen DNAs were mixed. The fluorescence decay curve of a sample was also measured as control: the sample where 3F 40 pmol and 5R16 40 pmol were dissolved in 200 μl of 20 mM Tris-HCl (pH 9.5) and 0.5 M NaCl. Delays in the fluorescence decay curves caused by the formation of the hybrids were not particularly noted (not shown in the figures). Excitation light: titanium sapphire laser 480 nm Wavelength region of fluorescence measurements: 600–650 nm.

| donor probe | acceptor probe | specimen DNA |
|---|---|---|
| 3F | 5R16 | T4 |
| 3F | 5R16 | T8 |
| 3F | 5R16 | T12 |
| 3F | 5R16 | T15 |
| 3F | 5R16 | T20 |

(k) Fluorescence decay curves in the fluorescence wavelength region of the acceptors (650–700 nm) where the donor fluorescent dyes were Bodipy 493/503 and the acceptor dyes were Cy5 and the structures between the two nucleotides to which the fluorescent dyes bound in the hybrids were made single-stranded and the base numbers (n) between the fluorescent dyes in the hybrids were set at n=4, 8, 10, 12, 15, and 20.

Bodipy 493/503 is labeled to the 5'-end positions of the donor probes and Cy5 is labeled to middle parts of the acceptor probes.

Separation, Purification of the Hybrids by High Performance Liquid Chromatography (HPLC)

| donor probe | acceptor probe | specimen DNA | elution time (min) on HPLC |
|---|---|---|---|
| BP0 | 3Cy5 | T4 | 7.02–7.59 |
| BP0 | 3Cy5 | T8 | 7.37–8.10 |
| BP0 | 3Cy5 | T10 | 8.74–9.32 |
| BP0 | 3Cy5 | T12 | 8.91–9.22 |
| BP0 | 3Cy5 | T15 | 8.83–9.18 |
| BP0 | 3Cy5 | T20 | 8.69–9.17 |

Fluorescence Decay Curves of the Hybrids

Figure 29:
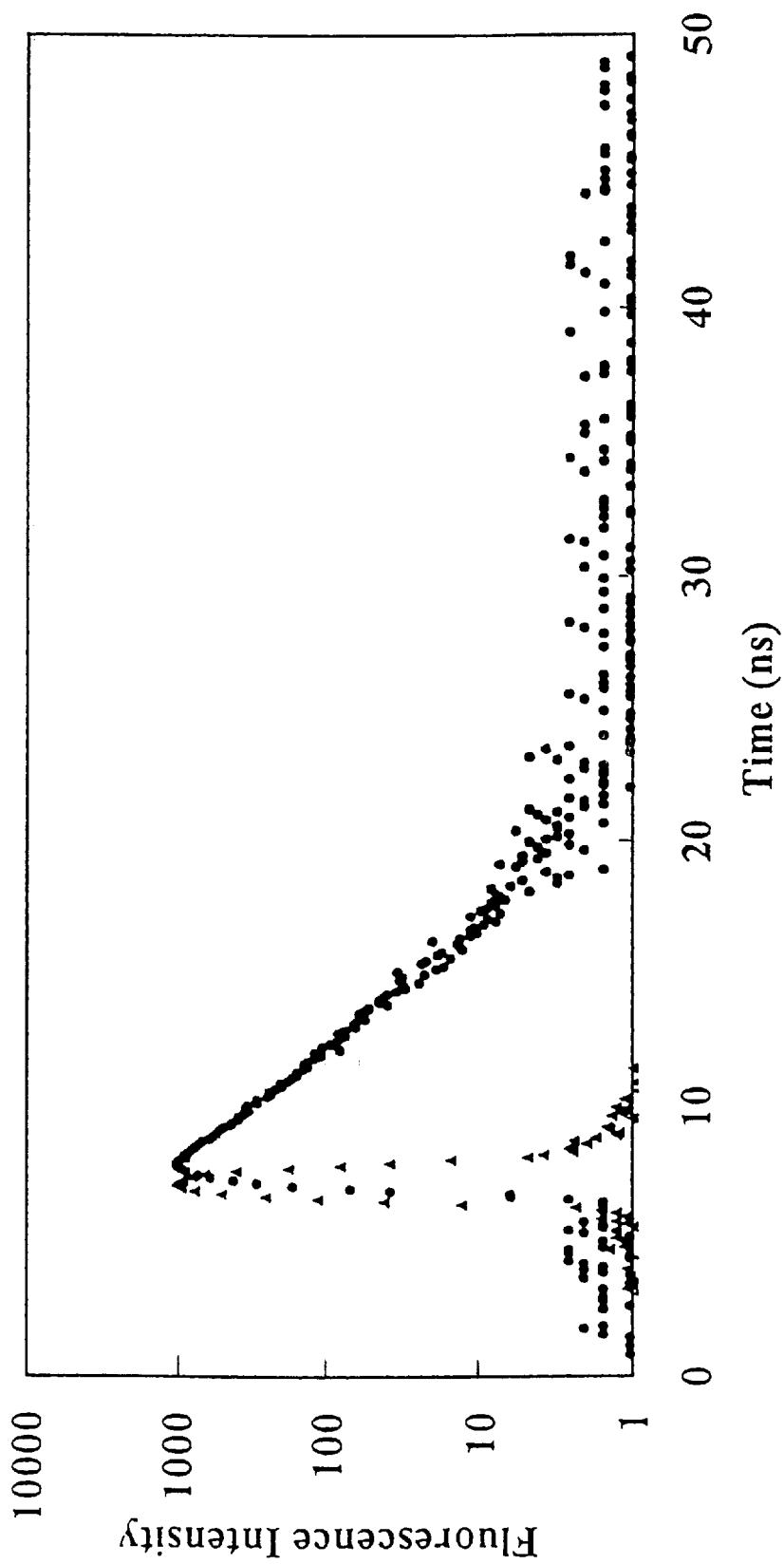
FIG. 29 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a single-strand. (●) denotes the fluorescence decay curve when there were used the detection probes where the base number between the two nucleotides to which the fluorescent dyes bound was four bases (n=4) in the hybrid. (▲) denotes a pulse of excitation light.
Figure 30:
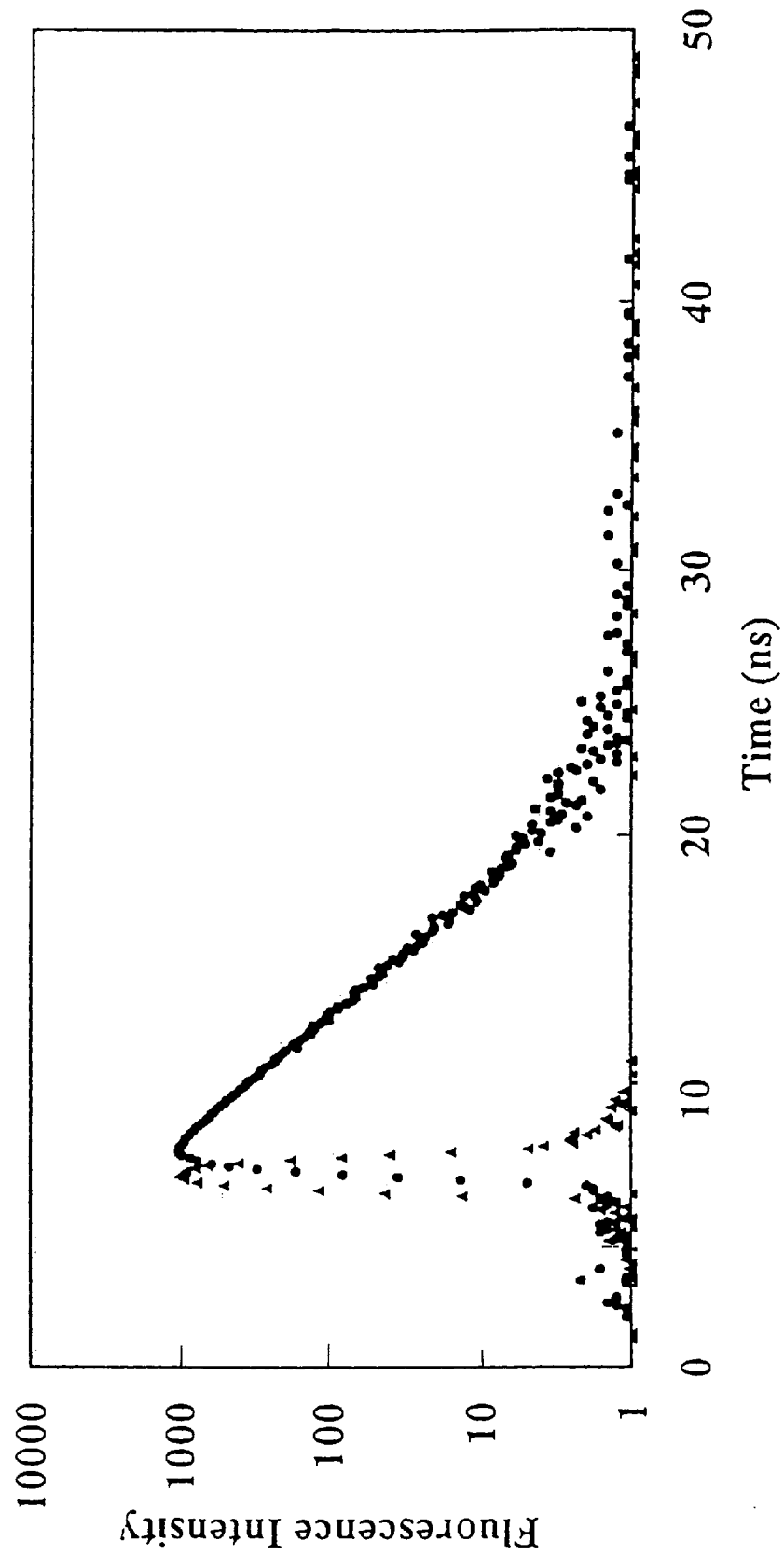
FIG. 30 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a single-strand. (●) denotes the fluorescence decay curve when there were used the detection probes where the base number between the two nucleotides to which the fluorescent dyes bound was eight bases (n=8) in the hybrid. (▲) denotes a pulse of excitation light.
Figure 31:
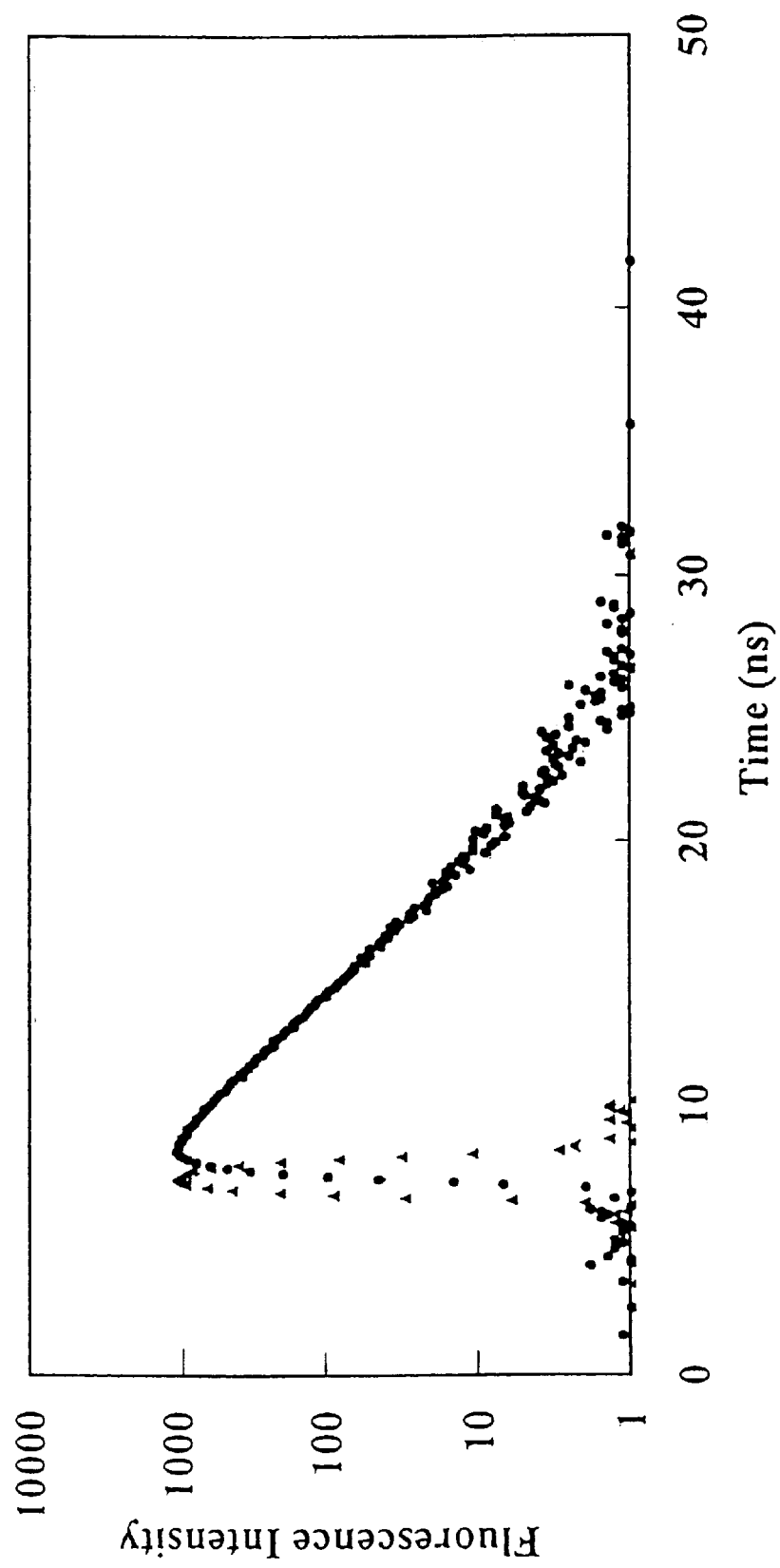
FIG. 31 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a single-strand. (●) denotes the fluorescence decay curve when there were used the detection probes where the base number between the two nucleotides to which the fluorescent dyes bound was 10 bases (n=10) in the hybrid. (▲) denotes a pulse of excitation light.
Figure 32:
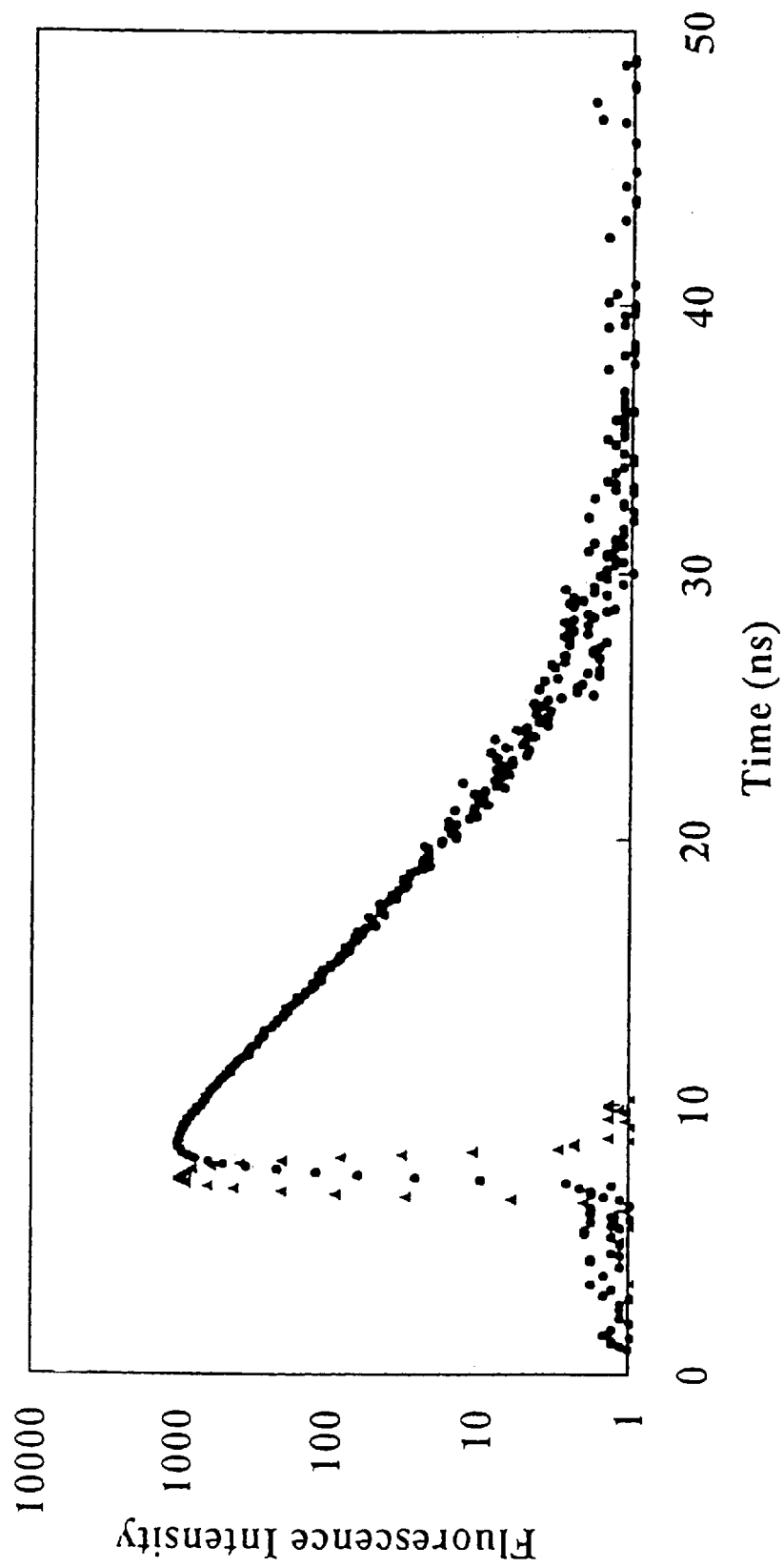
FIG. 32 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a single-strand. (●) denotes the fluorescence decay curve when there were used the detection probes where the base number between the two nucleotides to which the fluorescent dyes bound was 12 bases (n=12) in the hybrid. (▲) denotes a pulse of excitation light.
Figure 33:
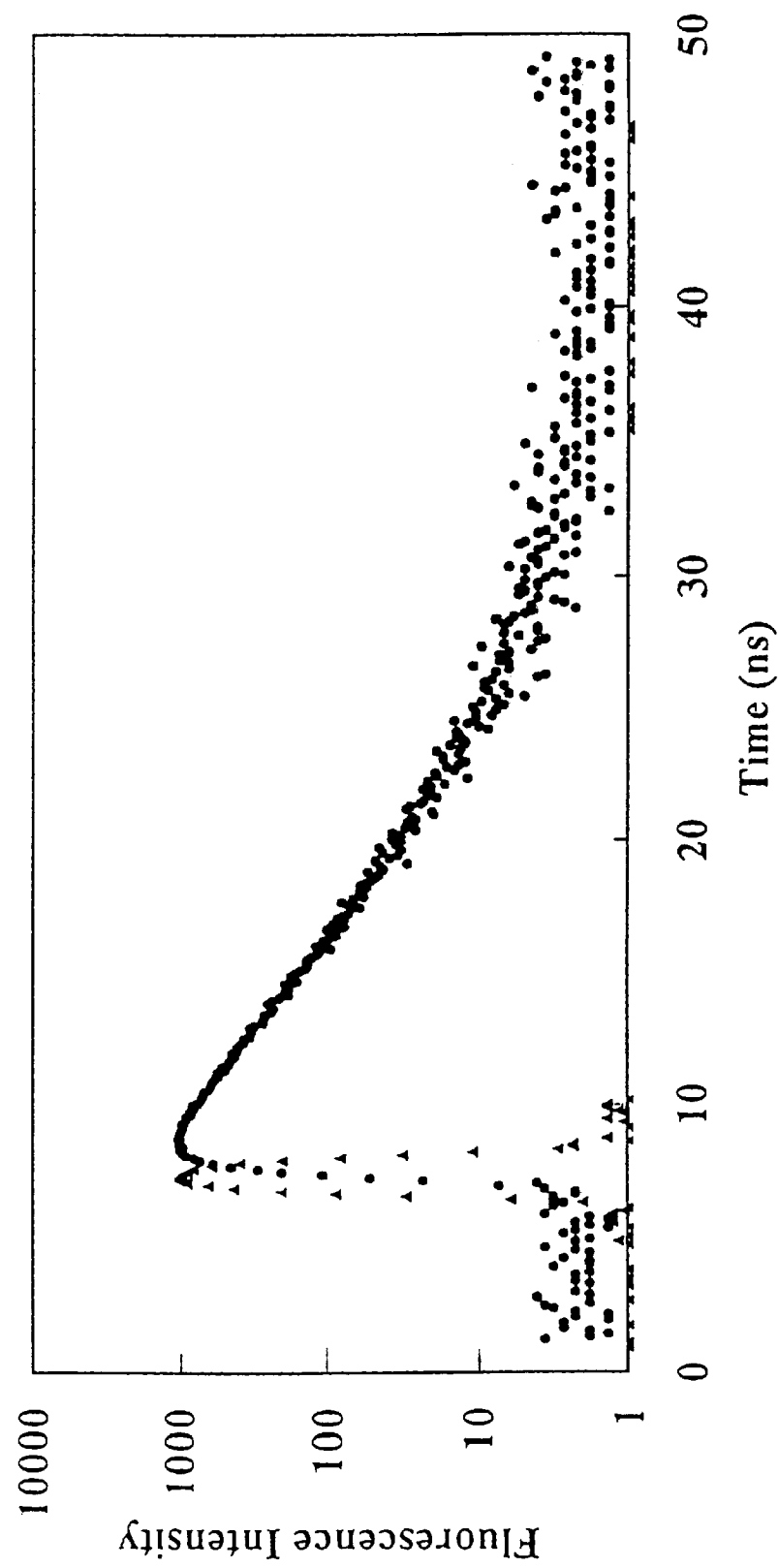
FIG. 33 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a single-strand. (●) denotes the fluorescence decay curve when there were used the detection probes where the base number between the two nucleotides to which the fluorescent dyes bound was 15 bases (n=15) in the hybrid. (▲) denotes a pulse of excitation light.
Figure 34:
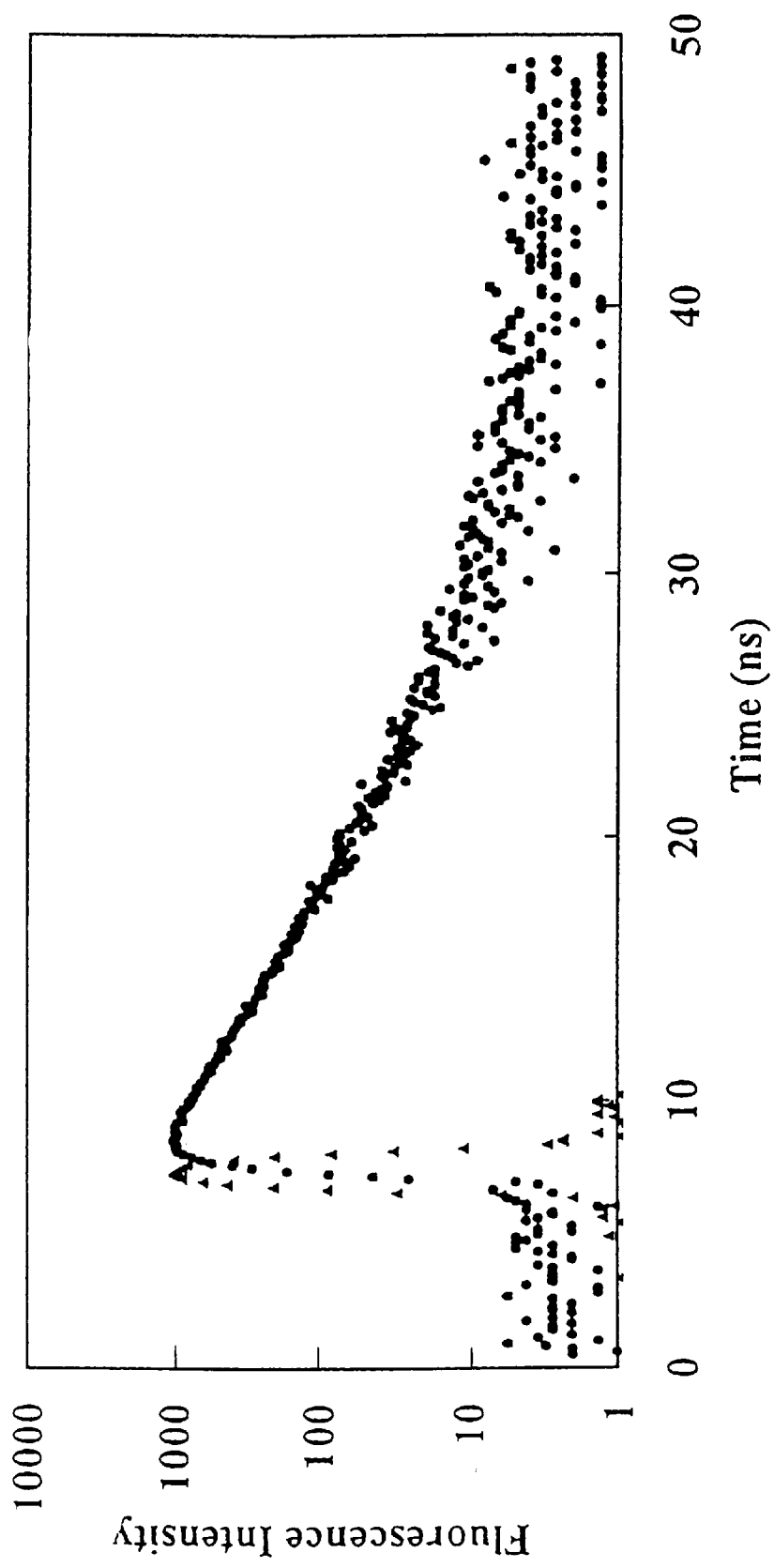
FIG. 34 shows the obtained fluorescence decay curve of a hybrid which was formed with a pair of detection probes and the target DNA (●) when the following pair was used as detection probes. Namely, Bodipy 493/503 was used as a donor fluorescent dye, Cy5 as an acceptor fluorescent dye, Bodipy 493/503 was labeled at the 5'-end of the donor probe, and Cy5 was labeled to a nucleotide in the middle part of the acceptor probe. Also, the spacing between the two nucleotides to which the fluorescent dyes bind in a hybrid forms a single-strand. (●) denotes the fluorescence decay curve when there were used the detection probes where the base number between the two nucleotides to which the fluorescent dyes bound was 20 bases (n=20) in the hybrid. (▲) denotes a pulse of excitation light.

| hybrid | base number (n) between the fluorescent dyes | fluorescence decay curve |
|---|---|---|
| BP0/3Cy5/T4 | n = 4 | FIG. 29 |
| BP0/3Cy5/T8 | n = 8 | FIG. 30 |
| BP0/3Cy5/T10 | n = 10 | FIG. 31 |
| BP0/3Cy5/T12 | n = 12 | FIG. 32 |
| BP0/3Cy5/T15 | n = 15 | FIG. 33 |
| BP0/3Cy5/T20 | n = 20 | FIG. 34 |

Figure 35:
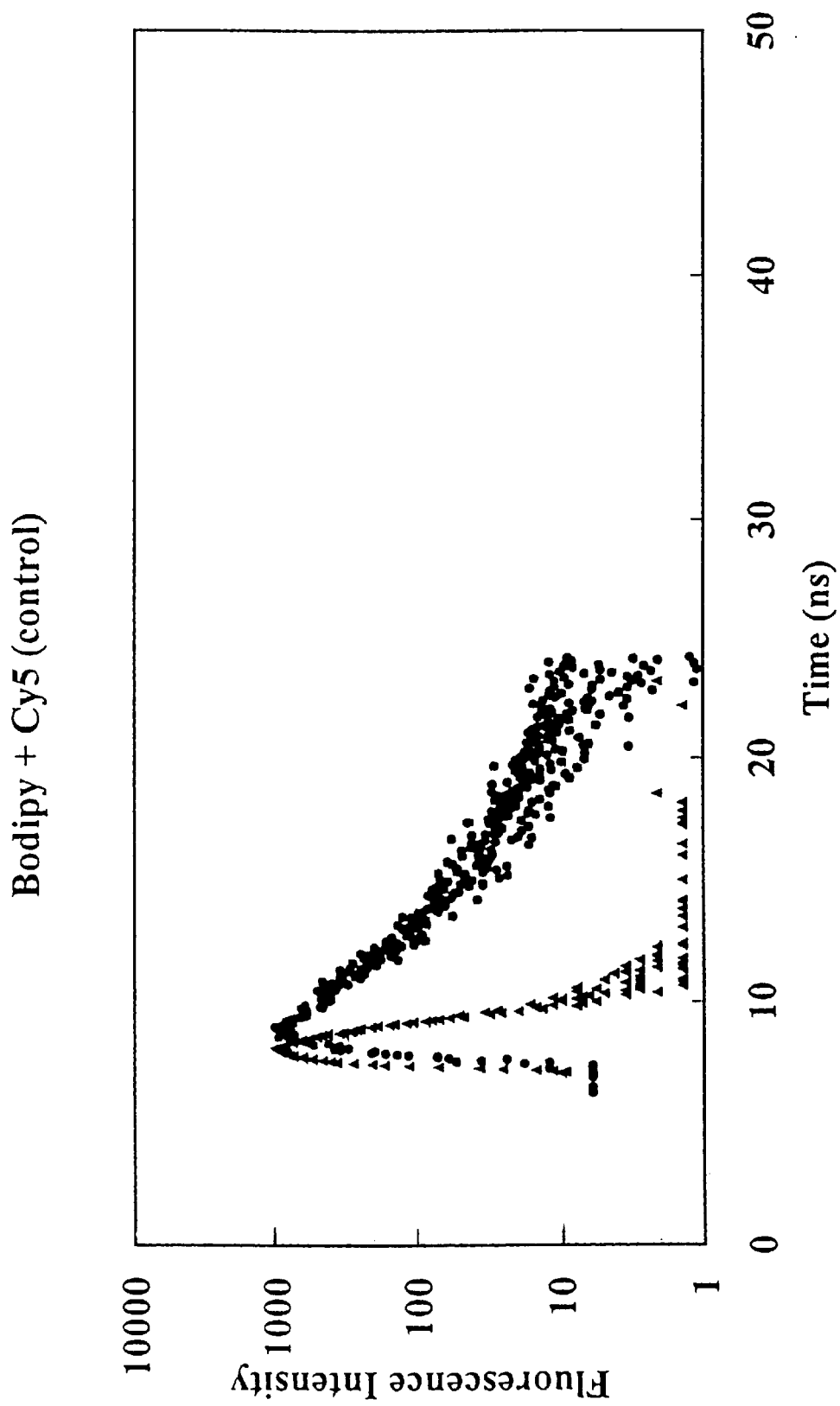
FIG. 35 shows the fluorescence decay curve of the detection probes (specimen DNA not contained), which is a control fluorescence decay curve (●) against FIGS. 29–34. (▲) denotes a pulse of excitation light.

FIG. 35 represents the fluorescence decay curve of the sample where BP0 40 pmol and Cy510 40 pmol were dissolved in 200 μl of 20 mM Tris-HCl (pH 9.5) and 0.5 M NaCl. Excitation light: titanium sapphire laser 480 nm (FIGS. 29–34) nitrogen-dye laser 490 nm (FIG. 35) Wavelength region of fluorescence measurements: 650–700 nm.

2. Detection of Specimen in a Sample Where Detection Probes Are Present in Excess Relative to the Specimen (1) Synthesis of the Probes Fluorescent labeled oligo-DNAs and fluorescent labeled oligonucleotides of the phosphorothioate type (S-oligo) having base sequences as described below were synthesized according to the procedures as described in the foregoing "1. Detection Probes (1) Synthesis of the Detection Probes."

Oligo-DNAs labeled with Bodipy 493/503

```
BP0:  5'-XAGCGCGCAATTAACCC-3'   (SEQ ID NO:51)

D1:   5'-XTCTAGTTGGTCTGTC-3'    (SEQ ID NO:52)
```

In BP0 and D1 as described above, "X" denotes the position to which Bodipy 493/503 binds.

S-Oligo labeled with Bodipy 493/503

```
D2: 5'-XTCTAGTTGGTCTGT-3'   (SEQ ID NO:53)
```

In D2 as described above, "X" denotes the position to which Bodipy 493/503 binds.

Oligo-DNAs labeled with Cy5

```
Cy512:  5'-GCTAXGACCATGATTAC-3'   (SEQ ID NO:54)

A1:     5'-GCAXACTTCXTCATCT-3'    (SEQ ID NO:55)
```

In Cy 512 and A1 as described above, "X" denotes the position to which Cy5 binds.

S-Oligo labeled with Cy5

```
A2: 5'-GCAGAXCTTCTCATCT-3'   (SEQ ID NO:56)
```

In A2 as described above, "X" denotes the position to which Cy5 binds.

(2) Synthesis of Specimen DNAs and RNAs

Specimen DNAs and RNAs having the base sequences as described below were synthesized according to the procedures as described in the foregoing "1. Detection Probes (2) Synthesis of Specimen DNAs."

Specimen DNA (T0)

```
Specimen DNA (T0)
5'-GGGTTAATTGCGCGCTGTAATCATGGTCATAGC-3'
(SEQ ID NO:57)

Specimen RNA (RT1)
5'-GACAGACCAACUAGAAGAUGAGAAGUCUGC-3'
(SEQ ID NO:58)
```

(3) Preparation of Samples for Measurement and Measurements of Fluorescence Spectra and Fluorescence Decay Curves A pair of detection probes consisting of a donor probe and an acceptor probe (each 200 pmol) and varying concentrations of a specimen were mixed in 200 μl of 1×SSC buffer (15 mM $Na_3$citrate, pH 7.0, 150 mM NaCl) and allowed to react at room temperature for 10 min. Subsequently, fluorescence spectra and fluorescence decay curves were measured.

Measurements of Fluorescence Spectra Fluorescence spectrophotometer: Hitachi F-4500 Excitation wavelength: 490 nm Recording wavelength of fluorescence spectra: 500–750 nm.

Measurements of fluorescence decay curves Picosecond fluorescence lifetime recording device C4780 (Hamamatsu Photonics Co. Ltd.) Excitation light sources:

1. Argon laser excitation titanium sapphire laser (Spectra Physics Inc.)
   Argon ion laser: Model 2080
   Mode-lock titanium sapphire laser: TSUNAMI Frequency doubler/pulse selector: Model 3980
2. Nitrogen-dye laser (Laser Photonics) nitrogen laser: Model LN1200
   Dye: COUMARIN 307
   Wavelength region for fluorescence measurements: 650–700 nm (a) For the detection probe in order to detect a DNA that serves as a specimen, there is used a pair of oligo-DNAs: the donor fluorescent dye is Bodipy 493/503 and the acceptor dye is Cy5; the spacing between the two nucleotides to which the fluorescent dyes bind adopts a double-stranded structure when the hybrid is formed and the base number (n) for the spacing is set at 12 (n=12); and the Bodipy 494/503 is bound to the nucleotide locating at the gap of the hybrid.

| donor probe | acceptor probe | speicmen | fluorescence decay curve | fluorescence spectrum |
|---|---|---|---|---|
| BP0 | Cy512 | T0 | FIG. 4 | FIG. 5 |

Fluorescence Decay Curves (FIG. 4)

| number in the figure | amount of detection probe | amount of specimen DNA | molar ratio (Specimen DNA/probe) |
|---|---|---|---|
| 1 | 200 pmol | 0 | 0 |
| 2 | 200 pmol | 2 pmol | 1% |
| 3 | 200 pmol | 6 pmol | 3% |
| 4 | 200 pmol | 10 pmol | 5% |
| 5 | 200 pmol | 40 pmol | 20% |

As is evident from FIG. 4, with increasing amounts of the specimen DNA the decay curves are more delayed. In the figure, decay curve 1 (a sample containing no specimen) and decay curve 2 (a sample containing the specimen DNA with its content being 1% as a molar ratio relative to the probe) are unambiguously distinguishable and even if the detection probe are present in 1000-fold excess, detection of the specimen is feasible.

Fluorescence Spectra (FIG. 5)

| number in the figure | amount of detection probe | amount of specimen DNA | molar ratio (Specimen DNA/probe) |
|---|---|---|---|
| 1 | 200 pmol | 0 | 0 |
| 2 | 200 pmol | 2 pmol | 1% |
| 3 | 200 pmol | 6 pmol | 3% |
| 4 | 200 pmol | 10 pmol | 5% |
| 5 | 200 pmol | 40 pmol | 20% |

In the fluorescence spectrum, spectra 1–3 are practically indistinguishable, and it is also difficult to recognize any changes in the spectra 1 and 4.

(b) For the detection probe in order to detect a RNA that serve as a specimen, there is used a pair of oligo-DNAs: the donor fluorescent dye is Bodipy 493/503 and the acceptor dye is Cy5; the spacing between the two nucleotides to which the fluorescent dyes bind adopts a double-stranded structure when the hybrid is formed; and the Bodipy 494/503 is bound to the nucleotide locating at the gap of the hybrid.

Figure 37:
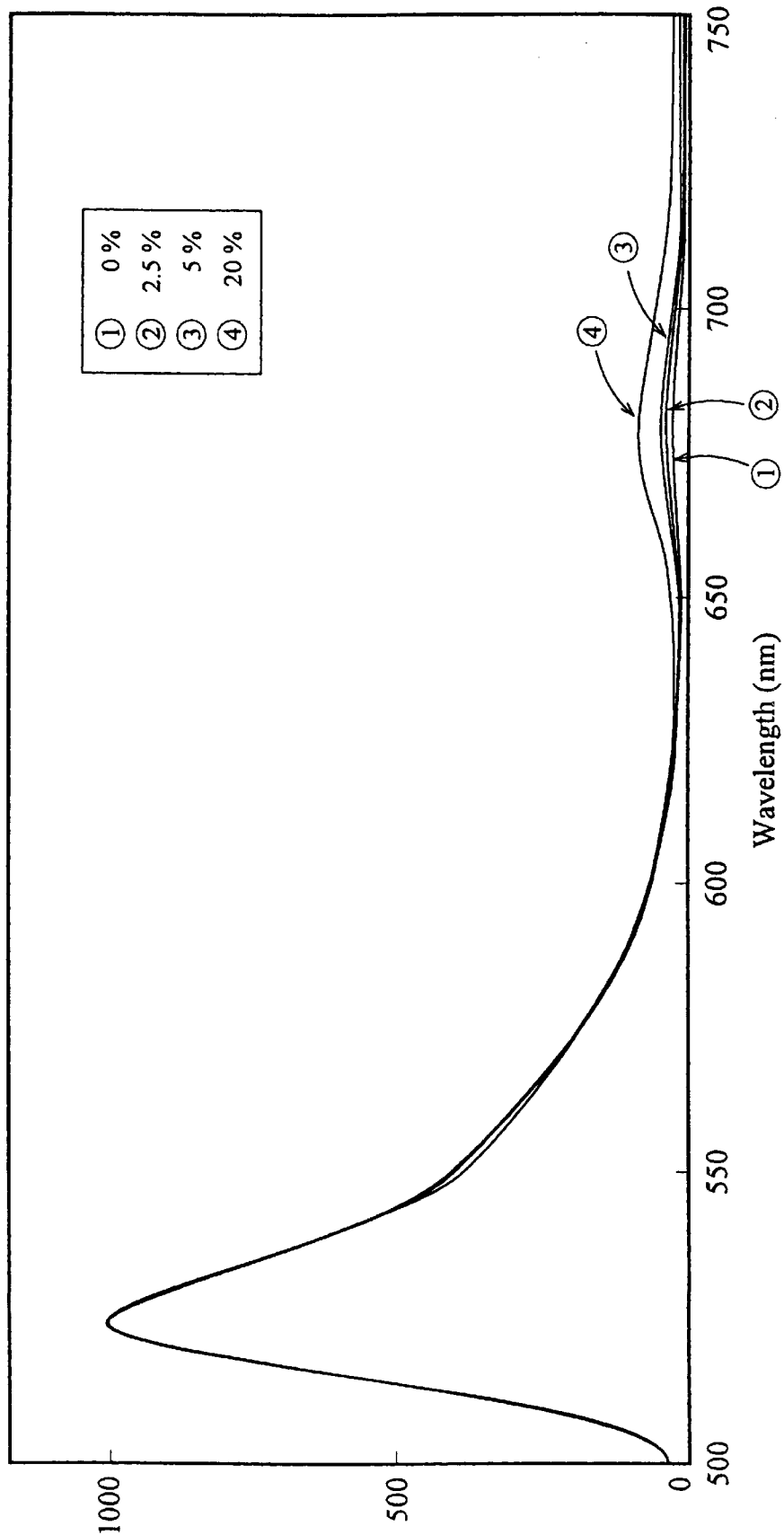
FIG. 37 shows the fluorescence spectra of the samples shown in FIG. 36: a pair of detection probes and a target RNA to be the. specimen were mixed in such varying proportions as to render the probes excessive. The detection probes used are as follows: the donor fluorescent dye is Bodipy 493/503 and the acceptor fluorescent dye is Cy5; at the time of hybrid formation the spacing between the nucleotide to which the donor fluorescent dye bind and the nucleotide to which the acceptor fluorescent dye bind is double-stranded; and the base number for the spacing is 12 (n=12). The proportions of the target RNA to the probes are: (1) 0%, (2) 2.5%, (3) 5%, and (4) 20% (target RNA/probe, molar ratio).

| donor probe | acceptor probe | specimen | base number between the two dyes | fluorescence decay curve | fluorescence spectrum |
|---|---|---|---|---|---|
| D1 | A1 | RT1 | n = 12 | FIG. 36 | FIG. 37 |

Fluorescence Decay Curves (FIG. 36)

| number in figure | amount of detection probe | amount of specimen RNA | molar ratio (Specimen/ probe) |
|---|---|---|---|
| 1 | 200 pmol | 0 | 0 |
| 2 | 200 pmol | 5 pmol | 2.5% |
| 3 | 200 pmol | 10 pmol | 5% |
| 4 | 200 pmol | 40 pmol | 20% |

Fluorescence Spectra (FIG. 37)

| number in figure | amount of detection probe | amount of specimen RNA | molar ratio (Specimen/ probe) |
|---|---|---|---|
| 1 | 200 pmol | 0 | 0 |
| 2 | 200 pmol | 5 pmol | 2.5% |
| 3 | 200 pmol | 10 pmol | 5% |
| 4 | 200 pmol | 40 pmol | 20% |

As is shown in FIG. 36, with increasing amounts of the specimen RNA the decay curves are more delayed. From the figure, it is apparent that even under the conditions where the detection probes are present in large excess relative to the specimen RNA, detection of the specimen RNA is feasible.

(c) For the detection probe in order to detect a RNA that serves as a specimen, there is used a pair of oligo-DNAs of the phosphothioate type: the donor fluorescent dye is Bodipy 493/503 and the acceptor dye is Cy5; the spacing between the two nucleotides to which the fluorescent dyes bind adopts a double-stranded structure when the hybrid is formed; and the Bodipy 494/503 is bound to the nucleotide locating at the gap of the hybrid.

| donor probe | acceptor probe | specimen | base number between two dyes | fluorescence decay curve |
|---|---|---|---|---|
| D2 | A2 | RT1 | n = 10 | FIG. 38 |

Fluorescence Decay Curves (FIG. 38)

| number in figure | amount of detection probe | amount of specimen RNA | molar ratio (Specimen/ probe) |
|---|---|---|---|
| 1 | 200 pmol | 0 | 0 |
| 2 | 200 pmol | 5 pmol | 2.5% |
| 3 | 200 pmol | 10 pmol | 5% |
| 4 | 200 pmol | 40 pmol | 20% |

As is shown in FIG. 38, with increasing amounts of the specimen RNA the decay curves are more delayed. From the figure, it is apparent that even if under the conditions where the detection probes are present in large excess relative to the specimen RNA, detection of the specimen RNA is feasible.

INDUSTRIAL APPLICABILITY

This invention has developed detection probes and method of detection that will enable the detection of DNAs and RNAs having specified base sequences contained in a specimen sample with great ease, accuracy, and high sensivity. It is anticipated that if the detection probes and method of detection according to this invention are applied to gene diagnosis, cell diagnosis and the like, they will exercise great power. It is also expected that by applying the detection probe and method of detection according to this invention to experimental protocols in the field of genetic engineering such as gene cloning, experimental techniques in said filed will be advanced immensely.

What is claimed is:

1. A pair of detection probes for detecting a specimen having a specified polynucleotide base sequence in a sample suspected of containing the specimen, said pair of detection probes comprising:

a donor probe to which a first fluorescent dye molecule is covalently bound, having a base sequence capable of hybridizing with a part of the polynucleotide base sequence; and an acceptor probe to which a second fluorescent dye molecule is covalently bound, having a base sequence capable of hybridizing with a part of the polynucleotide base sequence, wherein if any hybrid is formed among the donor probe, the acceptor probe, and the specimen, then the hybrid at least partially adopts a double-stranded structure between a first nucleotide position to which the first fluorescent dye molecule of the donor probe is bound and a second nucleotide position to which the second fluorescent dye molecule of the acceptor probe is bound, wherein a base number between the first nucleotide position and the second nucleotide position is from 8 to 16 in the hybrid, and further wherein a fluorescence decay curve of fluorescence intensity in a wavelength region of fluorescence resulting from the second fluorescent dye molecule significantly changes due to resonance energy transfer from the donor probe to the acceptor probe when the hybrid has been formed.

2. The detection probes of claim 1, wherein the donor probe and the acceptor probe are hybridized to the specimen sequentially iand adjacently in the hybrid.

3. The detection probes of claim 2, wherein either the first fluorescent dye molecule or the second fluorescent dye molecule is a terminal part at a side on which the pair of detection probes sequentially hybridizing on the specimen are adjacent with each other.

4. A pair of detection probes for detecting a specimen having a specified polynucleotide base sequence in a sample suspected of containing the specimen, said pair of detection probes comprising:

a donor probe to which a first fluorescent dye molecule is covalently bound, having a base sequence capable of hybridizing with a part of the polynucleotide base sequence; and an acceptor probe to which a second fluorescent dye molecule is covalently bound, having a base sequence capable of hybridizing with a part of the polynucleotide base sequence, wherein if any hybrid is formed among the donor probe, the acceptor probe, and the specimen, then the hybrid at least partially adopts a double-stranded structure between a first nucleotide position to which the first fluorescent dye molecule of the donor probe is bound and a second nucleotide position to which the second fluorescent dye molecule of the acceptor probe is bound, wherein the first fluorescent dye molecule has a fluorophore of a 4,4-difluoro-4-boro-3a,4a-diaza-s-indacene type and the second fluorescent dye molecule has a fluorophore of an Indocyanine type, and further wherein a fluorescence decay curve of fluorescence intensity in a wavelength region of fluorescence resulting from the second fluorescent dye molecule significantly changes due to resonance energy transfer from the donor probe to the acceptor probe when the hybrid has been formed.

5. The detection probes according to claim 4, wherein a base number between a nucleotide to which the first fluorescent dye molecule is bound and a nucleotide to which the second fluorescent dye molecule is bound is from 8 to 16 in the hybrid, and wherein the donor probe and the acceptor probe are hybridized to the specimen sequentially and adjacently in the hybrid.

6. The detection probes of claim 5, wherein either the first fluorescent dye molecule or the second fluorescent dye molecule is a terminal part at a side on which the pair of detection probes sequentially hybridizing on the specimen are adjacent with each other.

7. A method for detecting a specimen having a specified polynucleotide base sequence in a sample suspected of containing the specimen, said method comprising:

(1) the first step of providing a pair of detection probes comprising:

a donor probe to which a first fluorescent dye molecule is covalently bound, having a base sequence capable of hybridizing with a part of the polynucleotide base sequence, and an acceptor probe to which a second fluorescent dye molecule is covalently bound, having a base sequence capable of hybridizing with a part of the polynucleotide base sequence, wherein if any hybrid is formed among the donor probe, the acceptor probe, and the specimen, then the hybrid at least partially adopts a double-stranded structure between a first nucleotide position to which the first fluorescent dye molecule of the donor probe is bound and a second nucleotide position to which the second fluorescent dye molecule of the acceptor probe is bound and wherein a base number between the first nucleotide position and the second nucleotide position is from 8 to 16 in the hybrid;

(2) the second step of adding the pair of detection probes to the sample;

(3) the third step of measuring a decay curve of fluorescence intensity for any hybrid in a wavelength region of fluorescence resulting from the second fluorescent dye molecule;

(4) the fourth step of separately measuring an decay curve of fluorescence intensity for the pair of detection probes in a wavelength region of fluorescence resulting from the second fluorescent dye molecule without addition of the sample; and (5) the fifth step of comparing the fluorescence decay curve obtained in the third step and the fluorescence decay curve obtained in the fourth step to detect the presence of the specimen in the sample, whereby upon said comparison the fluorescence decay curve of fluorescence intensity in a wavelength region of fluorescence resulting from the second fluorescent dye molecule significantly changes due to resonance energy transfer from the donor probe to the acceptor probe through formation of the hybrid if the specimen is present in the sample.

8. A method for detecting a specimen having a specified polynucleotide base sequence in a sample suspected of containing the specimen, said method comprising:

(1) the first step of providing a pair of detection probes comprising: a donor probe to which a first fluorescent dye molecule is covalently bound, having a base sequence capable of hybridizing with a part of the polynucleotide base sequence, and an acceptor probe to which a second fluorescent dye molecule is covalently bound, having a base sequence capable of hybridizing with a part of the polynucleotide base sequence;

wherein if any hybrid is formed among the donor probe, the acceptor probe, and the specimen, then the hybrid at least partially adopts a double-stranded structure between a first nucleotide position to which the first fluorescent dye molecule of the donor probe is bound and a second nucleotide position to which the second fluorescent dye molecule of the acceptor probe is bound, and further;

wherein the first fluorescent dye molecule has a fluorophore of a 4,4-difluoro-4-boro-3a,4a-diaza-s-indacene type and the second fluorescent dye molecule has a fluorophore of an Indocyanine type;

(2) the second step of adding the pair of detection probes to the sample;

(3) the third step of measuring a decay curve of fluorescence intensity for any hybrid in a wavelength region of fluorescence resulting from the second fluorescent dye molecule;

(4) the fourth step of separately measuring an decay curve of fluorescence intensity for the pair of detection probes in a wavelength region of fluorescence resulting from the second fluorescent dye molecule without addition of the sample; and (5) the fifth step of comparing the fluorescence decay curve obtained in the third step and the fluorescence decay curve obtained in the fourth step to detect the presence of the specimen in the sample, whereby upon said comparison the fluorescence decay curve of fluorescence intensity in a wavelength region of fluorescence resulting from the second fluorescent dye molecule significantly changes due to resonance energy transfer from the donor probe to the acceptor probe through formation of the hybrid if the specimen is present in the sample.

9. A method for detecting a specimen having a specified polynucleotide base sequence in a sample suspected of containing the specimen, said method comprising:

(1) the first step of providing a pair of detection probes comprising: a donor probe to which a first fluorescent dye molecule is covalently bound, having a base sequence capable of hybridizing with a part of the polynucleotide base sequence, and an acceptor probe to which a second fluorescent dye molecule is covalently bound, having a base sequence capable of hybridizing with a part of the polynucleotide base sequence, wherein if any hybrid is formed among the donor probe, the acceptor probe, and the specimen, then the hybrid at least partially adopts a double-stranded structure between a first nucleotide position to which the first fluorescent dye molecule of the donor probe is bound and a second nucleotide position to which the second fluorescent dye molecule of the acceptor probe is bound;

(2) the second step of adding the pair of detection probes to the sample such that the detection probes are present in the sample in excess relative to the specimen;

(3) the third step of measuring a decay curve of fluorescence intensity for any hybrid in a wavelength region of fluorescence resulting from the second fluorescent dye molecule;

(4) the fourth step of separately measuring an decay curve of fluorescence intensity for the pair of detection probes in a wavelength region of fluorescence resulting from the second fluorescent dye molecule without addition of the sample; and (5) the fifth step of comparing the fluorescence decay curve obtained in the third step and the fluorescence decay curve obtained in the fourth step to detect the presence of the specimen in the sample, whereby upon said comparison the fluorescence decay curve of fluorescence intensity in a wavelength region of fluorescence resulting from the second fluorescent dye molecule significantly changes due to resonance energy transfer from the donor probe to the acceptor probe through formation of the hybrid if the specimen is present in the sample.

* * * * *